(12) United States Patent
Lai et al.

(10) Patent No.: US 8,969,375 B2
(45) Date of Patent: Mar. 3, 2015

(54) CDK9 KINASE INHIBITORS

(71) Applicant: AbbVie Inc., North Chicago, IL (US)

(72) Inventors: Chunqiu Lai, Libertyville, IL (US);
Zhi-Fu Tao, Vernon Hills, IL (US);
Keith W. Woods, Lincolnshire, IL (US);
Thomas D. Penning, Elmhurst, IL (US);
Andrew J. Souers, Libertyville, IL (US); Anthony Mastracchio, Waukegan, IL (US); Julie M. Miyashiro, Morton Grove, IL (US); Yunsong Tong, Libertyville, IL (US)

(73) Assignee: AbbVie, Inc., North Chicago, IL (US)

(*) Notice: Subject to any disclaimer, the term of this patent is extended or adjusted under 35 U.S.C. 154(b) by 0 days.

(21) Appl. No.: 14/207,841

(22) Filed: Mar. 13, 2014

(65) Prior Publication Data
US 2014/0275153 A1 Sep. 18, 2014

Related U.S. Application Data

(60) Provisional application No. 61/780,261, filed on Mar. 13, 2013.

(51) Int. Cl.
| | | |
|---|---|---|
| C07D 487/04 | (2006.01) |
| A61K 31/519 | (2006.01) |
| C07D 519/00 | (2006.01) |
| C07D 471/04 | (2006.01) |
| A61K 31/437 | (2006.01) |

(52) U.S. Cl.
CPC ............ *C07D 471/04* (2013.01); *A61K 31/437* (2013.01); *C07D 519/00* (2013.01); *A61K 31/519* (2013.01); *C07D 487/04* (2013.01)
USPC .......................................... 514/300; 546/113

(58) Field of Classification Search
USPC .......................................... 514/300; 546/113
See application file for complete search history.

(56) References Cited

U.S. PATENT DOCUMENTS

| | | | |
|---|---|---|---|
| 6,884,890 B2 * | 4/2005 | Kania et al. ................ | 546/275.7 |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |

FOREIGN PATENT DOCUMENTS

| | | |
|---|---|---|
| WO | 9507271 A1 | 3/1995 |
| WO | 9710223 A1 | 3/1997 |
| WO | 2003/000695 | 1/2003 |
| WO | 2005099353 A2 | 10/2005 |
| WO | 2006008754 A1 | 1/2006 |
| WO | 2006/017443 | 2/2006 |
| WO | 2008049856 A2 | 5/2008 |
| WO | 2008079918 | 7/2008 |
| WO | 2008/128072 | 10/2008 |
| WO | 2008145688 | 12/2008 |
| WO | 2009047359 A1 | 4/2009 |
| WO | 2010003133 | 1/2010 |
| WO | 2010/020675 | 2/2010 |
| WO | 2013/157021 | 10/2013 |

OTHER PUBLICATIONS

Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic N., et al., In "Dosimetry & Treatment Planning for Neutron Capture Therapy", Zamenhof R, et al., Edition, 1994, Advanced Medical Publishing, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Coley W., et al., "Novel HIV-1 Therapeutics Through Targeting Altered Host Cell Pathways.," Expert Opinion on Biological Therapy, 2009, vol. 9 (11), pp. 1369-1382.

(Continued)

Primary Examiner — Niloofar Rahmani
(74) Attorney, Agent, or Firm — Changxia Sun

(57) ABSTRACT

Disclosed are compound of Formula (Ia),

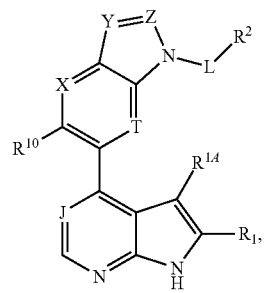

(Ia)

wherein $R^{1A}$, $R^1$, $R^2$, $R^{10}$, J, L, T, X, Y, and Z are as defined in the specification, and pharmaceutically acceptable salts thereof. The compounds may be used as agents in the treatment of diseases, including cancer. Also provided are pharmaceutical compositions, comprising one or more compounds of Formula (Ia).

17 Claims, No Drawings

(56) References Cited

OTHER PUBLICATIONS

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Foster, A. B. et al., "Deuterium Isotope Effects in the Metabolism of Drugs and Xenobiotics: Implications for Drug Design," Advances in Drug Research, 1985, vol. 14, pp. 2-36.

"IUPAC 1974 Recommendations for Section E, Fundamental Stereochemistry," Pure and Applied Chemistry, 1976, vol. 45, pp. 10-13.

Kato, S. et al., "Synthesis of Deuterated Mosapride Citrate," Journal of Labelled Compounds and Radiopharmaceuticals, 1995, vol. 36 (10), pp. 927-932.

Krystof V., et al., "Pharmacological Targeting of CDK9 in Cardiac Hypertrophy.," Medicinal Research Reviews, 2010, vol. 30 (4), pp. 646-666.

Kushner D.J., et al., "Pharmacological Uses and Perspectives of Heavy Water and Deuterated Compounds.," Canadian Journal of Physiology and Pharmacology, 1999, vol. 77 (2), pp. 79-88.

Lizondo, J. et al., "Linezolid: Oxazolidinone antibacterial," Drugs of the Future, 1996, vol. 21 (11), pp. 1116-1123.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Malumbres M., et al., "Cell Cycle, CDKs and Cancer: a Changing Paradigm.," Nature Reviews Cancer, 2009, vol. 9 (3), pp. 153-166.

Miyaura N., et al., "Palladium-Catalyzed Cross-Coupling Reactions of Organoboron Compounds," Chemical Reviews, 1995, vol. 95 (7), pp. 2457-2483.

Prescott, Ed., Methods in Cell Biology, vol. XIV, Academic Press, New York, 1976, pp. 33.

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Suzuki A, "Recent Advances in the Cross-Coupling Reactions of Organoboron Derivatives with Organic Electrophiles," Journal of Organometallic Chemistry, 1999, vol. 576, pp. 147-168.

Thomson, J.F., "Physiological Effects of D20 in Mammals," Annals of the New York Academy of Sciences, 1960, vol. 84, pp. 736-744.

Wang S., et al., "Cyclin-dependent kinase 9: a key Transcriptional Regulator and Potential Drug Target in Oncology, Virology and Cardiology.," Trends in Pharmacological Sciences, 2009, vol. 29 (6), pp. 302-312.

The International Search Report and Written Opinion for PCT/US2014/025740 mailed May 27, 2014.

The International Search Report and Written Opinion for PCT/US2014/025670 mailed May 22, 2014.

\* cited by examiner

CDK9 KINASE INHIBITORS

BACKGROUND OF THE INVENTION

Cyclin-dependent kinases (CDKs) are serine/threonine protein kinases whose activity depends on binding and activation by cyclin partners. These heterodimeric complexes can phosphorylate various substrates involved in the control of transcription and cell-cycle progression in response to different stimuli. CDK8 and CDK9 have key roles in the control of transcription by RNA polymerase II. CDK9 responds specifically to several cytokines, including tumor necrosis factor and interleukin-6, indicating that it might have special roles in the regulation of a variety of physiological processes, especially immune responses, inflammation, cell activation, and differentiation.

Deregulated CDK activity is a hallmark of human cancer, and a variety of genetic and epigenetic events, such as over expression of cyclins, diminished levels of CDK inhibiting proteins or gain-of function mutations in CDK, have been described to cause increased activity of these enzymes and provide a selective growth advantage in tumor cells. CDK9 inhibition causes rapid depletion of short-lived mRNA transcripts and their associated protein products. Many genes encoding proteins involved in cell growth, proliferation, and tumor development (Myc, Cyclin D1, and Mcl-1) are characterized by short-lived mRNAs and proteins and hence the consequences of CDK9 inhibition include anti-proliferative and pro-apoptotic effects through loss of function at many cellular pathways. Tumor types that are dependent on labile pro-survival proteins (e.g., Mcl-1), which includes multiple myeloma, CLL, breast, melanoma and pancreatic cancers as well as the MYC-driven tumors (multiple cancer types) would be susceptible to CDK9 inhibition. CDK9 inhibitors might also be effective in combination with standard of care in tumors in which NF-κB is constitutively active and contributing to chemo resistance. This includes hematologic malignancies as well as solid tumors (breast, colorectal, prostate, melanoma and pancreatic). Thus, CDK9 inhibition targets multiple cancer-relevant pathways by inhibition of a single protein and thereby renders CDK9 as an attractive target for anti-cancer therapy. (Nature Reviews Cancer: 2009, 9, 153-166).

CDK9 inhibitors can also find therapeutic application in cardiology and virology as many viruses depend on the infected host for transcription of their genome. (Cyclin-dependent kinase 9: a key transcriptional regulator and potential drug target in oncology, virology and cardiology. Trends in Pharmacol. Sci. 2009, 29. 302-312; Pharmacological targeting of CDK9 in cardiac hypertrophy. Med Res. Rev. 2010 30:646-66; Novel HIV-1 therapeutics through targeting altered host cell pathways. Expert Opin Biol Ther. 2009 9:1369-82).

CDK9 inhibitors have also been reported as potential therapeutics for the treatment of chronic, inflammatory and neuropathic pain (WO2008/049856; WO2009/047359).

In view of the above, there is a need in the art for small molecule therapeutics that can inhibit the activity of CDK9. The present invention fulfills at least this need.

SUMMARY OF THE INVENTION

In one aspect, the present invention relates to compounds of Formula (Ia) or a pharmaceutically acceptable salt thereof,

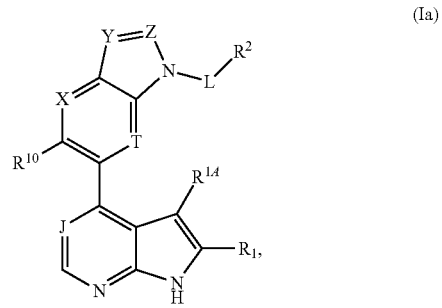

(Ia)

wherein
the bond between Y and Z is a single or a double bond;
  wherein if the bond is a double bond then Y is N or $CR^3$, and Z is N or CH; wherein if the bond is a single bond, then Y is $CH_2$ and Z is $CH_2$;
J, X, and T are each independently N or $CR^3$;
$R^3$ is selected from the group consisting of: H, $C_1$-$C_6$ alkyl, halo, CN, and $C(N)OR^{3A}$;
$R^{3A}$ is $C_1$-$C_5$ alkyl;
L is absent or is a $C_1$-$C_5$ alkylene;
$R^{1A}$ is H, $C_1$-$C_6$ alkyl, CN, or halo;
$R^2$ is H, phenyl, a 4 to 7 membered heterocycloalkyl, or a five to six membered heteroaryl;
  each of which may substituted with one to three substituents selected from the group consisting of:
    $OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of:
    $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}$, $SO_2NR^{24}R^{25}$, OH, CN, and halo;
$R^1$ is a cycloalkyl, cycloalkenyl, a heterocycloalkyl, or heterocycloalkenyl, each of which may be substituted with one to three substituents selected from the group consisting of:
    $OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{41}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo;

$R^{10}$ is H or halo;

each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NHR^{47}$, $C(O)NHR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_5$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl.

In one embodiment of Formula (Ia), $R^{1.4}$ is H or halo. In another embodiment of Formula (Ia), $R^{10}$ is H. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (Ia), $R^{1.4}$ is H or halo; and $R^1$ is a heterocycloalkyl, which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (Ia), $R^{1.4}$ is H or halo; and $R^1$ is a heterocycloalkenyl, which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a single bond; Y is $CH_2$ and Z is $CH_2$; and J, X, and T are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is N; Z is CH; and J, X, and T are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is $CR^3$; Z is CH; and J, X, and T are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is N; Z is CH; and T is N; and J and X are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is $CR^3$; Z is CH; X is N; and J and T are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is N; Z is N; and J, X, and T are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is $CR^3$; Z is CH; T is N; and J and X are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein the bond between Y and Z is a double bond; Y is $CR^3$; Z is CH; J is N; and X and T are each independently $CR^3$. In another embodiment of Formula (Ia), $R^{1.4}$ is H or halo; and $R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH; wherein L is a $C_1$ alkylene; and $R^2$ is phenyl, a 4 to 7 membered heterocycloalkyl, or a five to six membered heteroaryl; each of which may substituted with one to three halo.

Still another embodiment pertains to compounds of Formula (Ia), selected from the group consisting of 4-[1-(3-fluorobenzyl)-2,3-dihydro-1H-indol-6-yl]-2-(piperidin-4-yl)-1H-pyrrolo[2,3-b]pyridine;

1-(3-fluorobenzyl)-6-[2-(piperidin-4-yl)-1H-pyrrolo[2,3-b]pyridin-4-yl]-1H-benzimidazole;

1-benzyl-6-[2-(piperidin-4-yl)-1H-pyrrolo[2,3-b]pyridin-4-yl]-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-benzimidazole;

6-[2-(piperidin-4-yl)-1H-pyrrolo[2,3-b]pyridin-4-yl]-1-(tetrahydro-2H-pyran-4-ylmethyl)-1H-benzimidazole;

6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine;

1-(3-fluorobenzyl)-6-[2-(piperidin-4-yl)-1H-pyrrolo[2,3-b]pyridin-4-yl]-1H-indole-3-carbonitrile;

4-[5-fluoro-1-(3-fluorobenzyl)-1H-indol-6-yl]-2-(piperidin-4-yl)-1H-pyrrolo[2,3-b]pyridine;

6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-indole-3-carbonitrile;

1-[(5-fluoropyridin-3-yl)methyl]-6-[2-(piperidin-4-yl)-1H-pyrrolo[2,3-b]pyridin-4-yl]-1H-benzimidazole;

1-[(5-fluoropyridin-3-yl)methyl]-6-{2-[1-(methylsulfonyl)piperidin-4-yl]-1H-pyrrolo[2,3-b]pyridin-4-yl}-1H-benzimidazole;

1-(3-fluorobenzyl)-6-[2-(1,2,3,6-tetrahydropyridin-4-yl)-1H-pyrrolo[2,3-b]pyridin-4-yl]-1H-benzimidazole;

1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole;

4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide;

3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol;

5-fluoro-6-[2-(piperidin-4-yl)-1H-pyrrolo[2,3-b]pyridin-4-yl]-1-(tetrahydro-2H-pyran-4-ylmethyl)-1H-benzimidazole;

3-(4-{4-[5-fluoro-1-(tetrahydro-2H-pyran-4-ylmethyl)-1H-benzimidazol-6-yl]-1H-pyrrolo[2,3-b]pyridin-2-yl}piperidin-1-yl)propane-1,2-diol;

4-{4-[5-fluoro-1-(tetrahydro-2H-pyran-4-ylmethyl)-1H-benzimidazol-6-yl]-1H-pyrrolo[2,3-b]pyridin-2-yl}-N-methylpiperidine-1-carboxamide;

1-(4-{4-[5-fluoro-1-(tetrahydro-2H-pyran-4-ylmethyl)-1H-benzimidazol-6-yl]-1H-pyrrolo[2,3-b]pyridin-2-yl]piperidin-1-yl)-2-hydroxyethanone;

1-benzyl-6-[6-(1,2,3,6-tetrahydropyridin-4-yl)-7H-pyrrolo[2,3-d]pyrimidin-4-yl]-1H-indole-3-carbonitrile;

5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

4-{4-[1-(3-fluorobenzyl)-1H-benzimidazol-6-yl]-1H-pyrrolo[2,3-b]pyridin-2-yl}-N-methyl-3,6-dihydropyridine-1(2H)-carboxamide;

3-[4-{4-[1-(3-fluorobenzyl)-1H-benzimidazol-6-yl]-1H-pyrrolo[2,3-b]pyridin-2-yl]-3,6-dihydropyridin-1(2H)-yl]propane-1,2-diol;

N-(4-{[4-{4-[1-(3-fluorobenzyl)-1H-benzimidazol-6-yl]-1H-pyrrolo[2,3-b]pyridin-2-yl]-3,6-dihydropyridin-1(2H)-yl]methyl}phenyl)acetamide;

5-chloro-6-[2-(piperidin-4-yl)-1H-pyrrolo[2,3-b]pyridin-4-yl]-1-(tetrahydro-2H-pyran-4-ylmethyl)-1H-benzimidazole;

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine-3-carbonitrile;

1-(3-fluorobenzyl)-6-[2-(piperidin-4-yl)-1H-pyrrolo[2,3-b]pyridin-4-yl]-1H-pyrrolo[3,2-b]pyridine;

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine;

1-benzyl-6-{6-[1-(2,3-dihydroxypropyl)-1,2,3,6-tetrahydropyridin-4-yl]-7H-pyrrolo[2,3-d]pyrimidin-4-yl}-1H-indole-3-carbonitrile;

1-[2-(3-fluorophenyl)ethyl]-6-[2-(piperidin-4-yl)-1H-pyrrolo[2,3-b]pyridin-4-yl]-1H-benzotriazole;

6-[3-chloro-2-(piperidin-4-yl)-1H-pyrrolo[2,3-b]pyridin-4-yl]-1-[2-(3-fluorophenyl)ethyl]-1H-benzotriazole;

1-(3-fluorobenzyl)-6-{2-[1-(methylsulfonyl)piperidin-4-yl]-1H-pyrrolo[2,3-b]pyridin-4-yl}-1H-pyrrolo[3,2-b]pyridine;

1'-(3-fluorobenzyl)-2-(piperidin-4-yl)-1H,1'H-4,6'-bipyrrolo[2,3-b]pyridine-3'-carbonitrile;

1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole;

1-[(5-fluoropyridin-3-yl)methyl]-6-[2-(piperidin-4-yl)-1H-pyrrolo[2,3-b]pyridin-4-yl]-1H-pyrrolo[3,2-b]pyridine;

2-hydroxy-1-[4-{4-[1-(tetrahydro-2H-pyran-4-ylmethyl)-1H-benzotriazol-6-yl]-1H-pyrrolo[2,3-b]pyridin-2-yl]-3,6-dihydropyridin-1(2H)-yl]ethanone;

6-{2-[1-(methylsulfonyl)-1,2,3,6-tetrahydropyridin-4-yl]-1H-pyrrolo[2,3-b]pyridin-4-yl}-1-(tetrahydro-2H-pyran-4-ylmethyl)-1H-benzotriazole;

1-(3-fluorobenzyl)-6-[2-(1,2,3,6-tetrahydropyridin-4-yl)-1H-pyrrolo[2,3-b]pyridin-4-yl]-1H-pyrrolo[3,2-b]pyridine;

methyl 5-fluoro-1-(3-fluorobenzyl)-6-[2-(piperidin-4-yl)-1H-pyrrolo[2,3-b]pyridin-4-yl]-1H-indole-3-carboximidate;

5-fluoro-1-(3-fluorobenzyl)-6-[2-(piperidin-4-yl)-1H-pyrrolo[2,3-b]pyridin-4-yl]-1H-indole-3-carbonitrile;

1'-(3-fluorobenzyl)-2-(piperidin-4-yl)-1H,1'H-4,6'-bipyrrolo[2,3-b]pyridine;

2-(piperidin-4-yl)-1'-(tetrahydro-2H-pyran-4-ylmethyl)-1H,1'H-4,6'-bipyrrolo[2,3-b]pyridine;

4-{4-[1-(3-fluorobenzyl)-1H-pyrrolo[3,2-b]pyridin-6-yl]-1H-pyrrolo[2,3-b]pyridin-2-yl}-N-methylpiperidine-1-carboxamide;

6-{2-[1-(methylsulfonyl)piperidin-4-yl]-1H-pyrrolo[2,3-b]pyridin-4-yl}-1-(tetrahydro-2H-pyran-4-ylmethyl)-1H-pyrrolo[3,2-b]pyridine;

4-(4-{1-[(5-fluoropyridin-3-yl)methyl]-1H-pyrrolo[3,2-b]pyridin-6-yl}-1H-pyrrolo[2,3-b]pyridin-2-yl)-N-methylpiperidine-1-carboxamide;

1-[(5-fluoropyridin-3-yl)methyl]-6-{2-[1-(methylsulfonyl) piperidin-4-yl]-1H-pyrrolo[2,3-b]pyridin-4-yl}-1H-pyrrolo[3,2-b]pyridine;

1'-[(5-fluoropyridin-3-yl)methyl]-2-(piperidin-4-yl)-1H,1'H-4,6'-bipyrrolo[2,3-b]pyridine;

1-[(5-fluoropyridin-3-yl)methyl]-6-[2-(1,2,3,6-tetrahydropyridin-4-yl)-1H-pyrrolo[2,3-b]pyridin-4-yl]-1H-pyrrolo[3,2-b]pyridine;

1'-[(5-fluoropyridin-3-yl)methyl]-2-(1,2,3,6-tetrahydropyridin-4-yl)-1H,1'H-4,6'-bipyrrolo[2,3-b]pyridine;

4-{1'-[(5-fluoropyridin-3-yl)methyl]-1H,1'H-4,6'-bipyrrolo[2,3-b]pyridin-2-yl}-N-methylpiperidine-1-carboxamide;

1'-[(5-fluoropyridin-3-yl)methyl]-2-[1-(methylsulfonyl)piperidin-4-yl]-1H,1'H-4,6'-bipyrrolo[2,3-b]pyridine;

4-{1'-[(5-fluoropyridin-3-yl)methyl]-1H,1'H-4,6'-bipyrrolo[2,3-b]pyridin-2-yl}-N-methyl-3,6-dihydropyridine-1(2H)-carboxamide;

1'-[(5-fluoropyridin-3-yl)methyl]-2-[1-(methylsulfonyl)-1,2,3,6-tetrahydropyridin-4-yl]-1H,1'H-4,6'-bipyrrolo[2,3-b]pyridine;

1'-[(5-fluoropyridin-3-yl)methyl]-2-(1,2,5,6-tetrahydropyridin-3-yl)-1H,1'H-4,6'-bipyrrolo[2,3-b]pyridine; and pharmaceutically acceptable salts thereof.

In another aspect, the present invention relates to pharmaceutical compositions comprising a pharmaceutically acceptable exicipient and a therapeutically effective amount of a compound of Formula (Ia), or a pharmaceutically acceptable salt thereof.

In another aspect, the present invention relates to methods of treating cancer in a patient, comprising administering to a patient suffering from a cancer a therapeutically effective amount of a compound of Formula (Ia), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenstrm's macroglobulinemia, testicular tumors, uterine cancer, and Wilms' tumor. In certain embodiments, the methods further comprise administering a therapeutically effective amount of at least one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated radical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of alkyls include methyl, ethyl, n-propyl, isopropyl, n-butyl, isobutyl, sec-butyl, tert-butyl, pentyl, isoamyl, hexyl, pentan-3-y), 2,2-dimethylpropan-2-yl), heptan-4-yl, and 2,6-dimethylheptan-4-yl, and the like. The term "$C_1$-$C_5$ alkyl" refers to an alkyl substituent containing from 1 to 5 carbon atoms, "$C_1$-$C_6$ alkyl" refers to an alkyl substituent containing from 1 to 6 carbon atoms, and "$C_1$-$C_8$ alkyl" refers to an alkyl substituent containing from 1 to 8 carbon atoms.

The term "alkylene" (alone or in combination with another term(s)) means a straight- or branched-chain saturated diradical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. The term "$C_1$-$C_5$ alkylene" refers to an alkylene substituent containing from 1 to 5 carbon atoms.

The term "alkenyl" (alone or in combination with another term(s)) means a straight- or branched-chain radical of an alkene containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like. The term "$C_2$-$C_6$ alkenyl" means an alkenyl group containing 2-6 carbon atoms.

The term "alkynyl" (alone or in combination with another term(s)) means a straight- or branched-chain radical of an alkyne containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like. The term "$C_2$-$C_6$ alkynyl" means an alkynyl group of 2 to 6 carbon atoms.

The term "cycloalkyl" (alone or in combination with another term(s)) means a saturated cyclic hydrocarbyl substituent containing from 3 or more carbon ring atoms ("ring atoms" are the atoms bound together to form the ring or rings of a cyclic substituent). A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic (contain more than one ring). Examples of polycyclic cycloalkyls include bridged, fused, and spirocyclic cycloalkyls.

The term "$C_3$-$C_{10}$ cycloalkyl" (alone or in combination with another term(s)) means a saturated cyclic radical of a cycloalkane containing from 3 to 10 carbon ring atoms. Examples of cycloalkyl groups include, but are not limited to, cyclopropyl (cyclopropanyl), cyclobutyl (cyclobutanyl), cyclopentyl (cyclopentanyl), cyclopentenyl, cyclohexyl (cyclohexanyl), and cycloheptyl.

The term "cycloalkenyl" (alone or in combination with another term(s)) means a partially unsaturated cyclic hydrocarbyl substituent containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "$C_5$-$C_{10}$ cycloalkenyl" (alone or in combination with another term(s)) means a partially unsaturated monocylic cycloalkane radical containing from 5 to 10 carbon ring atoms. Examples of cycloalkenyls include cyclopentenyl, cyclohexenyl, and cycloheptenyl.

The term "heterocycloalkyl" (alone or in combination with another term(s)) means a non-aromatic saturated monocyclic or polycyclic heterocycloalkane radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkyl may be a single carbon ring, which typically contains from 3 to 8 ring atoms and more typically from 3 to 6 ring atoms. Examples of single-ring heterocycloalkyls include oxetanyl, azetidinyl, thietanyl, tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, 3-pyrrolinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, trithianyl, azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl, azocanyl, thiocanyl, oxocanyl, tetrahydro-2H-thiopyranyl 1,1-dioxide and 3,4,5,6-tetrahydro-2H-oxocinyl. A heterocycloalkyl may alternatively be polycyclic (contain more than one ring). Examples of polycyclic heterocycloalkyls include bridged, fused, and spirocyclic heterocycloalkyls in which at least one ring is a heterocycloalkyl and the others are heterocycloalkyl, or cycloalkyl rings.

The term "heterocycloalkenyl" (alone or in combination with another term(s)) means a non-aromatic partially unsaturated monocyclic or polycyclic heterocycloalkene radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkenyl may be a single carbon ring, which typically contains from 3 to 8 ring atoms and more typically from 3 to 6 ring atoms. Examples of single-ring heterocycloalkenyls include 1,2,3,6-tetrahydropyridinyl, and 4,5-dihydro-1H-imidazolyl. A heterocycloalkenyl may alternatively be polycyclic (contain more than one ring). Examples of polycyclic heterocycloalkenyls include bridged, fused, and spirocyclic heterocycloalkenyls in which at least one ring is a heterocycloalkenyl and the others are heterocycloalkenyl, heterocycloalkyl, cycloalkenyl or cycloalkyl rings. Alternatively, a polycyclic heterocycloalkenyl may consist of one or more heterocycloalkyl rings and one or more cycloalkenyl rings. Examples of polycyclic heterocycloalkenyls include 8-azabicyclo[3.2.1]oct-2-enyl, and 1,2,3,3a,4,6a-hexahydrocyclopenta[c]pyrrolyl.

The term "5 to 7 membered heterocycloalkenyl" (alone or in combination with another term(s)) means a heterocycloalkenyl that contains from 3 to 7 ring atoms.

The term "4 to 7 membered heterocycloalkyl" (alone or in combination with another term(s)) means a 4 membered, 5 membered, 6 membered or 7 membered heterocycloalkyl.

The term "5 to 7 membered heterocycloalkyl" (alone or in combination with another term(s)) means a 5 membered, 6 membered or 7 membered heterocycloalkyl.

The term "4-membered monocyclic heterocycloalkyl" (alone or in combination with another term(s)) means a 4-membered, monocyclic radical having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

The term "5-membered monocyclic heterocycloalkyl" (alone or in combination with another term(s)) means a 5-membered, monocyclic radical having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

The term "6-membered monocyclic heterocycloalkyl" (alone or in combination with another term(s)) means a 6-membered, monocyclic radical having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

The term "7-membered monocyclic heterocycloalkyl" (alone or in combination with another term(s)) means a 7-membered, monocyclic radical having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1 O; 1 S and 2 O; 1 O and 1 N; and 1 O and 2 N. Illustrative examples of 7-membered monocyclic heterocycloalkyls include azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

The term "8-membered monocyclic heterocycloalkyl" (alone or in combination with another term(s)) means a 8-membered, monocyclic radical having from 5 to 7 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The nitrogen and sulfur heteroatoms in the heterocycloalkyl rings may optionally be oxidized (e.g. 1,1-dioxidotetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

The term "aryl" (alone or in combination with another term(s)) means an aromatic hydrocarbon radical. Furthermore, the term "aryl" includes polycyclic aryl groups, such as bicyclic, e.g., naphthyl. Typical aryl groups include phenyl, and naphthyl. The term aryl also includes a "9- to 12-membered bicyclic aryl," which is a ring structure formed by the fusion of a benzene ring to: (1) a cycloalkyl or cycloalkenyl (e.g., indanyl; 1,2,3,4-tetrahydro-naphthalenyl; 6,7,8,9-tetrahydro-5H-benzocycloheptenyl, etc.); (2) another benzene ring (e.g., naphthalenyl); wherein the fusion junctions are at adjacent carbons on the benzene ring; or (3) a heterocycloalkyl or heterocycloalkenyl (e.g., benzo[d][1,3]dioxolyl, isoindolinyl).

The term "heteroaryl" (alone or in combination with another term(s)) means a monocyclic 5 or 6 membered heteroaryl or a bicyclic heteroaryl.

The term "five to six membered heteroaryl" (alone or in combination with another term(s)) means a monocyclic 5 or 6 membered heteroaryl.

The term "5-membered heteroaryl" (alone or in combination with another term(s)) means a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

The term "6-membered heteroaryl" (alone or in combination with another term(s)) means a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

The term "bicyclic heteroaryl" (alone or in combination with another term(s)) means a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a cycloalkyl or cycloalkenyl; (4) a heterocycloalkyl or heterocycloalkenyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK9 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.,* 36(10):927-932 (1995); Kushner et al., *Can. J. Physiol. Pharmacol.,* 77, 79-88 (1999).

In addition, non-radio active isotope containing drugs, such as deuterated drugs called "heavy drugs," can be used for the treatment of diseases and conditions related to CDK9 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Suitable groups for $R^1$, $R^2$, $R^{10}$, X, Y, Z, L, J and T in compounds of Formula (I), $R^1$, $R^{1A}$, $R^2$, $R^{10}$, Y, Z, L, J and T in compounds of Formula (Ia), $R^1$, $R^{1A}$, $R^2$, $R^{10}$, X, Y, Z, L, and T in compounds of Formula (IIa), and $R^{1X}$, $R^{1A}$, $R^2$, $R^{10}$, X, Y, Z, L, and T in compounds of Formula (IIIc) are independently selected. The described embodiments of the present invention may be combined. Such combination is contemplated and within the scope of the present invention. For example, it is contemplated that embodiments for any of $R^1$, $R^{1A}$, $R^2$, $R^{10}$, X, Y, Z, L, J and T in compounds of Formula (Ia) can be combined with embodiments defined for any other of $R^1$, $R^{1A}$, $R^2$, $R^{10}$, X, Y, Y, Z, L, J and T in compounds of Formula (Ia).

Embodiments of Formula (I)

In one aspect, the present invention relates to compounds of Formula (I) or a pharmaceutically acceptable salt thereof:

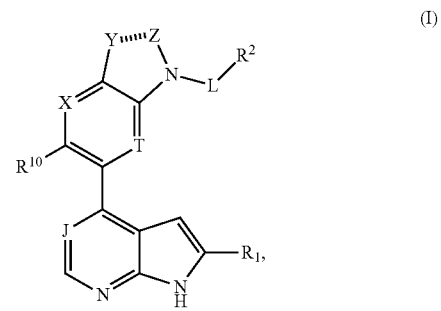

(I)

wherein:
the hashed bond between Y and Z is a single or a double bond,
  wherein if the hashed bond is a double bond then Y is N or $CR^3$, Z is N or CH, and $R^3$ is selected from the group consisting of: —CN and H;
  wherein if the if the hashed bond is a single bond, then Y is $CH_2$ and Z is CH;
J, X, Y, and T are each independently chosen from N or CH;
L is absent or is a $C_1$-$C_5$ alkylene;
$R^2$ is phenyl, a 5 to 7 membered heterocycloalkyl, a five to seven membered heteroaryl, each of which may substituted with one to three substituents selected from the group consisting of:
  —$OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl;
  wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of:
    $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^5S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}$, $SO_2NR^{24}R^{25}$, OH, CN, and halo;
$R^1$ is a $C_4$-$C_7$ cycloalkyl, a 5 to 7 membered heterocycloalkyl, or a 5 to 7 membered 5 to 7 membered heterocycloalkenyl, each of which may be substituted with one to three substituents selected from the group consisting of:—$OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{47}S(O)_2R^{44}$, $NHC(O)OR^{38}$, $NHC(O)NH_2$, $NHC(O)NHR^{39}$, $NHC(O)NR^{40}R^{41}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo;

$R^{10}$ is H or halo; and each of $R^{11}$ to $R^{40}$, are independently selected from the group consisting of:

—$C_1$-$C_5$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl.

In certain embodiments, J X, Y, and T are each CH, and L is $C_1$-$C_3$ alkylene. In certain embodiments, L is a $C_1$-alkylene. In certain embodiments, $R^1$ is a 5 to 7 membered heterocycloalkyl, optionally substituted with one of the following substitutents: $SO_2$—$C_1$-$C_3$ alkyl; a $C_1$-$C_5$ that is optionally substituted with one or two hydroxyls; —C(O)—$NR^4R^5$, wherein $R^4$ and $R^5$ are independently selected from H and —$C_1$-$C_3$ alkyl; and —C(O)—$C_1$-$C_3$ alkylene-OH. In certain embodiments, the hashed bond is a double bond. In certain embodiments, Y is N and Z is CH. In certain embodiments, Y is $CR^3$ and Z is CH. In certain embodiments, $R^2$ is phenyl, which may substituted with one to three substituents selected from the group consisting of: halo or $C_1$-$C_3$ alkyl. In certain embodiments, $R^2$ is a five to seven membered heteroaryl, which may substituted with one to three substituents selected from the group consisting of: halo or $C_1$-$C_3$ alkyl. In certain embodiments, $R^2$ is a 5 to 7 membered heterocycloalkyl, which may substituted with one to three substituents selected from the group consisting of: halo or $C_1$-$C_3$ alkyl. In certain embodiments, $R^1$ is piperidinyl or 1,2,3,6-tetrahydropyridinyl, optionally substituted with one of the following substitutents: $SO_2$—$C_1$-$C_3$ alkyl; a $C_1$-$C_5$ alkyl that is optionally substituted with one or two hydroxyls; —C(O)—$NR^4R^5$, wherein $R^4$ and $R^5$ are independently selected from H and —$C_1$-$C_3$ alkyl; and —C(O)—$C_1$-$C_3$ alkylene-OH. In certain embodiments, $R^1$ is selected from the group consisting of: piperidin-4-yl, 1-methylsulfonyl-piperidin-4-yl, 1,2,3,6-tetrahydropyridin-4-yl, 1-methylsulfonyl-1,2,3,6-tetrahydropyridin-4-yl, 1-(2-hydroxyacetyl)piperidin-4-yl, 1-(methylcarbamoyl)piperidin-4-yl, and 1-(2,3-dihydroxypropyl)piperidin-4-yl. In certain embodiments, $R^2$ is selected from the group consisting of: phenyl, pyridinyl, and tetrahydropyranyl, each of which may substituted with one to three substituents selected from the group consisting of: halo or $C_1$-$C_3$ alkyl. In certain embodiments, $R^2$ is selected from the group consisting of: 3-fluoro-phenyl, 5-fluoro-pyridin-3-yl, and tetrahydropyran-4-yl. In certain embodiments, a compound of formula I is selected from the group consisting of:

4-[1-(3-fluorobenzyl)-2,3-dihydro-1H-indol-6-yl]-2-(piperidin-4-yl)-1H-pyrrolo[2,3-b]pyridine;

1-(3-fluorobenzyl)-6-[2-(piperidin-4-yl)-1H-pyrrolo[2,3-b]pyridin-4-yl]-1H-benzimidazole;

1-benzyl-6-[2-(piperidin-4-yl)-1H-pyrrolo[2,3-b]pyridin-4-yl]-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-benzimidazole;

6-[2-(piperidin-4-yl)-1H-pyrrolo[2,3-b]pyridin-4-yl]-1-(tetrahydro-2H-pyran-4-ylmethyl)-1H-benzimidazole;

6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine;

1-(3-fluorobenzyl)-6-[2-(piperidin-4-yl)-1H-pyrrolo[2,3-b]pyridin-4-yl]-1H-indole-3-carbonitrile;

4-[5-fluoro-1-(3-fluorobenzyl)-1H-indol-6-yl]-2-(piperidin-4-yl)-1H-pyrrolo[2,3-b]pyridine;

6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-indole-3-carbonitrile;

1-[(5-fluoropyridin-3-yl)methyl]-6-[2-(piperidin-4-yl)-1H-pyrrolo[2,3-b]pyridin-4-yl]-1H-benzimidazole;

1-[(5-fluoropyridin-3-yl)methyl]-6-{2-[1-(methyl sulfonyl)piperidin-4-yl]-1H-pyrrolo[2,3-b]pyridin-4-yl}-1H-benzimidazole;

1-(3-fluorobenzyl)-6-[2-(1,2,3,6-tetrahydropyridin-4-yl)-1H-pyrrolo[2,3-b]pyridin-4-yl]-1H-benzimidazole;

1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole;

4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide;

3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol;

5-fluoro-6-[2-(piperidin-4-yl)-1H-pyrrolo[2,3-b]pyridin-4-yl]-1-(tetrahydro-2H-pyran-4-ylmethyl)-1H-benzimidazole;

3-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)propane-1,2-diol;

4-{4-[5-fluoro-1-(tetrahydro-2H-pyran-4-ylmethyl)-1H-benzimidazol-6-yl}-1H-pyrrolo[2,3-b]pyridin-2-yl]-N-methylpiperidine-1-carboxamide;

1-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)-2-hydroxyethanone;

1-benzyl-6-[6-(1,2,3,6-tetrahydropyridin-4-yl)-7H-pyrrolo[2,3-d]pyrimidin-4-yl]-1H-indole-3-carbonitrile; and 5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole; or pharmaceutically acceptable salt thereof.

Embodiments of Formula (Ia)

In one aspect, the present invention relates to compounds of Formula (Ia) or a pharmaceutically acceptable salt thereof,

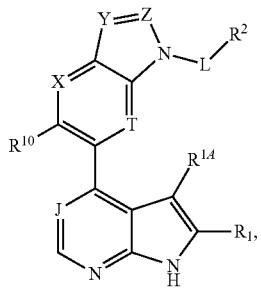

(Ia)

wherein the bond between Y and Z is a single or a double bond; wherein if the bond is a double bond then Y is N or $CR^3$, and Z is N or CH; wherein if the bond is a single bond, then Y is $CH_2$ and Z is $CH_2$;

J, X, and T are each independently N or $CR^3$;

$R^3$ is selected from the group consisting of: H, $C_1$-$C_6$ alkyl, halo, CN, and $C(N)OR^{3A}$;

$R^{3A}$ is $C_1$-$C_5$ alkyl;

L is absent or is a $C_1$-$C_5$ alkylene;

$R^{1A}$ is H, $C_1$-$C_6$ alkyl, CN, or halo;

$R^2$ is H, phenyl, a 4 to 7 membered heterocycloalkyl, or a five to six membered heteroaryl;

each of which may substituted with one to three substituents selected from the group consisting of: $OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}$, $SO_2NR^{24}R^{25}$, OH, CN, and halo;

$R^1$ is a cycloalkyl, cycloalkenyl, a heterocycloalkyl, or heterocycloalkenyl, each of which may be substituted with one to three selected from the group consisting of: $OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{41}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo;

$R^{10}$ is H or halo;

each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NHR^{47}$, $C(O)NR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_5$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl.

In one embodiment of Formula (Ia), the bond between Y and Z is a single or a double bond. In another embodiment of Formula (Ia), the bond between Y and Z is a single bond. In another embodiment of Formula (Ia), the bond between Y and Z is a double bond.

In one embodiment of Formula (Ia), the bond between Y and Z is a single bond; and Y is $CH_2$ and Z is $CH_2$. In another embodiment of Formula (Ia), the bond between Y and Z is a double bond; Y is N or $CR^3$; and Z is N or CH. In another embodiment of Formula (Ia), the bond between Y and Z is a double bond; Y is N; and Z is CH. In another embodiment of Formula (Ia), the bond between Y and Z is a double bond; Y is $CR^3$; and Z is CH. In another embodiment of Formula (Ia), the bond between Y and Z is a double bond; Y is N; and Z is N.

In one embodiment of Formula (Ia), J, X, and T are each independently N or $CR^3$. In another embodiment of Formula (Ia), J, X, and T are each independently $CR^3$. In another embodiment of Formula (Ia), J is N; and X, and T are each independently $CR^3$. In another embodiment of Formula (Ia), X is N; and J and T are each independently $CR^3$. In another embodiment of Formula (Ia), T is N; and J and X are each independently $CR^3$.

In one embodiment of Formula (Ia), the bond between Y and Z is a single bond; Y is $CH_2$ and Z is $CH_2$; and J, X, and T are each independently $CR^3$. In another embodiment of Formula (Ia), the bond between Y and Z is a double bond; Y is N; and Z is CH; and J, X, and T are each independently $CR^3$. In another embodiment of Formula (Ia), the bond between Y and Z is a double bond; Y is $CR^3$; and Z is CH; and J, X, and T are each independently $CR^3$. In another embodiment of Formula (Ia), the bond between Y and Z is a double bond; Y is N; and Z is CH; and J and X are each independently $CR^3$; and T is N. In another embodiment of Formula (Ia), the bond between Y and Z is a double bond; Y is $CR^3$; and Z is CH; and J and T are each independently $CR^3$; and X is N. In another embodiment of Formula (Ia), the bond between Y and Z is a double bond; Y is N; and Z is CH; and J, X, and T are each independently $CR^3$. In another embodiment of Formula (Ia), the bond between Y and Z is a double bond; Y is $CR^3$; and Z is CH; and J and X are each independently $CR^3$; and T is N. In another embodiment of Formula (Ia), the bond between Y and Z is a double bond; Y is $CR^3$; and Z is CH; and T and X are each independently $CR^3$; and J is N.

In one embodiment of Formula (Ia), $R^3$ is selected from the group consisting of: H, $C_1$-$C_6$ alkyl, halo, CN, and $C(N)OR^{3A}$; and $R^{3A}$ is $C_1$-$C_5$ alkyl. In another embodiment of Formula (Ia), $R^3$ is selected from the group consisting of: H, CN, and $C(N)OR^{3A}$; and $R^{3A}$ is $C_1$-$C_5$ alkyl.

In one embodiment of Formula (Ia), $R^{1A}$ is H, $C_1$-$C_6$ alkyl, CN, or halo. In another embodiment of Formula (Ia), $R^{1A}$ is H or halo. In another embodiment of Formula (Ia), $R^{1A}$ is H. In another embodiment of Formula (Ia), $R^{1A}$ is halo.

In one embodiment of Formula (Ia), $R^{10}$ is H or halo. In another embodiment of Formula (Ia), $R^{10}$ is H. In another embodiment of Formula (Ia), $R^{10}$ is halo.

In one embodiment of Formula (Ia), L is absent or is a $C_1$-$C_5$ alkylene; and $R^2$ is H, phenyl, a 4 to 7 membered heterocycloalkyl, or a five to six membered heteroaryl; each of which may substituted with one to three substituents selected from the group consisting of: $OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}$, $SO_2NR^{24}R^{25}$, OH, CN, and halo. In another embodiment of Formula (Ia), L is a $C_1$ alkylene; and $R^2$ is phenyl, a 4 to 7 membered heterocycloalkyl, or a five to six membered heteroaryl; each of which may substituted with one to three halo. In another embodiment of Formula (Ia), L is a $C_1$ alkylene; and $R^2$ is phenyl; which may substituted with one to three halo. In another embodiment of Formula (Ia), L is a $C_1$ alkylene; and $R^2$ is a 4 to 7 membered heterocycloalkyl; which may substituted with one to three halo. In another embodiment of Formula (Ia), L is a $C_1$ alkylene; and $R^2$ is a five to six membered heteroaryl; which may substituted with one to three halo.

In one embodiment of Formula (Ia), $R^1$ is a cycloalkyl, cycloalkenyl, a heterocycloalkyl, or heterocycloalkenyl, each of which may be substituted with one to three substituents selected from the group consisting of: $OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{40}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo. In another embodiment of Formula (Ia), $R^1$ is heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (Ia), $R^1$ is heterocycloalkyl which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (Ia), $R^1$ is heterocycloalkenyl, which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH.

In one embodiment of Formula (Ia), each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NHR^{47}$, $C(O)NR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl. In another embodiment of Formula (Ia), each of $R^{11}$ to $R^{41}$, are independently selected from the group consisting of: $C_1$-$C_8$ alkyl and aryl; wherein each $R^{11}$ to $R^{41}$ $C_1$-$C_8$ alkyl and aryl may be substituted with one to three substituents independently selected from the group consisting of $NHC(O)R^{45}$, and OH; and each of $R^{42}$ to $R^{49}$, are independently $C_1$-$C_8$ alkyl. In another embodiment of Formula (Ia), each of $R^{28}$, $R^{29}$, $R^{31}$, and $R^{34}$ are independently selected from the group consisting of: $C_1$-$C_8$ alkyl and aryl; wherein each $R^{28}$, $R^{29}$, $R^{31}$, and $R^{34}$ $C_1$-$C_8$ alkyl and aryl may be substituted with one to three substituents independently selected from the group consisting of $NHC(O)R^{45}$, and OH; and each $R^{45}$ is independently $C_1$-$C_8$ alkyl.

In one embodiment of Formula (Ia),
the bond between Y and Z is a single or a double bond;
wherein if the bond is a double bond then Y is N or $CR^3$, and Z is N or CH; wherein if the bond is a single bond, then Y is $CH_2$ and Z is $CH_2$;
J, X, and T are each independently N or $CR^3$;
$R^3$ is selected from the group consisting of: H, CN, and $C(N)OR^{3.4}$;
$R^{3.4}$ is $C_1$-$C_5$ alkyl;
L is $C_1$-$C_5$ alkylene;
$R^{1.4}$ is H, or halo;
$R^2$ is H, phenyl, a 4 to 7 membered heterocycloalkyl, or a five to six membered heteroaryl;
each of which may substituted with one to three halo;
$R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH;
$R^{10}$ is H or halo;
each of $R^{28}$, $R^{29}$, $R^{31}$, and $R^{34}$, are independently selected from the group consisting of: $C_1$-$C_8$ alkyl and aryl; wherein each $R^{28}$, $R^{29}$, $R^{31}$, and $R^{34}$ $C_1$-$C_8$ alkyl and aryl may be substituted with one to three substituents independently selected from the group consisting of $NHC(O)R^{45}$ and OH; and
$R^{45}$ is $C_1$-$C_5$ alkyl.

Still another embodiment pertains to compounds of Formula (Ia), selected from the group consisting of
4-[1-(3-fluorobenzyl)-2,3-dihydro-1H-indol-6-yl]-2-(piperidin-4-yl)-1H-pyrrolo[2,3-b]pyridine;
1-(3-fluorobenzyl)-6-[2-(piperidin-4-yl)-1H-pyrrolo[2,3-b]pyridin-4-yl]-1H-benzimidazole;
1-benzyl-6-[2-(piperidin-4-yl)-1H-pyrrolo[2,3-b]pyridin-4-yl]-1H-indole-3-carbonitrile;
1-(3-fluorobenzyl)-6-{2-[1-(methylsulfonyl)piperidin-4-yl]-1H-pyrrolo[2,3-b]pyridin-4-yl}-1H-benzimidazole;
6-[2-(piperidin-4-yl)-1H-pyrrolo[2,3-b]pyridin-4-yl]-1-(tetrahydro-2H-pyran-4-ylmethyl)-1H-benzimidazole;
6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;
5-[2-(piperidin-4-yl)-1H-pyrrolo[2,3-b]pyridin-4-yl]-3-(tetrahydro-2H-pyran-4-ylmethyl)-3H-imidazo[4,5-b]pyridine;
1-(3-fluorobenzyl)-6-[2-(piperidin-4-yl)-1H-pyrrolo[2,3-b]pyridin-4-yl]-1H-indole-3-carbonitrile;
4-[5-fluoro-1-(3-fluorobenzyl)-1H-indol-6-yl]-2-(piperidin-4-yl)-1H-pyrrolo[2,3-b]pyridine;
6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile;
1-(3-fluorobenzyl)-6-{2-[1-(methylsulfonyl)piperidin-4-yl]-1H-pyrrolo[2,3-b]pyridin-4-yl}-1H-indole-3-carbonitrile;
1[(5-fluoropyridin-3-yl)methyl]-6-[2-(piperidin-4-yl)-1H-pyrrolo[2,3-b]pyridin-4-yl]-1H-benzimidazole;
1-[(5-fluoropyridin-3-yl)methyl]-6-{2-[1-(methylsulfonyl)piperidin-4-yl]-1H-pyrrolo[2,3-b]pyridin-4-yl}-1H-benzimidazole;
1-(3-fluorobenzyl)-6-[2-(1,2,3,6-tetrahydropyridin-4-yl)-1H-pyrrolo[2,3-b]pyridin-4-yl]-1H-benzimidazole;
1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole;
4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide;
3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol;
5-fluoro-6-[2-(piperidin-4-yl)-1H-pyrrolo[2,3-b]pyridin-4-yl]-1-(tetrahydro-2H-pyran-4-ylmethyl)-1H-benzimidazole;
3-(4-{4-[5-fluoro-1-(tetrahydro-2H-pyran-4-ylmethyl)-1H-benzimidazol-6-yl]-1H-pyrrolo[2,3-b]pyridin-2-yl]piperidin-1-yl)propane-1,2-diol;
4-{4-[5-fluoro-1-(tetrahydro-2H-pyran-4-ylmethyl)-1H-benzimidazol-6-yl]-1H-pyrrolo[2,3-b]pyridin-2-yl]-N-methylpiperidine-1-carboxamide;
1-(4-{4-[5-fluoro-1-(tetrahydro-2H-pyran-4-ylmethyl)-1H-benzimidazol-6-yl]-1H-pyrrolo[2,3-b]pyridin-2-yl]piperidin-1-yl)-2-hydroxyethanone;
1-benzyl-6-[6-(1,2,3,6-tetrahydropyridin-4-yl)-7H-pyrrolo[2,3-d]pyrimidin-4-yl]-1H-indole-3-carbonitrile;
5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;
4-{4-[1-(3-fluorobenzyl)-1H-benzimidazol-6-yl]-1H-pyrrolo[2,3-b]pyridin-2-yl]-N-methyl-3,6-dihydropyridine-1(2H)-carboxamide;
3-[4-{4-[1-(3-fluorobenzyl)-1H-benzimidazol-6-yl]-1H-pyrrolo[2,3-b]pyridin-2-yl-}-3,6-dihydropyridin-1(2H)-yl]propane-1,2-diol;
N-(4-{[4-{4-[1-(3-fluorobenzyl)-1H-benzimidazol-6-yl]-1H-pyrrolo[2,3-b]pyridin-2-yl]-3,6-dihydropyridin-1(2H)-yl]methyl}phenyl)acetamide;
5-chloro-6-[2-(piperidin-4-yl)-1H-pyrrolo[2,3-b]pyridin-4-yl]-1-(tetrahydro-2H-pyran-4-ylmethyl)-1H-benzimidazole;
6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine-3-carbonitrile;
1-(3-fluorobenzyl)-6-[2-(piperidin-4-yl)-1H-pyrrolo[2,3-b]pyridin-4-yl]-1H-pyrrolo[3,2-b]pyridine;
6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine;
1-benzyl-6-{6-[1-(2,3-dihydroxypropyl)-1,2,3,6-tetrahydropyridin-4-yl]-7H-pyrrolo[2,3-d]pyrimidin-4-yl}-1H-indole-3-carbonitrile;
1-[2-(3-fluorophenyl)ethyl]-6-[2-(piperidin-4-yl)-1H-pyrrolo[2,3-b]pyridin-4-yl]-1H-benzotriazole;
6-[3-chloro-2-(piperidin-4-yl)-1H-pyrrolo[2,3-b]pyridin-4-yl]-1-[2-(3-fluorophenyl)ethyl]-1H-benzotriazole;
1-(3-fluorobenzyl)-6-{2-[1-(methylsulfonyl)piperidin-4-yl]-1H-pyrrolo[2,3-b]pyridin-4-yl}-1H-pyrrolo[3,2-b]pyridine;
1'-(3-fluorobenzyl)-2-(piperidin-4-yl)-1H,1'H-4,6'-bipyrrolo[2,3-b]pyridine-3'-carbonitrile;
1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole;
1-[(5-fluoropyridin-3-yl)methyl]-6-[2-(piperidin-4-yl)-1H-pyrrolo[2,3-b]pyridin-4-yl]-1H-pyrrolo[3,2-b]pyridine;
2-hydroxy-1-[4-{4-[1-(tetrahydro-2H-pyran-4-ylmethyl)-1H-benzotriazol-6-yl]-1H-pyrrolo[2,3-b]pyridin-2-yl]-3,6-dihydropyridin-1(2H)-yl]ethanone;
6-{2-[1-(methylsulfonyl)-1,2,3,6-tetrahydropyridin-4-yl]-1H-pyrrolo[2,3-b]pyridin-4-yl}-1-(tetrahydro-2H-pyran-4-ylmethyl)-1H-benzotriazole;

1-(3-fluorobenzyl)-6-[2-(1,2,3,6-tetrahydropyridin-4-yl)-1H-pyrrolo[2,3-b]pyridin-4-yl]-1H-pyrrolo[3,2-b]pyridine;

methyl 5-fluoro-1-(3-fluorobenzyl)-6-[2-(piperidin-4-yl)-1H-pyrrolo[2,3-b]pyridin-4-yl]-1H-indole-3-carboximidate;

5-fluoro-1-(3-fluorobenzyl)-6-[2-(piperidin-4-yl)-1H-pyrrolo[2,3-b]pyridin-4-yl]-1H-indole-3-carbonitrile;

1'-(3-fluorobenzyl)-2-(piperidin-4-yl)-1H,1'H-4,6'-bipyrrolo[2,3-b]pyridine;

2-(piperidin-4-yl)-1'-(tetrahydro-2H-pyran-4-ylmethyl)-1H,1'H-4,6'-bipyrrolo[2,3-b]pyridine;

4-{4-[1-(3-fluorobenzyl)-1H-pyrrolo[3,2-b]pyridin-6-yl]-1H-pyrrolo[2,3-b]pyridin-2-yl}-N-methylpiperidine-1-carboxamide;

6-{2-[1-(methylsulfonyl)piperidin-4-yl]-1H-pyrrolo[2,3-b]pyridin-4-yl}-1-(tetrahydro-2H-pyran-4-ylmethyl)-1H-pyrrolo[3,2-b]pyridine;

4-(4-{1-[(5-fluoropyridin-3-yl)methyl]-1H-pyrrolo[3,2-b]pyridin-6-yl}-1H-pyrrolo[2,3-b]pyridin-2-yl)-N-methylpiperidine-1-carboxamide;

1-[(5-fluoropyridin-3-yl)methyl]-6-{2-[1-(methylsulfonyl)piperidin-4-yl]-1H-pyrrolo[2,3-b]pyridin-4-yl}-1H-pyrrolo[3,2-b]pyridine;

1'-[(5-fluoropyridin-3-yl)methyl]-2-(piperidin-4-yl)-1H,1'H-4,6'-bipyrrolo[2,3-b]pyridine;

1-[(5-fluoropyridin-3-yl)methyl]-6-[2-(1,2,3,6-tetrahydropyridin-4-yl)-1H-pyrrolo[2,3-b]pyridin-4-yl]-1H-pyrrolo[3,2-b]pyridine;

1'-[(5-fluoropyridin-3-yl)methyl]-2-(1,2,3,6-tetrahydropyridin-4-yl)-1H,1'H-4,6'-bipyrrolo[2,3-b]pyridine;

4-{1'-[(5-fluoropyridin-3-yl)methyl]-1H,1'H-4,6'-bipyrrolo[2,3-b]pyridin-2-yl}-N-methylpiperidine-1-carboxamide;

1'-[(5-fluoropyridin-3-yl)methyl]-2-[1-(methylsulfonyl)piperidin-4-yl]-1H,1'H-4,6'-bipyrrolo[2,3-b]pyridine;

4-{1'[(5-fluoropyridin-3-yl)methyl]-1H, 1'H-4,6'-bipyrrolo[2,3-b]pyridin-2-yl}-N-methyl-3,6-dihydropyridine-1(2H)-carboxamide;

1'-[(5-fluoropyridin-3-yl)methyl]-2-[1-(methylsulfonyl)-1,2,3,6-tetrahydropyridin-4-yl]-1H,1'H-4,6'-bipyrrolo[2,3-b]pyridine;

1'-[(5-fluoropyridin-3-yl)methyl]-2-(1,2,5,6-tetrahydropyridin-3-yl)-1H,1'H-4,6'-bipyrrolo[2,3-b]pyridine; and pharmaceutically acceptable salts thereof.

Embodiments of Formula (IIa)

In one aspect, the present invention relates to compounds of Formula (IIa) or a pharmaceutically acceptable salt thereof,

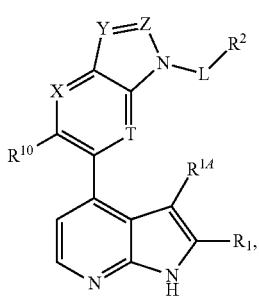

(IIa)

wherein
the bond between Y and Z is a single or a double bond;
wherein if the bond is a double bond then Y is N or $CR^3$, and Z is N or CH; wherein if the bond is a single bond, then Y is $CH_2$ and Z is $CH_2$;
X, and T are each independently N or $CR^3$;
$R^3$ is selected from the group consisting of: H, $C_1$-$C_6$ alkyl, halo, CN, and $C(N)OR^{3A}$;
$R^{3A}$ is $C_1$-$C_5$ alkyl;
L is absent or is a $C_1$-$C_5$ alkylene;
$R^{1A}$ is H, $C_1$-$C_6$ alkyl, CN, or halo;
$R^2$ is H, phenyl, a 4 to 7 membered heterocycloalkyl, or a five to six membered heteroaryl;
each of which may substituted with one to three substituents selected from the group consisting of:
$OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl;
wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}$, $SO_2NR^{24}R^{25}$, OH, CN, and halo;

$R^1$ is a cycloalkyl, cycloalkenyl, a heterocycloalkyl, or heterocycloalkenyl, each of which may be substituted with one to three substituents selected from the group consisting of: $OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo;

$R^{10}$ is H or halo;
each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NHR^{47}$, $C(O)NR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_5$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl.

In one embodiment of Formula (IIa), the bond between Y and Z is a single or a double bond. In another embodiment of Formula (IIa), the bond between Y and Z is a single bond. In another embodiment of Formula (IIa), the bond between Y and Z is a double bond.

In one embodiment of Formula (IIa), the bond between Y and Z is a single bond; and Y is $CH_2$ and Z is $CH_2$. In another embodiment of Formula (IIa), the bond between Y and Z is a double bond; Y is N or $CR^3$; and Z is N or CH. In another embodiment of Formula (IIa), the bond between Y and Z is a double bond; Y is N; and Z is CH. In another embodiment of Formula (IIa), the bond between Y and Z is a double bond; Y is $CR^3$; and Z is CH. In another embodiment of Formula (IIa), the bond between Y and Z is a double bond; Y is N; and Z is N.

In one embodiment of Formula (IIa), X, and T are each independently N or $CR^3$. In another embodiment of Formula (IIa), X and T are each independently $CR^3$. In another embodiment of Formula (IIa), X is N; and T is independently $CR^3$. In another embodiment of Formula (IIa), T is N; and X is independently $CR^3$.

In one embodiment of Formula (IIa), the bond between Y and Z is a single bond; Y is $CH_2$ and Z is $CH_2$; and X, and T are each independently $CR^3$. In another embodiment of Formula (IIa), the bond between Y and Z is a double bond; Y is N; and Z is CH; and X, and T are each independently $CR^3$. In another embodiment of Formula (IIa), the bond between Y and Z is a double bond; Y is $CR^3$; and Z is CH; and X, and T are each independently $CR^3$. In another embodiment of Formula (IIa), the bond between Y and Z is a double bond; Y is N; and Z is CH; and X is independently $CR^3$; and T is N. In another embodiment of Formula (IIa), the bond between Y and Z is a double bond; Y is $CR^3$; and Z is CH; and T is independently $CR^3$; and X is N. In another embodiment of Formula (IIa), the bond between Y and Z is a double bond; Y is N; and Z is CH; and X, and T are each independently $CR^3$. In another embodiment of Formula (IIa), the bond between Y and Z is a double bond; Y is $CR^3$; and Z is CH; and X is independently $CR^3$; and T is N. In another embodiment of Formula (IIa), the bond between Y and Z is a double bond; Y is $CR^3$; and Z is CH; and T and X are each independently $CR^3$.

In one embodiment of Formula (IIa), $R^3$ is selected from the group consisting of: H, $C_1$-$C_6$ alkyl, halo, CN, and $C(N)OR^{34}$; and $R^{34}$ is $C_1$-$C_5$ alkyl. In another embodiment of Formula (IIa), $R^3$ is selected from the group consisting of: H, CN, and $C(N)OR^{34}$; and $R^{34}$ is $C_1$-$C_5$ alkyl.

In one embodiment of Formula (IIa), $R^{14}$ is H, $C_1$-$C_6$ alkyl, CN, or halo. In another embodiment of Formula (IIa), $R^{14}$ is H or halo. In another embodiment of Formula (IIa), $R^{14}$ is H. In another embodiment of Formula (IIa), $R^{14}$ is halo.

In one embodiment of Formula (IIa), $R^{10}$ is H or halo. In another embodiment of Formula (IIa), $R^{10}$ is H. In another embodiment of Formula (IIa), $R^{10}$ is halo.

In one embodiment of Formula (IIa), L is absent or is a $C_1$-$C_5$ alkylene; and $R^2$ is H, phenyl, a 4 to 7 membered heterocycloalkyl, or a five to six membered heteroaryl; each of which may substituted with one to three substituents selected from the group consisting of: $OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{13}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}$, $SO_2NR^{24}R^{25}$, OH, CN, and halo.

In another embodiment of Formula (IIa), L is a $C_1$ alkylene; and $R^2$ is phenyl, a 4 to 7 membered heterocycloalkyl, or a five to six membered heteroaryl; each of which may substituted with one to three halo. In another embodiment of Formula (IIa), L is a $C_1$ alkylene; and $R^2$ is phenyl; which may substituted with one to three halo. In another embodiment of Formula (IIa), L is a $C_1$ alkylene; and $R^2$ is a 4 to 7 membered heterocycloalkyl; which may substituted with one to three halo. In another embodiment of Formula (IIa), L is a $C_1$ alkylene; and $R^2$ is a five to six membered heteroaryl; which may substituted with one to three halo.

In one embodiment of Formula (IIa), $R^1$ is a cycloalkyl, cycloalkenyl, a heterocycloalkyl, or heterocycloalkenyl, each of which may be substituted with one to three substituents selected from the group consisting of: $OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{41}$, $R^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo. In another embodiment of Formula (IIa), $R^1$ is heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (IIa), $R^1$ is heterocycloalkyl which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH. In another embodiment of Formula (IIa), $R^1$ is heterocycloalkenyl, which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH.

In one embodiment of Formula (IIa), each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NR^{47}$, $C(O)NR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl. In another embodiment of Formula (IIa), each of $R^{11}$ to $R^{41}$, are independently selected from the group consisting of: $C_1$-$C_8$ alkyl and aryl; wherein each $R^{11}$ to $R^{41}$ $C_1$-$C_8$ alkyl and aryl may be substituted with one to three substituents independently selected from the group consisting of $NHC(O)R^{45}$, and OH; and each of $R^{42}$ to $R^{49}$, are independently $C_1$-$C_8$ alkyl. In another embodiment of Formula (IIa), each of $R^{28}$, $R^{29}$, $R^{31}$, and $R^{34}$ are independently selected from the group consisting of: $C_1$-$C_8$ alkyl and aryl; wherein each $R^{28}$, $R^{29}$, $R^{31}$, and $R^{34}$ $C_1$-$C_8$ alkyl and aryl may be substituted with one to three substituents independently selected from the group consisting of $NHC(O)R^{45}$, and OH; and each $R^{45}$ is independently $C_1$-$C_8$ alkyl.

In one embodiment of Formula (IIa),
the bond between Y and Z is a single or a double bond; wherein if the bond is a double bond then Y is N or $CR^3$, and Z is N or CH; wherein if the bond is a single bond, then Y is $CH_2$ and Z is $CH_2$;

X and T are each independently N or $CR^3$;

$R^3$ is selected from the group consisting of: H, CN, and $C(N)OR^{34}$;

$R^{34}$ is $C_1$-$C_5$ alkyl;

L is $C_1$-$C_5$ alkylene;

$R^{14}$ is H, or halo;

$R^2$ is H, phenyl, a 4 to 7 membered heterocycloalkyl, or a five to six membered heteroaryl;
each of which may substituted with one to three halo;

$R^1$ is a heterocycloalkyl, or heterocycloalkenyl, each of which may be substituted with one to three substituents selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH;

$R^{19}$ is H or halo;

each of $R^{28}$, $R^{29}$, $R^{31}$, and $R^{34}$, are independently selected from the group consisting of: $C_1$-$C_8$ alkyl and aryl; wherein each $R^{28}$, $R^{29}$, $R^{31}$, and $R^{34}$ $C_1$-$C_8$ alkyl and aryl may be substituted with one to three substituents independently selected from the group consisting of NHC(O)$R^{45}$ and OH; and $R^{45}$ is $C_1$-$C_5$ alkyl.

Still another embodiment pertains to compounds of Formula (IIa), selected from the group consisting of 4-[1-(3-fluorobenzyl)-2,3-dihydro-1H-indol-6-yl]-2-(piperidin-4-yl)-1H-pyrrolo[2,3-b]pyridine;

1-(3-fluorobenzyl)-6-[2-(piperidin-4-yl)-1H-pyrrolo[2,3-b]pyridin-4-yl]-1H-benzimidazole;

1-benzyl-6-[2-(piperidin-4-yl)-1H-pyrrolo[2,3-b]pyridin-4-yl]-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-benzimidazole;

6-[2-(piperidin-4-yl)-1H-pyrrolo[2,3-b]pyridin-4-yl]-1-(tetrahydro-2H-pyran-4-ylmethyl)-1H-benzimidazole;

6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine;

1-(3-fluorobenzyl)-6-[2-(piperidin-4-yl)-1H-pyrrolo[2,3-b]pyridin-4-yl]-1H-indole-3-carbonitrile;

4-[5-fluoro-1-(3-fluorobenzyl)-1H-indol-6-yl]-2-(piperidin-4-yl)-1H-pyrrolo[2,3-b]pyridine;

6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-indole-3-carbonitrile;

1-[(5-fluoropyridin-3-yl)methyl]-6-[2-(piperidin-4-yl)-1H-pyrrolo[2,3-b]pyridin-4-yl]-1H-benzimidazole;

1-[(5-fluoropyridin-3-yl)methyl]-6-{2-[1-(methylsulfonyl)piperidin-4-yl]-1H-pyrrolo[2,3-b]pyridin-4-yl}-1H-benzimidazole;

1-(3-fluorobenzyl)-6-[2-(1,2,3,6-tetrahydropyridin-4-yl)-1H-pyrrolo[2,3-b]pyridin-4-yl]-1H-benzimidazole;

1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole;

4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide;

3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol;

5-fluoro-6-[2-(piperidin-4-yl)-1H-pyrrolo[2,3-b]pyridin-4-yl]-1-(tetrahydro-2H-pyran-4-ylmethyl)-1H-benzimidazole;

3-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)propane-1,2-diol;

4-{4-[5-fluoro-1-(tetrahydro-2H-pyran-4-ylmethyl)-1H-benzimidazol-6-yl}-1H-pyrrolo[2,3-b]pyridin-2-yl]-N-methylpiperidine-1-carboxamide;

1-(4-{4-[5-fluoro-1-(tetrahydro-2H-pyran-4-ylmethyl)-1H-benzimidazol-6-yl}-1H-pyrrolo[2,3-b]pyridin-2-yl}piperidin-1-yl)-2-hydroxyethanone;

5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

4-{4-[1-(3-fluorobenzyl)-1H-benzimidazol-6-yl]-1H-pyr-rolo[2,3-b]pyridin-2-yl}-N-methyl-3,6-dihydropyridine-1(2H)-carboxamide;
3-[4-{4-[1-(3-fluorobenzyl)-1H-benzimidazol-6-yl]-1H-pyrrolo[2,3-b]pyridin-2-yl}-3,6-dihydropyridin-1(2H)-yl]propane-1,2-diol;
N-(4-{[4-{4-[1-(3-fluorobenzyl)-1H-benzimidazol-6-yl]-1H-pyrrolo[2,3-b]pyridin-2-yl}-3,6-dihydropyridin-1(2H)-yl]methyl}phenyl)acetamide;
5-chloro-6-[2-(piperidin-4-yl)-1H-pyrrolo[2,3-b]pyridin-4-yl]-1-(tetrahydro-2H-pyran-4-ylmethyl)-1H-benzimidazole;
6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine-3-carbonitrile;
1-(3-fluorobenzyl)-6-[2-(piperidin-4-yl)-1H-pyrrolo[2,3-b]pyridin-4-yl]-1H-pyrrolo[3,2-b]pyridine;
6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine;
1-[2-(3-fluorophenyl)ethyl]-6-[2-(piperidin-4-yl)-1H-pyrrolo[2,3-b]pyridin-4-yl]-1H-benzotriazole;
6-[3-chloro-2-(piperidin-4-yl)-1H-pyrrolo[2,3-b]pyridin-4-yl]-1-[2-(3-fluorophenyl)ethyl]-1H-benzotriazole;
1-(3-fluorobenzyl)-6-{2-[1-(methylsulfonyl)piperidin-4-yl]-1H-pyrrolo[2,3-b]pyridin-4-yl}-1H-pyrrolo[3,2-b]pyridine;
1'-(3-fluorobenzyl)-2-(piperidin-4-yl)-1H,1'H-4,6'-bipyrrolo[2,3-b]pyridine-3'-carbonitrile;
1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole;
1-[(5-fluoropyridin-3-yl)methyl]-6-[2-(piperidin-4-yl)-1H-pyrrolo[2,3-b]pyridin-4-yl]-1H-pyrrolo[3,2-b]pyridine;
2-hydroxy-1-[4-{4-[1-(tetrahydro-2H-pyran-4-ylmethyl)-1H-benzotriazol-6-yl]-1H-pyrrolo[2,3-b]pyridin-2-yl}-3,6-dihydropyridin-1(2H)-yl]ethanone;
6-{2-[1-(methylsulfonyl)-1,2,3,6-tetrahydropyridin-4-yl]-1H-pyrrolo[2,3-b]pyridin-4-yl}-1-(tetrahydro-2H-pyran-4-ylmethyl)-1H-benzotriazole;
1-(3-fluorobenzyl)-6-[2-(1,2,3,6-tetrahydropyridin-4-yl)-1H-pyrrolo[2,3-b]pyridin-4-yl]-1H-pyrrolo[3,2-b]pyridine;
methyl 5-fluoro-1-(3-fluorobenzyl)-6-[2-(piperidin-4-yl)-1H-pyrrolo[2,3-b]pyridin-4-yl]-1H-indole-3-carboximidate;
5-fluoro-1-(3-fluorobenzyl)-6-[2-(piperidin-4-yl)-1H-pyrrolo[2,3-b]pyridin-4-yl]-1H-indole-3-carbonitrile;
1'-(3-fluorobenzyl)-2-(piperidin-4-yl)-1H,1'H-4,6'-bipyrrolo[2,3-b]pyridine;
2-(piperidin-4-yl)-1'-(tetrahydro-2H-pyran-4-ylmethyl)-1H,1'H-4,6'-bipyrrolo[2,3-b]pyridine;
4-{4-[1-(3-fluorobenzyl)-1H-pyrrolo[3,2-b]pyridin-6-yl]-1H-pyrrolo[2,3-b]pyridin-2-yl}-N-methylpiperidine-1-carboxamide;
6-{2-[1-(methylsulfonyl)piperidin-4-yl]-1H-pyrrolo[2,3-b]pyridin-4-yl}-1-(tetrahydro-2H-pyran-4-ylmethyl)-1H-pyrrolo[3,2-b]pyridine;
4-(4-{1-[(5-fluoropyridin-3-yl)methyl]-1H-pyrrolo[3,2-b]pyridin-6-yl}-1H-pyrrolo[2,3-b]pyridin-2-yl)-N-methylpiperidine-1-carboxamide;
1-[(5-fluoropyridin-3-yl)methyl]-6-{2-[1-(methylsulfonyl)piperidin-4-yl]-1H-pyrrolo[2,3-b]pyridin-4-yl}-1H-pyrrolo[3,2-b]pyridine;
1'-[(5-fluoropyridin-3-yl)methyl]-2-(piperidin-4-O-1H,1'H-4,6'-bipyrrolo[2,3-b]pyridine;
1-[(5-fluoropyridin-3-yl)methyl]-6-[2-(1,2,3,6-tetrahydropyridin-4-yl)-1H-pyrrolo[2,3-b]pyridin-4-yl]-1H-pyrrolo[3,2-b]pyridine;
1'-[(5-fluoropyridin-3-yl)methyl]-2-(1,2,3,6-tetrahydropyridin-4-O-1H,1'H-4,6'-bipyrrolo[2,3-b]pyridine;
4-{1'-[(5-fluoropyridin-3-yl)methyl]-1H,1'H-4,6'-bipyrrolo[2,3-b]pyridin-2-yl}-N-methylpiperidine-1-carboxamide;
1'-[(5-fluoropyridin-3-yl)methyl]-2-[1-(methylsulfonyl)piperidin-4-yl]-1H,1'H-4,6'-bipyrrolo[2,3-b]pyridine;
4-{1'-[(5-fluoropyridin-3-yl)methyl]-1H,1'H-4,6'-bipyrrolo[2,3-b]pyridin-2-yl}-N-methyl-3,6-dihydropyridine-1(2H)-carboxamide;
1'-[(5-fluoropyridin-3-yl)methyl]-2-[1-(methylsulfonyl)-1,2,3,6-tetrahydropyridin-4-yl]-1H,1'H-4,6'-bipyrrolo[2,3-b]pyridine;
1'-[(5-fluoropyridin-3-yl)methyl]-2-(1,2,5,6-tetrahydropyridin-3-yl)-1H,1'H-4,6'-bipyrrolo[2,3-b]pyridine; and pharmaceutically acceptable salts thereof.

Embodiments of Formula (IIIa)

In one aspect, the present invention relates to compounds of Formula (IIIa) or a pharmaceutically acceptable salt thereof,

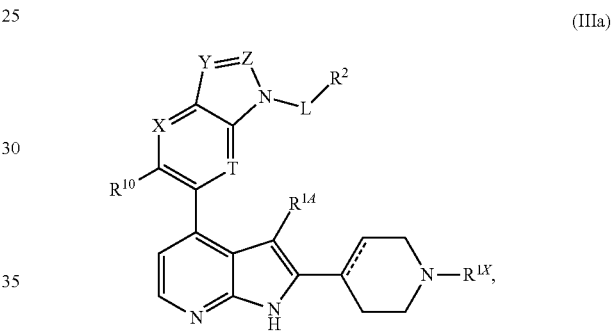

(IIIa)

wherein
the bond between Y and Z is a single or a double bond;
  wherein if the bond is a double bond then Y is N or CR$^3$, and Z is N or CH; wherein if the bond is a single bond, then Y is CH$_2$ and Z is CH$_2$;
X, and T are each independently N or CR$^3$;
R$^3$ is selected from the group consisting of: H, C$_1$-C$_6$ alkyl, halo, CN, and C(N)OR$^{3.4}$;
R$^{3.4}$ is C$_1$-C$_5$ alkyl;
L is absent or is a C$_1$-C$_5$ alkylene;
R$^{1.4}$ is H, C$_1$-C$_6$ alkyl, CN, or halo;
⁓ is a single or double bond;
R$^2$ is H, phenyl, a 4 to 7 membered heterocycloalkyl, or a five to six membered heteroaryl;
  each of which may substituted with one to three substituents selected from the group consisting of:
    OR$^{11}$, SR$^{12}$, S(O)R$^{13}$, SO$_2$R$^{13}$, C(O)R$^{14}$, CO(O)R$^{14}$, OC(O)R$^{14}$, NH$_2$, NHR$^{15}$, NR$^{16}$R$^{17}$, NHC(O)R$^{14}$, NR$^{16}$C(O)R$^{14}$, NHS(O)$_2$R$^{13}$, NR$^{15}$S(O)$_2$R$^{13}$, NHC(O)OR$^{14}$, NR$^{15}$C(O)OR$^{14}$, NHC(O)NH$_2$, NHC(O)NHR$^{15}$, NHC(O)NR$^{16}$R$^{17}$, NR$^{15}$C(O)NHR$^{16}$, NR$^{15}$C(O)NR$^{16}$R$^{17}$, C(O)NH$_2$, C(O)NHR$^{15}$, C(O)NR$^{16}$R$^{17}$, C(O)NR$^{15}$SO$_2$R$^{13}$, SO$_2$NH$_2$, SO$_2$NHR$^{15}$, SO$_2$NR$^{16}$R$^{17}$, OH, CN, halo, C$_1$-C$_8$ alkyl, C$_2$-C$_6$ alkenyl, C$_2$-C$_6$ alkynyl, aryl, heteroaryl, 5 to 7 membered heterocycloalkyl, 5 to 7 membered heterocycloalkenyl, C$_3$-C$_{10}$ cycloalkyl, and C$_5$-C$_{10}$ cycloalkenyl;
    wherein each R$^2$ aryl, C$_3$-C$_{10}$ cycloalkyl, C$_5$-C$_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{26}$, $SO_2NH_2$, $SO_2NHR^{23}$, $SO_2NR^{24}R^{25}$, OH, CN, and halo;

$R^{1X}$ is $OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, or $C_5$-$C_{10}$ cycloalkenyl; wherein each $R^{1X}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{41}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo;

$R^{10}$ is H or halo;

each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NHR^{47}$, $C(O)NR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_5$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl.

In one embodiment of Formula (IIIa), the bond between Y and Z is a single or a double bond. In another embodiment of Formula (IIIa), the bond between Y and Z is a single bond. In another embodiment of Formula (IIIa), the bond between Y and Z is a double bond.

In one embodiment of Formula (IIIa), the bond between Y and Z is a single bond; and Y is $CH_2$ and Z is $CH_2$. In another embodiment of Formula (IIIa), the bond between Y and Z is a double bond; Y is N or $CR^3$; and Z is N or CH. In another embodiment of Formula (IIIa), the bond between Y and Z is a double bond; Y is N; and Z is CH. In another embodiment of Formula (IIIa), the bond between Y and Z is a double bond; Y is $CR^3$; and Z is CH. In another embodiment of Formula (IIIa), the bond between Y and Z is a double bond; Y is N; and Z is N.

In one embodiment of Formula (IIIa), X, and T are each independently N or $CR^3$. In another embodiment of Formula (IIIa), X and T are each independently $CR^3$. In another embodiment of Formula (IIIa), X is N; and T is independently $CR^3$. In another embodiment of Formula (IIIa), T is N; and X is independently $CR^3$.

In one embodiment of Formula (IIIa), the bond between Y and Z is a single bond; Y is $CH_2$ and Z is $CH_2$; and X, and T are each independently $CR^3$. In another embodiment of Formula (IIIa), the bond between Y and Z is a double bond; Y is N; and Z is CH; and X, and T are each independently $CR^3$. In another embodiment of Formula (IIIa), the bond between Y and Z is a double bond; Y is $CR^3$; and Z is CH; and X, and T are each independently $CR^3$. In another embodiment of Formula (IIIa), the bond between Y and Z is a double bond; Y is N; and Z is CH; and X is independently $CR^3$; and T is N. In another embodiment of Formula (IIIa), the bond between Y and Z is a double bond; Y is $CR^3$; and Z is CH; and T is independently $CR^3$; and X is N. In another embodiment of Formula (IIIa), the bond between Y and Z is a double bond; Y is N; and Z is CH; and X, and T are each independently $CR^3$. In another embodiment of Formula (IIIa), the bond between Y and Z is a double bond; Y is $CR^3$; and Z is CH; and X is independently $CR^3$; and T is N. In another embodiment of Formula (IIIa), the bond between Y and Z is a double bond; Y is $CR^3$; and Z is CH; and T and X are each independently $CR^3$.

In one embodiment of Formula (IIIa), $R^3$ is selected from the group consisting of: H, $C_1$-$C_6$ alkyl, halo, CN, and $C(N)OR^{3A}$; and $R^{3A}$ is $C_1$-$C_5$ alkyl. In another embodiment of Formula (IIIa), $R^3$ is selected from the group consisting of: H, CN, and $C(N)OR^{3A}$; and $R^{3A}$ is $C_1$-$C_5$ alkyl.

In one embodiment of Formula (IIIa), $R^{1A}$ is H, $C_1$-$C_6$ alkyl, CN, or halo. In another embodiment of Formula (IIIa), $R^{1A}$ is H or halo. In another embodiment of Formula (IIIa), $R^{1A}$ is H. In another embodiment of Formula (IIIa), $R^{1A}$ is halo.

In one embodiment of Formula (IIIa), $R^{19}$ is H or halo. In another embodiment of Formula (IIIa), $R^{19}$ is H. In another embodiment of Formula (IIIa), $R^{10}$ is halo.

In one embodiment of Formula (IIIa), L is absent or is a $C_1$-$C_5$ alkylene; and $R^2$ is H, phenyl, a 4 to 7 membered heterocycloalkyl, or a five to six membered heteroaryl; each of which may substituted with one to three substituents selected from the group consisting of: $OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{29}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{29}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{29}$, $SO_2NH_2$, $SO_2NHR^{23}$, $SO_2NR^{24}R^{25}$, OH, CN, and halo. In another embodiment of Formula (IIIa), L is a $C_1$ alkylene; and $R^2$ is phenyl, a 4 to 7 membered heterocycloalkyl, or a five to six membered heteroaryl; each of which may substituted with one to three halo. In another embodiment of Formula (IIIa), L is a $C_1$ alkylene; and $R^2$ is phenyl; which may substituted with one to three halo. In another embodiment of Formula (IIIa), L is a $C_1$ alkylene; and $R^2$ is a 4 to 7 membered heterocycloalkyl; which may substituted with one to three halo. In another embodiment of Formula (IIIa), L is a $C_1$ alkylene; and $R^2$ is a five to six membered heteroaryl; which may substituted with one to three halo.

In one embodiment of Formula (IIIa), $R^{1X}$ is $OR^{26}$, $SR^{27}$, $S(O)R^{28}$, $SO_2R^{28}$, $C(O)R^{29}$, $CO(O)R^{39}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{39}$, $NR^{31}C(O)OR^{39}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, or $C_5$-$C_{10}$ cycloalkenyl; wherein each $R^{1X}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}$, $C(O)R^{37}$, $CO(O)R^{38}$, $OC(O)R^{37}$, $NH_2$, $NHR^{39}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{41}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo. In another embodiment of Formula (IIIa), $R^{1X}$ is selected from the group consisting of: $SO_2R^{28}$, $C(O)R^{29}$, $C(O)NHR^{31}$, and $C_1$-$C_8$ alkyl; wherein each $R^1$ $C_1$-$C_8$ alkyl may be substituted with one to three substituents independently selected from the group consisting of $R^{34}$ and OH.

In one embodiment of Formula (IIIa), ⚯ is a single or double bond. In another embodiment of Formula (IIIa), ⚯ is a single bond. In another embodiment of Formula (IIIa), ⚯ is a double bond.

In one embodiment of Formula (IIIa), each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, $OC(O)R^{45}$, $NH_2$, $NHR^{47}$, $NR^{48}R^{49}$, $NHC(O)R^{45}$, $NR^{47}C(O)R^{45}$, $NHS(O)_2R^{44}$, $NR^{47}S(O)_2R^{44}$, $C(O)NH_2$, $C(O)NHR^{47}$, $C(O)NR^{40}R^{41}$, $C(O)NR^{47}SO_2R^{44}$, $SO_2NH_2$, $SO_2NHR^{47}$, $SO_2NR^{48}R^{49}$, OH, CN, and halo; and each of $R^{42}$ to $R^{49}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl. In another embodiment of Formula (IIIa), each of $R^{11}$ to $R^{41}$, are independently selected from the group consisting of: $C_1$-$C_8$ alkyl and aryl; wherein each $R^{11}$ to $R^{41}$ $C_1$-$C_8$ alkyl and aryl may be substituted with one to three substituents independently selected from the group consisting of NHC(O)$R^{45}$, and OH; and each of $R^{42}$ to $R^{49}$, are independently $C_1$-$C_8$ alkyl. In another embodiment of Formula (IIIa), each of $R^{28}$, $R^{29}$, $R^{31}$, and $R^{34}$ are independently selected from the group consisting of: $C_1$-$C_8$ alkyl and aryl; wherein each $R^{28}$, $R^{29}$, $R^{31}$, and $R^{34}$ $C_1$-$C_8$ alkyl and aryl may be substituted with one to three substituents independently selected from the group consisting of NHC(O)$R^{45}$, and OH; and each $R^{45}$ is independently $C_1$-$C_8$ alkyl.

In one embodiment of Formula (IIIa),
the bond between Y and Z is a single or a double bond;
wherein if the bond is a double bond then Y is N or CR$^3$, and Z is N or CH; wherein if the bond is a single bond, then Y is CH$_2$ and Z is CH$_2$;
X and T are each independently N or CR$^3$;

$R^3$ is selected from the group consisting of: H, CN, and C(N)OR$^{3A}$;
$R^{3A}$ is $C_1$-$C_5$ alkyl;
L is $C_1$-$C_5$ alkylene;
$R^{1A}$ is H, or halo;
$R^2$ is H, phenyl, a 4 to 7 membered heterocycloalkyl, or a five to six membered heteroaryl;
each of which may substituted with one to three halo;
$R^{1X}$ is selected from the group consisting of: $SO_2R^{28}$, $C(O)R^{29}$, $C(O)NHR^{31}$, and $C_1$-$C_8$ alkyl;
wherein each $R^{1X}$ $C_1$-$C_8$ alkyl may be substituted with one to three substituents independently selected from the group consisting of $R^{34}$ and OH;
$R^{10}$ is H or halo;
each of $R^{28}$, $R^{29}$, $R^{31}$, and $R^{34}$, are independently selected from the group consisting of: $C_1$-$C_8$ alkyl and aryl; wherein each $R^{28}$, $R^{29}$, $R^{31}$, and $R^{34}$ $C_1$-$C_8$ alkyl and aryl may be substituted with one to three substituents independently selected from the group consisting of NHC(O)$R^{45}$ and OH; and
$R^{45}$ is $C_1$-$C_5$ alkyl.

Still another embodiment pertains to compounds of Formula (IIIa), selected from the group consisting of 4-[1-(3-fluorobenzyl)-2,3-dihydro-1H-indol-6-yl]-2-(piperidin-4-yl)-1H-pyrrolo[2,3-b]pyridine;

1-(3-fluorobenzyl)-6-[2-(piperidin-4-yl)-1H-pyrrolo[2,3-b]pyridin-4-yl]-1H-benzimidazole;

1-benzyl-6-[2-(piperidin-4-yl)-1H-pyrrolo[2,3-b]pyridin-4-yl]-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-benzimidazole;

6-[2-(piperidin-4-yl)-1H-pyrrolo[2,3-b]pyridin-4-yl]-1-(tetrahydro-2H-pyran-4-ylmethyl)-1H-benzimidazole;

6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine;

1-(3-fluorobenzyl)-6-[2-(piperidin-4-yl)-1H-pyrrolo[2,3-b]pyridin-4-yl]-1H-indole-3-carbonitrile;

4-[5-fluoro-1-(3-fluorobenzyl)-1H-indol-6-yl]-2-(piperidin-4-yl)-1H-pyrrolo[2,3-b]pyridine;

6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-indole-3-carbonitrile;

1[(5-fluoropyridin-3-yl)methyl]-6-[2-(piperidin-4-yl)-1H-pyrrolo[2,3-b]pyridin-4-yl]-1H-benzimidazole;

1-[(5-fluoropyridin-3-yl)methyl]-6-{2-[1-(methylsulfonyl)piperidin-4-yl]-1H-pyrrolo[2,3-b]pyridin-4-yl}-1H-benzimidazole;

1-(3-fluorobenzyl)-6-[2-(1,2,3,6-tetrahydropyridin-4-yl)-1H-pyrrolo[2,3-b]pyridin-4-yl]-1H-benzimidazole;

1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole;

4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide;

3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol;

5-fluoro-6-[2-(piperidin-4-yl)-1H-pyrrolo[2,3-b]pyridin-4-yl]-1-(tetrahydro-2H-pyran-4-ylmethyl)-1H-benzimidazole;

3-(4-{4-[5-fluoro-1-(tetrahydro-2H-pyran-4-ylmethyl)-1H-benzimidazol-6-yl]-1H-pyrrolo[2,3-b]pyridin-2-yl]piperidin-1-yl)propane-1,2-diol;

4-{4-[5-fluoro-1-(tetrahydro-2H-pyran-4-ylmethyl)-1H-benzimidazol-6-yl]-1H-pyrrolo[2,3-b]pyridin-2-yl}-N-methylpiperidine-1-carboxamide;

1-(4-{4-[5-fluoro-1-(tetrahydro-2H-pyran-4-ylmethyl)-1H-benzimidazol-6-yl]-1H-pyrrolo[2,3-b]pyridin-2-yl]piperidin-1-yl)-2-hydroxyethanone;

5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

4-{4-[1-(3-fluorobenzyl)-1H-benzimidazol-6-yl]-1H-pyrrolo[2,3-b]pyridin-2-yl]-N-methyl-3,6-dihydropyridine-1(2H)-carboxamide;

3-[4-{4-[1-(3-fluorobenzyl)-1H-benzimidazol-6-yl]-1H-pyrrolo[2,3-b]pyridin-2-yl}-3,6-dihydropyridin-1(2H)-yl]propane-1,2-diol;

N-(4-{[4-{4-[1-(3-fluorobenzyl)-1H-benzimidazol-6-yl]-1H-pyrrolo[2,3-b]pyridin-2-yl}-3,6-dihydropyridin-1(2H)-yl]methyl}phenyl)acetamide;

5-chloro-6-[2-(piperidin-4-yl)-1H-pyrrolo[2,3-b]pyridin-4-yl]-1-(tetrahydro-2H-pyran-4-ylmethyl)-1H-benzimidazole;

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine-3-carbonitrile;

1-(3-fluorobenzyl)-6-[2-(piperidin-4-yl)-1H-pyrrolo[2,3-b]pyridin-4-yl]-1H-pyrrolo[3,2-b]pyridine;

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine;

1-[2-(3-fluorophenyl)ethyl]-6-[2-(piperidin-4-yl)-1H-pyrrolo[2,3-b]pyridin-4-yl]-1H-benzotriazole;

6-[3-chloro-2-(piperidin-4-yl)-1H-pyrrolo[2,3-b]pyridin-4-yl]-1-[2-(3-fluorophenyl)ethyl]-1H-benzotriazole;

1-(3-fluorobenzyl)-6-{2-[1-(methylsulfonyl)piperidin-4-yl]-1H-pyrrolo[2,3-b]pyridin-4-yl}-1H-pyrrolo[3,2-b]pyridine;

1'-(3-fluorobenzyl)-2-(piperidin-4-yl)-1H,1'H-4,6'-bipyrrolo[2,3-b]pyridine-3'-carbonitrile;

1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole;

1-[(5-fluoropyridin-3-yl)methyl]-6-[2-(piperidin-4-yl)-1H-pyrrolo[2,3-b]pyridin-4-yl]-1H-pyrrolo[3,2-b]pyridine;

2-hydroxy-1-[4-{4-[1-(tetrahydro-2H-pyran-4-ylmethyl)-1H-benzotriazol-6-yl]-1H-pyrrolo[2,3-b]pyridin-2-yl}-3,6-dihydropyridin-1(2H)-yl]ethanone;

6-{2-[1-(methylsulfonyl)-1,2,3,6-tetrahydropyridin-4-yl]-1H-pyrrolo[2,3-b]pyridin-4-yl}-1-(tetrahydro-2H-pyran-4-ylmethyl)-1H-benzotriazole;

1-(3-fluorobenzyl)-6-[2-(1,2,3,6-tetrahydropyridin-4-yl)-1H-pyrrolo[2,3-b]pyridin-4-yl]-1H-pyrrolo[3,2-b]pyridine;

methyl 5-fluoro-1-(3-fluorobenzyl)-6-[2-(piperidin-4-yl)-1H-pyrrolo[2,3-b]pyridin-4-yl]-1H-indole-3-carboximidate;

5-fluoro-1-(3-fluorobenzyl)-6-[2-(piperidin-4-yl)-1H-pyrrolo[2,3-b]pyridin-4-yl]-1H-indole-3-carbonitrile;

1'-(3-fluorobenzyl)-2-(piperidin-4-yl)-1H,1'H-4,6'-bipyrrolo[2,3-b]pyridine;

2-(piperidin-4-yl)-1'-(tetrahydro-2H-pyran-4-ylmethyl)-1H,1'H-4,6'-bipyrrolo[2,3-b]pyridine;

4-{4-[1-(3-fluorobenzyl)-1H-pyrrolo[3,2-b]pyridin-6-yl]-1H-pyrrolo[2,3-b]pyridin-2-yl]-N-methylpiperidine-1-carboxamide;

6-{2-[1-(methylsulfonyl)piperidin-4-yl]-1H-pyrrolo[2,3-b]pyridin-4-yl}-1-(tetrahydro-2H-pyran-4-ylmethyl)-1H-pyrrolo[3,2-b]pyridine;

4-(4-{1-[(5-fluoropyridin-3-yl)methyl]-1H-pyrrolo[3,2-b]pyridin-6-yl}-1H-pyrrolo[2,3-b]pyridin-2-yl)-N-methylpiperidine-1-carboxamide;

1-[(5-fluoropyridin-3-yl)methyl]-6-{2-[1-(methylsulfonyl)piperidin-4-yl]-1H-pyrrolo[2,3-b]pyridin-4-yl}-1H-pyrrolo[3,2-b]pyridine;

1'-[(5-fluoropyridin-3-yl)methyl]-2-(piperidin-4-yl)-1H,1'H-4,6'-bipyrrolo[2,3-b]pyridine;

1-[(5-fluoropyridin-3-yl)methyl]-6-[2-(1,2,3,6-tetrahydropyridin-4-yl)-1H-pyrrolo[2,3-b]pyridin-4-yl]-1H-pyrrolo[3,2-b]pyridine;

1'-[(5-fluoropyridin-3-yl)methyl]-2-(1,2,3,6-tetrahydropyridin-4-yl)-1H,1'H-4,6'-bipyrrolo[2,3-b]pyridine;

4-{1'-[(5-fluoropyridin-3-yl)methyl]-1H,1'H-4,6'-bipyrrolo[2,3-b]pyridin-2-yl}-N-methylpiperidine-1-carboxamide;

1'-[(5-fluoropyridin-3-yl)methyl]-2-[1-(methylsulfonyl)piperidin-4-yl]-1H,1'H-4,6'-bipyrrolo[2,3-b]pyridine;

4-{1'[(5-fluoropyridin-3-yl)methyl]-1H,1'H-4,6'-bipyrrolo[2,3-b]pyridin-2-yl}-N-methyl-3,6-dihydropyridine-1(2H)-carboxamide;

1'-[(5-fluoropyridin-3-yl)methyl]-2-[1-(methylsulfonyl)-1,2,3,6-tetrahydropyridin-4-yl]-1H,1'H-4,6'-bipyrrolo[2,3-b]pyridine; and pharmaceutically acceptable salts thereof.

Schemes

Compounds of the present invention (e.g., compounds of Formula I) can be prepared by applying synthetic methodology known in the art and synthetic methodology outlined in the schemes set forth below.

Scheme 1

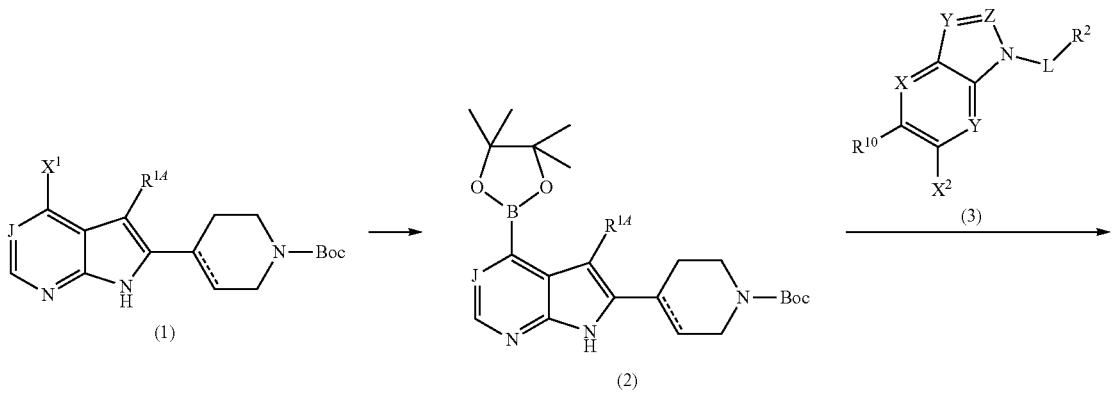

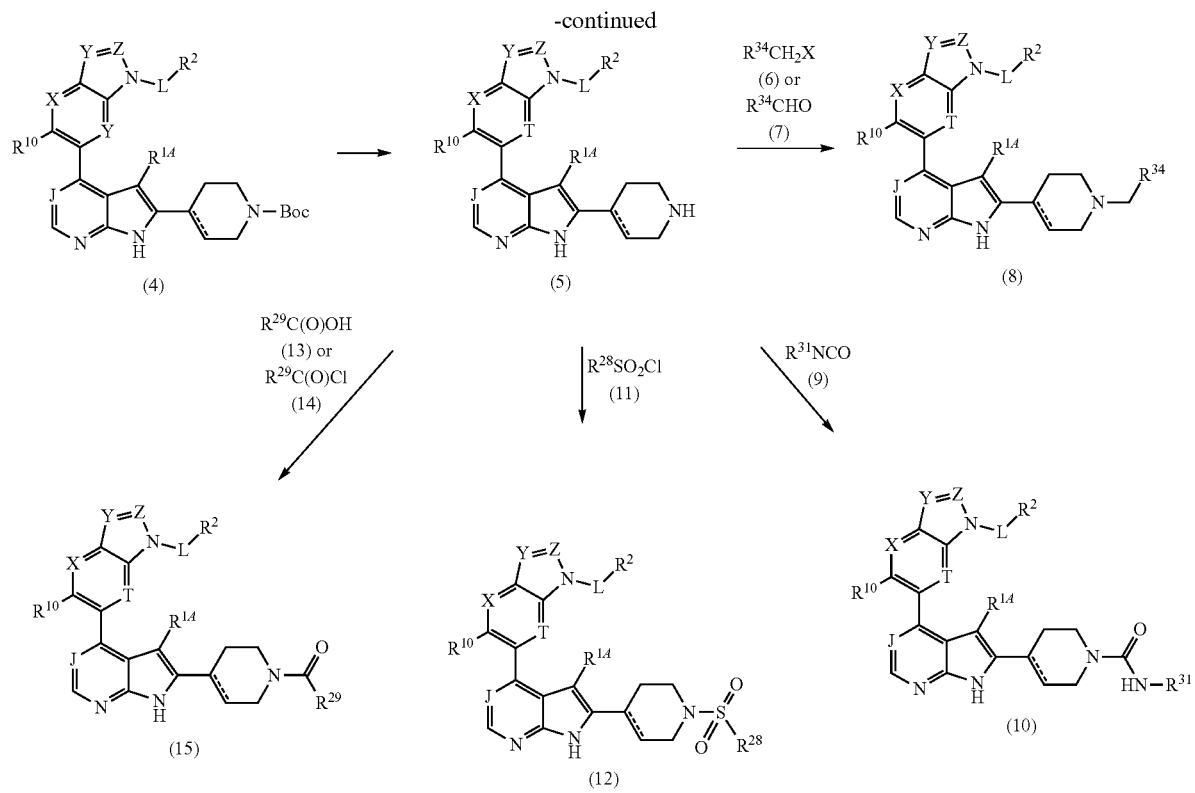

As shown in Scheme 1, compounds of formula (2), wherein $R^{1A}$ is as described herein, J is N or CH, and ⇌ is a single or double bond; can be prepared from compounds of formula (I), wherein $X^1$ is Cl or Br, by reacting the latter with 4,4,4',4',5,5,5',5'-octamethyl-2,2'-bi(1,3,2-dioxaborolane) under Suzuki coupling reaction conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation. Examples of the palladium catalyst include, but are not limited to, tetrakis(triphenylphosphine)palladium(0), tris(dibenzylideneacetone)dipalladium(0), bis(triphenylphosphine)palladium(II)dichloride, and palladium(II) acetate. Examples of suitable bases that may be employed include, but are not limited to, carbonates or phosphates of sodium, potassium, and cesium, acetates of sodium or potassium, and cesium fluoride. Examples of suitable ligands include, but are not limited to, 2-(dicyclohexylphosphino) biphenyl, 1,3,5,7-tetramethyl-6-phenyl-2,4,8-trioxa-6-phosphaadamante, 2-dicyclohexylphosphino-2',4',6'-triisopropylbiphenyl-X-phos), and 1,1'-bis(diphenylphosphanyl) ferrocene. Non-limiting examples of suitable solvent include methanol, ethanol, dimethoxyethane, N,N-dimethylformamide, dimethylsulfoxide, dioxane, tetrahydropyran, and water, or mixtures thereof. Compounds of formula (2) can be reacted with compounds of formula (3) wherein $R^{10}$, Y, L, and $R^2$ are as described herein for Formula (Ia), and $X^2$ is an appropriate halide or triflate; under Suzuki coupling reaction conditions described herein; to provide compounds of formula (4). Compounds of formula (5) can be prepared by deprotecting compounds of formula (4) under conditions described herein (e.g. with an acid such as hydrochloric acid in a solvent such as dioxane, ethanol or ethyl acetate or trifluoroacetic acid in a solvent such as dichloromethane). Compounds of formula (8), which are representative of compounds of Formula (Ia) and wherein $R^{34}$ is as described herein in Formula (Ia), can be prepared by reacting compounds of formula (5) with compounds of formula (6) or (7) under appropriate alkylation conditions. Compounds of formula (10), which are representative of compounds of Formula (Ia) and wherein $R^{31}$ is as described herein in Formula (Ia), can be prepared by reacting compounds of formula (5) with compounds of formula (9) under appropriate urea formation conditions. Compounds of formula (12), which are representative of compounds of Formula (Ia) and wherein $R^{28}$ is as described herein, can be prepared by reacting compounds of formula (5) with compounds of formula (11) under appropriate sulfonamidation conditions. Compounds of formula (15), which are representative of compounds of Formula (Ia) and wherein $R^{29}$ is as described herein in Formula (Ia), can be prepared by reacting compounds of formula (5) with compounds of formula (13) or (14) under appropriate acylation conditions.

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled.

Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of formula I. In certain embodiments, the compound of formula I may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 µg/kg to 100 mg/kg for a typical subject.

For administration, compounds of the formula I can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of formula I may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of formula I, or pharmaceutically acceptable salts thereof, and pharmaceutical compositions comprising a compound of formula I, or a pharmaceutically acceptable salt thereof, can be administered to a subject suffering from a CDK9-mediated disorder or condition. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of formula I can be administered by injection, that is, intravenously, intramuscularly, intracutaneously, subcutaneously, intraduodenally, parentally, or intraperitoneally. In certain embodiments, a compound of formula I may be administered orally. Also, the compounds described herein can be administered by inhalation, for example, intranasally. Additionally, the compounds of formula I can be administered transdermally, topically, via implantation, transdermally, topically, and via implantation. In certain embodiments, the compounds of the formula I may be delivered orally. The compounds can also be delivered rectally, bucally, intravaginally, ocularly, andially, or by insufflation. CDK9-mediated disorders and conditions can be treated prophylactically, acutely, and chronically using compounds of formula I, depending on the nature of the disorder or condition. Typically, the host or subject in each of these methods is human, although other mammals can also benefit from the administration of a compound of formula I.

The compounds of formula I can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benoyl)-4-(((1R)-3-(morpholin-4-yl)-1-((phenylsulfanyl)methyl)propyl)amino)-3-((trifluoromethyl)sulfonyl)benzenesulfonamide) (ABT-263), GX-070 (obatoclax), ABT-199, and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERA-MAXX® (deracoxib), JTE-522, 4-methyl-2-(3,4-dimethylphenyl)-1-(4-sulfamoylphenyl-1H-pyrrole),
MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 bifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI- 504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The following Examples may be used for illustrative purposes and should not be deemed to narrow the scope of the invention.

EXAMPLES

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

4-[1-(3-fluorobenzyl)-2,3-dihydro-1H-indol-6-yl]-2-(piperidin-4-yl)-1H-pyrrolo[2,3-b]pyridine

Example 1A tert-butyl (4-chloro-3-iodopyridin-2-yl)carbamate

To a solution of tert-butyl (4-chloropyridin-2-yl)carbamate (10 g, 43.7 mmol) and tetramethylethylenediamine (12 mL) in tetrahydrofuran (200 mL) at −70° C. was added 2.5M n-butyl lithium in hexane (52 mL, 131 mmol) over 30 minutes. The mixture was stirred at −70° C. for 1 hour and treated with a solution of iodine (27 g, 109 mmol) in 100 mL tetrahydrofuran at −70° C. The mixture was stirred at −70° C. for 30 minutes and warmed to room temperature. Saturated aqueous sodium hydrogen sulfite (200 mL) was added and the mixture stirred for 30 minutes. The mixture was extracted with ethyl acetate and the organic layers were washed with water and brine, dried over sodium sulfate, filtered, concentrated and precipitated from ethyl acetate/hexane to afford the title compound. LCMS: 298.9 (M+H—NCOOH)$^+$.

Example 1B tert-butyl 4-(hydroxymethyl)piperidine-1-carboxylate

To a solution of piperidin-4-ylmethanol (5 g, 43.4 mmol) in dichloromethane (100 mL) was added di-tert-butyldicarbonate (11.09 mL, 47.8 mmol) at 0° C. and the mixture was stirred at room temperature for 12 hours. After concentration, the residue was purified by column chromatography on silica gel (Isco®, Redi-Sep® column), eluting with 40% ethyl acetate in hexane to afford the title compound.

Example 1C tert-butyl 4-formylpiperidine-1-carboxylate

To a solution of Example 1B (5 g, 23.22 mmol) in dichloromethane (50 mL) was added pyridinium chlorochromate (10.01 g, 46.4 mmol) and the mixture stirred for 12 hours. The mixture was filtered through diatomaceous earth with dichloromethane, concentrated and purified by column chromatography on silica gel (Isco®, Redi-Sep® column), eluting with 40% ethyl acetate in hexane to afford the title compound. LCMS: 213.9 (M+H)$^+$.

Example 1D tert-butyl 4-ethynylpiperidine-1-carboxylate

To a solution of Example 1C (1 g, 4.69 mmol) in methanol (20 mL) was added potassium carbonate (3.89 g, 28.1 mmol) and the mixture was stirred for 30 minutes. Dimethyl 1-diazo-2-oxopropylphosphonate (3.60 g, 18.76 mmol) was added and the mixture was stirred for 12 hours. The mixture was filtered through diatomaceous earth with methanol, concentrated and purified by column chromatography on silica gel (Isco®, Redi-Sep® column), eluting with 15% ethyl acetate in hexane to afford the title compound. LCMS: 110 (M+H-Boc)$^+$.

Example 1E tert-butyl 4-((2-((tert-butoxycarbonyl)amino)-4-chloropyridin-3-yl)ethynyl)piperidine-1-carboxylate To a degassed solution of Example 1A (2.033 g, 5.73 mmol) in tetrahydrofuran (15 mL) was added copper (I) iodide (46 mg, 0.239 mmol) and bis(triphenylphosphine)palladium(II) chloride (168 mg, 0.239 mmol) followed by triethyl amine (1.998 mL, 14.33 mmol) and Example 1D (1 g, 4.78 mmol). The mixture was stirred for 12 hours at room temperature and filtered through diatomaceous earth with ethyl acetate. The mixture was washed with water and brine, dried over sodium sulfate, filtered and concentrated. The residue was purified by column chromatography on silica gel (Isco®, Redi-Sep® column), eluting with 15% ethyl acetate in hexane to afford the title compound. LCMS: 335.9 (M+H-Boc)$^+$.

Example 1F tert-butyl 4-(4-chloro-1H-pyrrolo[2,3-b]pyridin-2-yl)piperidine-1-carboxylate To a solution of product of Example 1E (800 mg, 1.83 mmol) in toluene (5 mL) was added potassium tert-butoxide (515 mg, 4.59 mmol) and 18-crown-6 (48 mg, 0.182 mmol) and the mixture was heated at 65° C. for 12 hours. The mixture was dissolved in ethyl acetate, washed with water and brine, dried over sodium sulfate, filtered and concentrated. The residue was purified by column chromatography on silica gel (Isco®, Redi-Sep® column), eluting with 40% ethyl acetate in hexane to afford the title compound. LCMS: 335.8 (M+H)$^+$.

Example 1G 6-bromo-1-(3-fluorobenzyl)indoline

A mixture of 6-bromoindoline (750 mg, 3.79 mmol), 1-(bromomethyl)-3-fluorobenzene (697 pt, 5.68 mmol) and cesium carbonate (1.851 g, 5.68 mmol) in N,N-dimethylformamide (7.573 mL) was stirred at 110° C. for 2 hours. The mixture was cooled, diluted with 100 mL ethyl acetate, washed with water and brine, dried over magnesium sulfate, filtered and concentrated. Purification by silica gel flash chromatography (Isco®, Redi-Sep® column), eluting with a gradient of 2-50% ethyl acetate/hexane, afforded the title compound. LCMS: 306 (M+H)$^+$.

Example 1H

4-[1-(3-fluorobenzyl)-2,3-dihydro-1H-indol-6-yl]-2-(piperidin-4-yl)-1H-pyrrolo[2,3-b]pyridine A mixture of tris(dibenzylideneacetone)dipalladium(0) (40.9 mg, 0.045 mmol), 2-(dicyclohexylphosphino)-2',4',6'-triisopropylbiphenyl (170 mg, 0.357 mmol), bis(pinacolato) diboron (454 mg, 1.787 mmol), potassium acetate (351 mg, 3.57 mmol) and Example 1F (600 mg, 1.787 mmol) was flushed with nitrogen and 1,4-dioxane (7.147 mL) was added via syringe under nitrogen. After stirring at 110° C. for 3 hours, a solution of Example 1G (422 mg, 1.379 mmol) in 0.25 mL 1,4-dioxane followed by 5M aqueous potassium phosphate (0.25 mL) were added and the mixture was heated at 110° C. for 3 hours. After cooling, the mixture was filtered through diatomaceous earth with ethyl acetate, concentrated and purified by silica gel flash chromatography (Isco®, Redi-Sep® column), eluting with a gradient of 10-100% ethyl acetate/hexane, to give the BOC-protected intermediate. To a solution of this intermediate in 4 mL dichloromethane was added 4 mL trifluoroacetic acid and the mixture was stirred at ambient temperature for 10 minutes. After concentration, the crude trifluoroacetate salt was dissolved in 50 mL ethyl acetate and washed with 10% aqueous potassium carbonate (40 mL). The aqueous layer was washed with ethyl acetate and the organic extracts were washed with brine, dried over magnesium sulfate, filtered and concentrated. Purification by silica gel flash chromatography (Isco®, Redi-Sep® column), eluting with a gradient of 2-60% 2:1 methanol/water in ethyl acetate with 2% triethylamine added, afforded the title compound.
$^1$H NMR (300 MHz, methanol-d$_4$) δ 8.12 (d, J=5.1, 1H), 7.43-7.30 (m, 1H), 7.26-7.12 (m, 3H), 7.09 (d, J=5.1, 1H), 7.05-6.95 (m, 2H), 6.77 (d, J=1.2, 1H), 6.29 (s, 1H), 4.34 (s, 2H), 3.55-3.39 (m, 3H), 3.26-2.94 (m, 6H), 2.35-2.19 (m, 2H), 1.99-1.83 (m, 2H). MS (ESI) m/e 427.5 (M+H)$^+$.

Example 2

1-(3-fluorobenzyl)-6-[2-(piperidin-4-yl)-1H-pyrrolo[2,3-b]pyridin-4-yl]-1H-benzimidazole Example 2A 5-bromo-N-(3-fluorobenzyl)-2-nitroaniline A mixture of 4-bromo-2-fluoro-1-nitrobenzene (500 mg, 2.273 mmol) and 3-fluorobenzylamine (370 mg, 2.95 mmol)

in N,N-dimethylformamide (7 mL) was treated with potassium carbonate (1.00 g, 7.24 mmol) and heated at 80° C. for 1 hour. The mixture was diluted with ethyl acetate, washed with brine, dried over magnesium sulfate, filtered and concentrated to give the crude title compound which was used without further purification.

Example 2B 5-bromo-N1-(3-fluorobenzyl)benzene-1,2-diamine

To suspension of Example 2A (700 mg, 2.153 mmol) in methanol (10 mL) was added hydrazine monohydrate (0.2 mL, 4.08 mmol) followed by 50% Raney® nickel in water (100 mg). The mixture was stirred at 50° C. for 2 hours, filtered through diatomaceous earth with dichloromethane and concentrated. Purification by flash chromatography (Isco®, Redi-Sep® column) eluting with 100% dichloromethane gave the title compound.

Example 2C 6-bromo-1-(3-fluorobenzyl)-1H-benzo[d]imidazole

A mixture of Example 2B (299 mg, 1.013 mmol) in formic acid (500 μL, 13.25 mmol) was stirred at 90° C. for 1 hour. The cooled mixture was diluted with ethyl acetate, washed with water and brine, dried over magnesium sulfate, filtered and concentrated. Purification by silica gel flash chromatography (Isco®, Redi-Sep® column) eluting with 80% ethyl acetate/hexane afforded the title compound. MS (ESI) m/e 306 (M+H)$^+$.

Example 2D 1-(3-fluorobenzyl)-6-[2-(piperidin-4-yl)-1H-pyrrolo[2,3-b]pyridin-4-yl]-1H-benzimidazole The title compound was prepared as described in Example 1H, using Example 2C in place of Example 1G. Purification by silica gel flash chromatography (Isco®, Redi-Sep® column) eluting with a gradient of 50-100% ethyl acetate in hexane, then 10% 2:1 methanol/water in ethyl acetate, followed by further purification by reverse-phase HPLC (Phenomenex Luna C8 AXIA column, 100 Å) eluting with a gradient of 10-95% acetonitrile/0.1% trifluoroacetic acid in water gave the BOC-protected intermediate. The intermediate was dissolved in 0.5 mL ethyl acetate and 5 mL 2M hydrogen chloride in diethyl ether was added. The mixture was stirred at 50° C. for 2 hours. After cooling, the mixture was filtered, washed with 5 mL diethyl ether and dried under vacuum to give the title compound as the bis-hydrochloride salt. $^1$H NMR (400 MHz, methanol-d$_4$) δ 9.73 (s, 1H), 8.46 (d, J=6.2, 1H), 8.30 (s, 1H), 8.15 (s, 2H), 7.72 (d, J=6.2, 1H), 7.55-7.42 (m, 1H), 7.38-7.31 (m, 2H), 7.25-7.12 (m, 1H), 6.71 (s, 1H), 5.96 (s, 2H), 3.61-3.51 (m, 2H), 3.39-3.32 (m, 1H), 3.29-3.20 (m, 2H), 2.42-2.31 (m, 2H), 2.18-2.02 (m, 2H). MS (ESI) m/e 426.4 (M+H)$^+$.

Example 3

1-benzyl-6-[2-(piperidin-4-yl)-1H-pyrrolo[2,3-b]pyridin-4-yl]-1H-indole-3-carbonitrile Example 3A benzyl-6-bromo-1H-indole-3-carbonitrile A solution of 6-bromo-1H-indole-3-carbonitrile (400 mg, 1.81 mmol), 2-(tributylphosphoranylidene)acetonitrile (655 mg, 2.71 mmol) and benzyl alcohol (282 μL, 2.71 mmol) in toluene (5 mL) was heated at 75° C. overnight and concentrated. The residue was purified by flash chromatography on silica (IntelliFlash Varian 971-FP), eluting with 30% heptanes in ethyl acetate to provide the title compound. LCMS: 312.4 (M+H)$^+$.

Example 3B tert-butyl 4-(4-(1-benzyl-3-cyano-1H-indol-6-yl)-1H-pyrrolo[2,3-b]pyridin-2-yl)piperidine-1-carboxylate A mixture of Example 3A (420 mg, 1.350 mmol), 4,4,4',4',5,5,5',5'-octamethyl-2,2'-bi(1,3,2-dioxaborolane) (377 mg, 1.485 mmol) and potassium acetate (397 mg, 4.05 mmol) in dioxane (5 mL) were flushed with nitrogen and 1,1'-bis(diphenylphosphino)ferrocene-palladium(II)dichloride dichloromethane complex (66.1 mg, 0.08 mmol) was added. The mixture was stirred at 100° C. overnight, cooled and Example 1F (0.42 g, 1.25 mmol), tricyclohexylphosphine (0.023 g, 0.10 mmol), bis(triphenylphosphine)palladium(II) dichloride (0.07 g, 0.10 mmol), cesium carbonate (0.815 g, 2.50 mmol), 1M aqueous sodium carbonate (1 mL) and 2 mL dioxane were added. The mixture was stirred at 100° C. overnight, filtered and concentrated. The residue was purified by flash chromatography on silica (IntelliFlash Varian 971-FP), eluting with a gradient of 45-80% ethyl acetate in heptanes to provide the title compound. LCMS: 532.2 (M+H)$^+$.

Example 3C 1-benzyl-6-(2-(piperidin-4-yl)-1H-pyrrolo[2,3-b]pyridin-4-yl)-1H-indole-3-carbonitrile A solution of Example 3B (400 mg, 0.75 mmol) in dichloromethane (10 mL) was treated with trifluoroacetic acid (3 mL) for 30 minutes and concentrated. The residue was purified by reverse phase chromatography (IntelliFlash Varian 971-FP, Grace Reveleris C18 column), eluting with a gradient of 10-70% acetonitrile/0.1% trifluoroacetic acid in water to provide the title compound as the trifluoroacetate salt. $^1$H NMR (400 MHz, dimethylsulfoxide-d$_6$) δ 1.67-1.86 (m, 2 H) 2.21 (d, 2 H) 2.99-3.16 (m, 3 H) 3.41 (d, 2 H) 5.64 (s, 2 H) 6.16 (s, 1 H) 7.20 (d, 1 H) 7.29-7.34 (m, 3 H) 7.34-7.42 (m, 2 H) 7.61-7.71 (m, 1 H) 7.83 (d, 1 H) 7.96 (s, 1 H) 8.24 (d, 1 H) 8.31-8.45 (m, 1 H) 8.60 (s, 1 H) 8.70 (d, 1 H) 11.87 (s, 1 H). LCMS: 431.7 (M+H)$^+$.

Example 4

1-(3-fluorobenzyl)-6-{2-[1-(methylsulfonyl)piperidin-4-yl]-1H-pyrrolo[2,3-b]pyridin-4-yl}-1H-benzimidazole To a suspension of Example 2D (260 mg, 0.486 mmol) in N,N-dimethylformamide (2.43 mL) was added N,N-diisopropylethylamine (509 μL, 2.92 mmol) followed by methanesulfonyl chloride (56.8 μL, 0.729 mmol) and the mixture was stirred at ambient temperature for 2 hours. To the slurry was added 7.5 mL water, 0.5 mL 10% aqueous potassium carbonate and 2.5 mL diethy ether and the mixture was stirred for 30 minutes and filtered. The solid was washed with water and heptanes and dried under vacuum at 50° C. for 16 hours to give the title compound. $^1$H NMR (300 MHz, dimethylsulfoxide-d$_6$) δ 11.69 (s, 1H), 8.53 (s, 1H), 8.19 (d, J=4.9, 1H), 7.88-7.76 (m, 2H), 7.57 (dd, J=8.3, 1.6, 1H), 7.48-7.34 (m, 1H), 7.26-7.09 (m, 4H), 6.10 (s, 1H), 5.63 (s, 2H), 3.73-3.65 (m, 2H), 2.91 (s, 3H), 2.90-2.80 (m, 3H), 2.12-2.02 (m, 2H), 1.81-1.64 (m, 2H). MS (ESI) m/e 504.4 (M+H)$^+$.

Example 5

6-{2-(piperidin-4-yl)-1H-pyrrolo[2,3-b]pyridin-4-yl}-1-(tetrahydro-2H-pyran-4-ylmethyl)-1H-benzimidazole

Example 5A 5-bromo-2-nitro-N-((tetrahydro-2H-pyran-4-yl)methyl)aniline

A mixture of 4-bromo-2-fluoro-1-nitrobenzene (6.5 g, 29.5 mmol), (tetrahydro-2H-pyran-4-yl)methanamine (4.25 g, 36.9 mmol) and potassium carbonate (16.33 g, 118 mmol) in N,N-dimethylformamide (130 mL) was heated at 80° C. for 1 hour. After cooling, the mixture was diluted with 400 mL ethyl acetate. The mixture was washed with water and brine, dried over magnesium sulfate, filtered and concentrated to give the crude title compound which was used without further purification.

Example 5B 5-bromo-N1-((tetrahydro-2H-pyran-4-yl)methyl)benzene-1,2-diamine

Example 5A (9.30 g, 29.5 mmol) was suspended in methanol (150 mL) and hydrazine hydrate (5 g, 100 mmol) was added, followed by 50% Raney® nickel in water (1.00 g, 5.84 mmol) and the mixture was heated at 50° C. for 1 hour. After cooling, diatomaceous earth was added and the slurry was filtered through diatomaceous earth with dichloromethane. Concentration provided the crude title compound which was used without further purification. MS (ESI) m/z 287.2 (M+H)$^+$.

Example 5C 6-bromo-1-((tetrahydro-2H-pyran-4-yl)methyl)-1H-benzo[d]imidazole A solution of the crude product of Example 5B (8.41 g, 29.5 mmol) in formic acid (10 mL, 261 mmol) was heated at 95° C. for 1 hour. After cooling, the mixture was concentrated and dissolved in ethyl acetate. The mixture was washed with 10% aqueous potassium carbonate and brine, dried over magnesium sulfate, filtered and concentrated. Purification by silica gel flash chromatography (Isco®, Redi-Sep® column) eluting with a gradient of 50-100% ethyl acetate/hexane then 10% 2:1 methanol/water in ethyl acetate, followed by recrystallization from ethyl acetate/hexane, afforded the title compound. MS (ESI) m/z 297 (M+H)$^+$.

Example 5D

6-{2-(piperidin-4-yl)-1H-pyrrolo[2,3-b]pyridin-4-yl}-1-(tetrahydro-2H-pyran-4-ylmethyl)-1H-benzimidazole A mixture of tris(diberizylideneacetone)dipalladium(0) (0.170 g, 0.186 mmol), 2-(dicyclohexylphosphino)-2',4',6'-triisopropylbiphenyl (0.355 g, 0.744 mmol), bis(pinacolato) diboron (0.945 g, 3.72 mmol), potassium acetate (0.731 g, 7.44 mmol) and Example 1F (1.25 g, 3.72 mmol) was flushed with nitrogen and 1,4-dioxane (14.89 ml) was added via syringe under nitrogen. After stirring at 110° C. for 3 hours, a solution of Example 5C (1.099 g, 3.72 mmol) in 0.5 mL dioxane was added, followed by 5M aqueous potassium phosphate (3.72 mL, 18.61 mmol) and the mixture was heated at 110° C. for 3 hours. After cooling, the mixture was filtered through diatomaceous earth with ethyl acetate and concentrated. The residue was purified by silica gel flash chromatography (Isco®, Redi-Sep® column) eluting with a gradient of 50-100% ethyl acetate/hexane then 10% 2:1 methanol/water in ethyl acetate, to give the BOC-protected intermediate. A solution of this intermediate in 4 mL 1:1 methanol/dichloromethane was cooled to 0° C. and 8 mL 2M hydrogen chloride in diethyl ether was added. After stirring at ambient temperature for 2 hours, methanol (3 mL) was added and the mixture was concentrated and dried under vacuum to obtain the title compound as the bis-hydrochloride salt. $^1$H NMR (400 MHz, methanol-d$_4$) δ 9.68 (s, 1H), 8.54 (s, 1H), 8.48 (d, J=6.2, 1H), 8.21-8.08 (m, 2H), 7.80 (d, J=6.2, 1H), 6.87 (s, 1H), 4.62 (d, J=7.4, 2H), 3.99-3.91 (m, 2H), 3.61-3.52 (m, 2H), 3.47-3.36 (m, 3H), 3.29-3.17 (m, 2H), 2.45-2.31 (m, 3H), 2.20-2.04 (m, 2H), 1.66-1.44 (m, 4H). MS (ESI) m/z 416.4 (M+H)$^+$.

Example 6

6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole To a solution of Example 5D (200 mg, 0.381 mmol) in N,N-dimethylformamide (1.524 mL) at 0° C. was added triethylamine (319 µL, 2.286 mmol) followed by methanesulfonyl chloride (44.5 µL, 0.572 mmol) and the mixture was stirred at ambient temperature for 1 hour. Trifluoroacetic acid (0.1 mL) was added followed by methanol (1 mL). Purification by reverse-phase HPLC (Phenomenex Luna C8 AXIA column, 100 Å) eluting with a gradient of 10-95% acetonitrile/0.1% trifluoroacetic acid in water gave the title compound as the trifluoroacetate salt. The material was dissolved in methanol and loaded on a Bond Elut® MEGA BE-SCX (5 GM) cartridge (pre-washed with 30 mL 50% methanol in dichloromethane) and washed with methanol, followed by 2M ammonia in methanol. After concentration, the product was further purified by silica gel flash chromatography (Isco®, Redi-Sep® column) eluting with a gradient of 50-100% ethyl acetate/hexane then 10% 2:1(methanol/water) in ethyl acetate to give the title compound. $^1$H NMR (300 MHz, dimethylsulfoxide-d$_6$) δ 11.71 (s, 1H), 8.30 (s, 1H), 8.22 (d, J=5.0, 1H), 7.99 (d, J=1.0, 1H), 7.79 (d, J=8.4, 1H), 7.60 (dd, J=8.4, 1.5, 1H), 7.22 (d, J=5.0, 1H), 6.42 (d, J=1.5, 1H), 4.25 (d, J=7.1, 2H), 3.89-3.79 (m, 2H), 3.72-3.61 (m, 2H), 3.29-3.17 (m, 2H), 2.95-2.79 (m, 5H), 2.22-2.04 (m, 3H), 1.86-1.65 (m, 2H), 1.49-1.23 (m, 4H). MS (ESI) m/z 493.9 (M+H)$^+$.

Example 7

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine

Example 7A 6-chloro-3-nitro-N-((tetrahydro-2H-pyran-4-yl)methyl)pyridin-2-amine A mixture of 2,6-dichloro-3-nitropyridine (1 g, 5.18 mmol)), (tetrahydro-2H-pyran-4-yl)methanamine (1.044 g, 9.07 mmol) and triethylamine (2.167 mL, 15.55 mmol) in tetrahydrofuran (22.83 mL) was stirred at 0° C. for 30 minutes and at ambient temperature for 2 hours. Methanol was added (10 mL) followed by silica gel and the mixture was concentrated and purified by silica gel flash chromatography (Isco®, Redi-Sep® column), eluting with a gradient of 2-30% ethyl acetate/hexane to afford the title compound. MS (ESI) m/z 272 (M+H)$^+$.

Example 7B 6-chloro-N2-((tetrahydro-2H-pyran-4-yl)methyl)pyridine-2,3-diamine

A solution of Example 7A (1.057 g, 3.89 mmol) in tetrahydrofuran (1 mL) was added to 50% Raney® nickel in water (335.5 mg, 5.72 mmol) in a pressure bottle. The mixture was stirred under 60 psi hydrogen at room temperature for 13 hours. The mixture was filtered through a polypropylene membrane and concentrated to give the crude title compound which was used without further purification.

Example 7C 5-chloro-3-((tetrahydro-2H-pyran-4-yl)methyl)-3H-imidazo[4,5-b]pyridine A solution of the crude product of Example 7B (0.979 g, 4.05 mmol) in formic acid (2 mL, 52.1 mmol) was heated at 95° C. for 1 hour. After cooling, the mixture was concentrated and dissolved in ethyl acetate. The mixture was washed with dilute potassium carbonate and brine, dried over magnesium sulfate, filtered and concentrated. Recrystallization from ethyl acetate/hexane afforded the title compound. MS (ESI) m/z 252 (M+H)$^+$.

Example 7D

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine The title compound was prepared as described in Example 5D using Example 7C in place of Example 5C. The mixture was filtered through diatomaceous earth with ethyl acetate and concentrated. Purification by silica gel flash chromatography (Isco®, Redi-Sep® column) eluting with a gradient of 50-100% ethyl acetate/hexane then 10% 2:1 methanol/water in ethyl acetate, followed by further purification by reverse-phase HPLC (Phenomenex Luna C8 AXIA column, 100 Å) eluting with a gradient of 10-95% acetonitrile/0.1% trifluoroacetic acid in water gave the BOC-intermediate. The intermediate was dissolved in methanol and loaded on a Bond Elut® MEGA BE-SCX (5 GM) cartridge (pre-washed with 30 mL 50% methanol in dichloromethane) and washed with methanol. The cartridge was washed with 2M ammonia in methanol and concentrated. The residue was dissolved in 1 mL methanol and 5 mL 2M hydrogen chloride in diethyl ether was added and the mixture stirred at 50° C. for 2 hours. After cooling, the mixture was concentrated to give the title compound as a bis-hydrochloride salt. $^1$H NMR (300 MHz, methanol-d$_4$) δ 8.48 (s, 1H), 8.25 (d, J=5.2, 1H), 8.20 (d, J=8.4, 1H), 8.02 (d, J=8.4, 1H), 7.63 (d, J=5.3, 1H), 6.95 (d, J=0.7, 1H), 4.38 (d, J=7.3, 2H), 4.01-3.89 (m, 2H), 3.46-3.33 (m, 4H), 3.20-2.95 (m, 3H), 2.48-2.25 (m, 3H), 1.99-1.80 (m, 2H), 1.64-1.40 (m, 4H). MS (ESI) m/z 417.1 (M+H)$^+$.

Example 8

1-(3-fluorobenzyl)-6-[2-(piperidin-4-yl)-1H-pyrrolo[2,3-b]pyridin-4-yl]-1H-indole-3-carbonitrile Example 8A 6-bromo-1-(3-fluorobenzyl)-1H-indole-3-carbonitrile The title compound was prepared using the procedure described in Example 3A using 3-fluorobenzyl alcohol in place of benzyl alcohol. LCMS: 330.8 (M+H)$^+$.

Example 8B tert-butyl 4-(4-(3-cyano-1-(3-fluorobenzyl)-1H-indol-6-yl)-1H-pyrrolo[2,3-b]pyridin-2-yl)piperidine-1-carboxylate The title compound was prepared using the procedure described in Example 3B using Example 8A in place of Example 3A. LCMS: 550.2 (M+H)$^+$.

Example 8C 1-(3-fluorobenzyl)-6-(2-(piperidin-4-yl)-1H-pyrrolo[2,3-b]pyridin-4-yl)-1H-indole-3-carbonitrile The title compound was prepared as the trifluoroacetate salt using the procedure described in Example 3C using Example 8B in place of Example 3B. $^1$H NMR (500 MHz, dimethylsulfoxide-d$_6$) δ 1.72-1.88 (m, 2 H) 2.22 (d, 2 H) 3.09 (q, 3 H) 3.42 (d, 2 H) 5.68 (s, 2 H) 6.20 (s, 1 H) 7.14 (d, 1 H) 7.16-7.22 (m, 2 H) 7.26 (d, 1 H) 7.43 (q, 1 H) 7.68 (d, 1 H) 7.86 (d, 1 H) 8.00 (s, 1 H) 8.29 (d, 1 H) 8.52 (d, 1 H) 8.62 (s, 1 H) 8.83 (d, 1 H) 12.04 (s, 1 H) LCMS: 450.1 (M+H)$^+$.

Example 9

4-[5-fluoro-1-(3-fluorobenzyl)-1H-indol-6-yl]-2-(piperidin-4-yl)-1H-pyrrolo[2,3-b]pyridine Example 9A 6-bromo-5-fluoro-1-(3-fluorobenzyl)-1H-indole The title compound was prepared using the procedure described in Example 3A using 3-fluorobenzyl alcohol and 6-bromo-5-fluoro-1H-indole in place of benzyl alcohol and 6-bromo-1H-indole-3-carbonitrile, respectively. LCMS: 323.8 (M+H)$^+$.

Example 9B tert-butyl 4-(4-(5-fluoro-1-(3-fluorobenzyl)-1H-indol-6-yl)-1H-pyrrolo[2,3-b]pyridin-2-yl)piperidine-1-carboxylate The title compound was prepared using the procedure described in Example 3B using Example 9A in place of Example 3A. LCMS: 543.2 (M+H)$^+$.

Example 9C 4-(5-fluoro-1-(3-fluorobenzyl)-1H-indol-6-yl)-2-(piperidin-4-yl)-1H-pyrrolo[2,3-b]pyridine The title compound was prepared as the trifluoroacetate salt using the procedure described in Example 3C using Example 9B in place of Example 3B. $^1$H NMR (500 MHz, dimethylsulfoxide-$d_6$) δ 1.68-1.80 (m, 2 H) 2.18 (d, 2 H) 3.06 (q, 3 H) 3.38 (d, 2 H) 5.53 (s, 2 H) 5.92 (s, 1 H) 6.60 (d, 1 H) 7.02 (d, 2 H) 7.09-7.14 (m, 2 H) 7.35-7.41 (m, 1 H) 7.54 (d, 1 H) 7.64 (d, 1 H) 7.73 (d, 1 H) 8.23 (d, 1 H) 8.38 (s, 1 H) 8.70 (s, 1 H) 11.83 (s, 1 H). LCMS: 443.1 (M+H)$^+$.

Example 10

6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile To a solution of Example 8C (100 mg, 0.22 mmol) in dichloromethane (5 mL) and methanol (0.5 mL) was added triethylamine (93 μL, 0.67 mmol), 2,3-dihydroxypropanal (200 mg, 2.22 mmol), acetic acid (63.7 μL, 1.11 mmol) and MP-cyanoborohydride (2.49 mmol/g, 358 mg, 0.89 mmol). The mixture was stirred overnight and filtered. The filtrate was concentrated and the residue was purified by reverse phase chromatography (IntelliFlash Varian 971-FP, Grace Reveleris C18 column), eluting with a gradient of 10-70% acetonitrile/0.1% trifluoroacetic acid in water to provide the title compound as the trifluoroacetate salt. $^1$H NMR (400 MHz, dimethylsulfoxide-$d_6$) δ 1.75-2.06 (m, 2 H) 2.15-2.35 (m, 2 H) 2.95-3.29 (m, 5 H) 3.29-3.52 (m, 3 H) 3.53-3.76 (m, 3 H) 5.66 (s, 2 H) 6.14 (s, 1 H) 7.04-7.24 (m, 4 H) 7.34-7.48 (m, 1 H) 7.67 (t, 1 H) 7.84 (d, 1 H) 7.98 (s, 1 H) 8.25 (d, 1 H) 8.61 (s, 1 H) 9.21 (s, 1 H) 11.85 (s, 1 H). LCMS: 524.1 (M+H)$^+$.

Example 11

1-(3-fluorobenzyl)-6-{2-[1-(methylsulfonyl)piperidin-4-yl]-1H-pyrrolo[2,3-b]pyridin-4-yl}-1H-indole-3-carbonitrile To a solution of Example 8C (200 mg, 0.29 mmol) and triethylamine (206 μL, 1.48 mmol) in dichloromethane (3 mL) at 0° C. was added methanesulfonyl chloride (34.28 μL, 0.45 mmol) dropwise. The mixture was stirred at room temperature for 10 minutes, quenched with ice-water and concentrated. The residue was purified by reverse phase chromatography (IntelliFlash Varian 971-FP, Grace Reveleris C18 column), eluting with a gradient of 10-70% acetonitrile/0.1% trifluoroacetic acid in water to provide the title compound as the trifluoroacetate salt. $^1$H NMR (500 MHz, dimethylsulfoxide-$d_6$) δ 1.66-1.78 (m, 2 H) 2.00-2.09 (m, 2 H) 2.82-2.90 (m, 3 H) 2.92 (s, 3 H) 3.48-3.77 (m, 2 H) 5.67 (s, 2 H) 6.11 (d, 1 H) 7.11 (d, 1 H) 7.14-7.25 (m, 3 H) 7.36-7.47 (m, 1 H) 7.66 (dd, 1 H) 7.84 (d, 1 H) 7.96 (s, 1 H) 8.24 (d, 1 H) 8.61 (s, 1 H) 11.90 (s, 1 H). LCMS: 528.1 (M+H)$^+$.

Example 12

1-[(5-fluoropyridin-3-yl)methyl]-6-[2-(piperidin-4-yl)-1H-pyrrolo[2,3-b]pyridin-4-yl]-1H-benzimidazole Example 12A 5-bromo-N-((5-fluoropyridin-3-yl)methyl)-2-nitroaniline A mixture of 4-bromo-2-fluoro-1-nitrobenzene (1.20 g, 5.45 mmol), (5-fluoropyridin-3-yl)methanamine (757 mg, 6.0 mmol) and potassium carbonate (3.015 g, 21.82 mmol) in N,N-dimethylformamide (8 mL) was heated at 80° C. for 1 hour. After cooling, the mixture was diluted with ethyl acetate and the mixture was washed with water and brine, dried over magnesium sulfate, filtered and concentrated to give the crude title compound which was used without further purification. MS (ESI) m/z 327 (M+H)$^+$.

Example 12B 5-bromo-N1-((5-fluoropyridin-3-yl)methyl)benzene-1,2-diamine

To a solution of Example 12A (1.777 g, 5.45 mmol) in methanol (30 mL) was added hydrazine hydrate (0.74 g, 15.26 mmol), followed by 50% Raney® nickel in water (200 mg) and the mixture was heated at 50° C. for 60 minutes. After cooling, diatomaceous earth was added and the slurry was filtered through diatomaceous earth with dichloromethane. Concentration provided the crude title compound which was used without further purification. MS (ESI) m/z 295.9 (M+H)$^+$.

Example 12C 6-bromo-1-((5-fluoropyridin-3-yl)methyl)-1H-benzo[d]imidazole

A solution of Example 12B (1.615 g, 5.45 mmol) in formic acid (4.53 mL, 120 mmol) was heated at 95° C. for 1 hour. After cooling, the mixture was concentrated and dissolved in ethyl acetate. The mixture was washed with 10% aqueous potassium carbonate and brine, dried over magnesium sulfate, filtered and concentrated. Purification by silica gel flash chromatography (Isco®, Redi-Sep® column) eluting with a gradient of 50-100% ethyl acetate/hexane then 10% 2:1 methanol/water in ethyl acetate, followed by recrystallization from ethyl acetate/hexane, afforded the title compound. MS (ESI) m/z 305.8 (M+H)$^+$.

Example 12D

1-[(5-fluoropyridin-3-yl)methyl]-6-[2-(piperidin-4-yl)-1H-pyrrolo[2,3-b]pyridin-4-yl]-1H-benzimidazole The title compound was prepared as described in Example 5D using Example 12C in place of Example 5C. The mixture was filtered through diatomaceous earth with ethyl acetate and concentrated. The residue was purified by silica gel flash chromatography (Isco®, Redi-Sep® column) eluting with a gradient of 50-100% ethyl acetate/hexane then 10% 2:1 methanol/water in ethyl acetate, followed by further purification by reverse-phase HPLC (Phenomenex Luna C8 AXIA column, 100 Å) eluting with a gradient of 10-95% acetonitrile/0.1% trifluoroacetic acid in water to give the BOC-protected intermediate. The intermediate was treated with 50% trifluoroacetic acid in dichloromethane (6 mL) and concentrated to give the title compound as the trifluoroacetate salt. A portion of this salt (120 mg) was dissolved in methanol and loaded on a Bond Elut® MEGA BE-SCX (5 GM) cartridge (pre-washed with 30 mL of 50% methanol in dichloromethane) and washed with methanol, followed by 2M ammonia in methanol and concentrated to give the title compound. $^1$H NMR (400 MHz, dimethylsulfoxide-$d_6$) δ 11.79 (s, 1H), 8.61-8.55 (m, 3H), 8.23 (d, J=5.0, 1H), 7.95 (d, J=1.1, 1H), 7.83 (d, J=8.4, 1H), 7.80-7.76 (m, 1H), 7.60 (dd, J=8.4, 1.6, 1H), 7.17 (d, J=5.0, 1H), 6.17 (d, J=1.4, 1H), 5.71 (s, 2H), 3.45-3.36 (m, 2H), 3.19-3.03 (m, 3H), 2.31-2.19 (m, 2H), 1.88-1.72 (m, 2H). MS (ESI) m/z 427.1 (M+H)$^+$.

Example 13

1-[(5-fluoropyridin-3-yl)methyl]-6-{2-[1-(methylsulfonyl)piperidin-4-yl]-1H-pyrrolo[2,3-b]pyridin-4-yl}-1H-benzimidazole The title compound was prepared as described in Example 6 using Example 12D in place of Example 5. Trifluoroacetic acid (0.1 mL) was added, followed by methanol (1 mL), and the mixture was purified by reverse-phase HPLC (Phenomenex Luna C8 AXIA column, 100 Å) eluting with a gradient of 10-95% acetonitrile/0.1% trifluoroacetic acid in water. The trifluoroacetate salt was dissolved in methanol and loaded on a Bond Elut® MEGA BE-SCX (5 GM) cartridge (pre-washed with 30 mL of 50% methanol in dichloromethane) and washed with methanol, followed by 2M ammonia in methanol. After concentration, the residue was purified by silica gel flash chromatography (Isco®, Redi-Sep® column) eluting with a gradient of 50-100% ethyl acetate/hexane then 10% 2:1 methanol/water in ethyl acetate to give the title compound. $^1$H NMR (400 MHz, dimethylsulfoxide-d$_6$) δ 1.74-1.90 (m, 2 H) 2.21-2.31 (m, 2 H) 3.02-3.20 (m, 3 H) 3.36-3.45 (m, 2 H) 5.71 (s, 2 H) 6.17 (d, J=1.53 Hz, 1 H) 7.17 (d, J=5.19 Hz, 1 H) 7.60 (dd, J=8.39, 1.68 Hz, 1 H) 7.75-7.81 (m, 1 H) 7.83 (d, J=8.24 Hz, 1 H) 7.95 (s, 1 H) 8.23 (d, J=4.88 Hz, 1 H) 8.54-8.63 (m, 3 H) 11.79 (s, 1 H). MS (ESI) m/e 427 (M+H)$^+$.

Example 14

1-(3-fluorobenzyl)-6-[2-(1,2,3,6-tetrahydropyridin-4-yl)-1H-pyrrolo[2,3-b]pyridin-4-yl]-1H-benzimidazole Example 14A tert-butyl 4-(4-chloro-1-tosyl-1H-pyrrolo[2,3-b]pyridin-2-yl)-5,6-dihydropyridine-1(2H)-carboxylate A mixture of 4-chloro-2-iodo-1-tosyl-1H-pyrrolo[2,3-b]pyridine (7.50 g, 17.33 mmol), tert-butyl 4-(4,4,5,5-tetramethyl-1,3,2-dioxaborolan-2-yl)-5,6-dihydropyridine-1(2H)-carboxylate (6.43 g, 20.80 mmol), tetrakis(triphenylphospine)palladium (0.801 g, 0.693 mmol) and aqueous sodium bicarbonate (40 mL) in N,N-dimethylformamide (160 mL) was flushed with nitrogen and heated at 85° C. for 24 hours. The mixture was diluted with water and brine and extracted with ethyl acetate. The organic extracts were washed with water, dried over magnesium sulfate, filtered, concentrated, and purified by flash chromatography on silica (ISCO Companion), eluting with a gradient of 8:2 to 7:3 heptanes/ethyl acetate to give the title compound. MS (ESI$^+$) m/z 488.0 (M+H)$^+$.

Example 14B tert-butyl 4-(4-chloro-1H-pyrrolo[2,3-b]pyridin-2-yl)-5,6-dihydropyridine-1(2H)-carboxylate A mixture of Example 14A (6.500 g, 13.32 mmol) and 20% sodium hydroxide (6 mL) in dioxane (80 mL) was heated at 90° C. for 7 hours. The mixture was concentrated and the residue was treated with ethyl acetate and washed with water. The organic layer was dried over magnesium sulfate, filtered, and concentrated. The precipitate was filtered, washed with ethyl acetate/ether and dried under vacuum to give of the title compound. The filtrate was concentrated and purified by flash chromatography on silica (ISCO Companion), eluting with a gradient of 3:7 to 2:8 heptanes/ethyl acetate to give an additional quantity of the title compound. MS (ESI$^+$) m/z 333.9 (M+H)$^+$.

Example 14C tert-butyl 4-(4-(4,4,5,5-tetramethyl-1,3,2-dioxaborolan-2-yl)-1H-pyrrolo[2,3-b]pyridin-2-yl)-5,6-dihydropyridine-1(2H)-carboxylate A mixture of Example 14B (0.834 g, 2.50 mmol), 4,4,4',4',5,5,5',5'-octamethyl-2,2'-bi(1,3,2-dioxaborolane) (0.952 g, 3.75 mmol), palladium (II) acetate (0.045 g, 0.20 mmol), 2-(dicyclohexylphosphino)biphenyl (0.070 g, 0.200 mmol) and potassium acetate (0.736 g, 7.50 mmol) in dioxane (40 mL) was flushed with nitrogen and heated at 100° C. overnight. After cooling, the mixture was concentrated and the residue treated with ethyl acetate and washed with water and brine. The organic layer was washed with water, dried over magnesium sulfate, filtered, concentrated, and purified by flash chromatography on silica (ISCO Companion), eluting with a gradient of 20:80 to 15:85 heptanes/ethyl acetate to give the title compound. MS (ESI$^+$) m/z 426.2 (M+H)$^+$.

Example 14D tert-butyl 4-(4-(1-(3-fluorobenzyl)-1H-benzo[d]imidazol-6-yl)-1H-pyrrolo[2,3-b]pyridin-2-yl)-5,6-dihydropyridine-1(2H)-carboxylate A mixture of Example 14C (500.0 mg, 1.18 mmol), Example 2C (395 mg, 1.29 mmol), 1,1'-bis(diphenylphosphino)ferrocene-palladium(II)dichloride dichloromethane complex (57.6 mg, 0.071 mmol) and aqueous sodium bicarbonate (5 mL) in N,N-dimethylformamide (20 mL) was flushed with nitrogen and heated at 80° C. for 2.5 hours. The mixture was concentrated and the residue was treated with ethyl acetate and washed with aqueous sodium bicarbonate and brine. The organic layer was washed with water, dried over magnesium sulfate, filtered, concentrated and purified by flash chromatography on silica (ISCO Companion), eluting with a gradient of 10:90 to 0:100 heptanes/ethyl acetate, followed by 5:95 methanol/ethyl acetate to give the title compound. MS (ESI$^+$) m/z 524.1 (M+H)$^+$.

Example 14E 1-(3-fluorobenzyl)-6-[2-(1,2,3,6-tetrahydropyridin-4-yl)-1H-pyrrolo[2,3-b]pyridin-4-yl]-1H-benzimidazole A solution of Example 14D (92.0 mg, 0.176 mmol) in dichloromethane (4 mL) was treated with trifluoroacetic acid (0.14 mL, 1.8 mmol) and the mixture was stirred for 3 hours and concentrated. The residue was dissolved in 2 mL of methanol and slowly treated with 3 mL 2M hydrogen chloride in ether. The suspension was stirred for 15 minutes and diluted with ether. The solids were filtered, washed with ether, treated with aqueous sodium bicarbonate, filtered, washed with water and concentrated to give the title compound. $^1$H NMR (500 MHz, dimethylsulfoxide-d$_6$) δ 2.23-2.29 (m, 2H), 2.92 (t, J=5.6 Hz, 2H), 3.38-3.46 (m, 1H), 5.64 (s, 2H), 6.33 (d, J=1.9 Hz, 1H), 6.53 (s, 1H), 7.11-7.17 (m, 3H), 7.19-7.25 (m, 1H), 7.40 (td, J=7.9, 6.1 Hz, 1H), 7.59 (dd, J=8.3, 1.6 Hz, 1H), 7.83 (d, J=8.3 Hz, 1H), 7.90 (d, J=1.6 Hz, 1H), 8.22 (d, J=5.0 Hz, 1H), 8.54 (s, 1H), 11.81 (bs, 1H) MS (ESI$^+$) m/z 424.2 (M+H)$^+$.

Example 15

1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole To a suspension of Example 14 (61.5 mg, 0.145 mmol) in N,N-dimethylformamide (2 mL) was added methanesulfonyl chloride (0.023 mL, 0.29 mmol) and triethylamine (0.061 mL, 0.436 mmol) and the mixture was stirred for 3 hours. Water was added and the precipitate was filtered, washed with water, and purified by reverse-phase HPLC (Zorbax RX-C18 column) using a gradient of 15-100% methanol/0.1% aqueous trifluoroacetic acid to provide the title compound as the trifluoroacetic acid salt. $^1$H NMR (500 MHz, CD$_3$OD) δ ppm 2.63 (d, J=3.5 Hz, 2H), 2.94 (s, 3H), 3.54 (t, J=5.7 Hz, 2H), 4.02-4.07 (m, 2H), 5.83 (s, 2H), 6.48-6.54 (m, 1H), 6.56 (s, 1H), 7.16 (td, J=8.5, 2.6 Hz, 1H), 7.20-7.27 (m, 2H), 7.40-7.50 (m, 2H), 8.00 (dd, J=8.5, 1.5 Hz, 1H), 8.05 (d, J=8.5 Hz, 1H), 8.11 (s, 1H), 8.32 (d, J=5.6 Hz, 1H), 9.36 (s, 1H). MS (ESI$^+$) m/z 502.2 (M+H)$^+$.

Example 16

4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide To a solution of Example 12D trifluoroacetate salt (30.0 mg, 0.070 mmol) in N,N-dimethylformamide (0.3 mL) was added triethylamine (0.05 ml, 0.352 mmol) and isocyanatomethane (6.0 mg, 0.106 mmol). The mixture was stirred at room temperature for 1 hour, concentrated and purified by reverse-phase HPLC (Phenomenex Luna C8 AXIA column, 100 Å) eluting with a gradient of 10-95% acetonitrile/0.1% trifluoroacetic acid in water with 10 mM ammonium acetate to afford the title compound. $^1$H NMR (400 MHz, dimethylsulfoxide-d$_6$) δ 1.51-1.66 (m, 2 H) 1.87-1.98 (m, 2 H) 2.61 (d, J=4.58 Hz, 3 H) 2.74-2.91 (m, 3 H) 4.04 (m, 2 H) 5.66 (s, 2 H) 6.11 (s, 2 H) 7.10 (d, J=4.88 Hz, 1 H) 7.57 (dd, J=8.54, 1.53 Hz, 1 H) 7.61-7.68 (m, 1 H) 7.76-7.83 (m, 2 H) 8.16 (d, J=5.19 Hz, 1 H) 8.42 (s, 1 H) 8.47-8.52 (m, 2 H) 11.32 (s, 1 H). MS (ESI) m/e 484 (M+H)$^+$.

Example 17

3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol To a mixture of Example 12D trifluoroacetate salt (60 mg), triethylamine (0.06 mL, 0.422 mmol) and acetic acid (42 mg, 0.703 mmol) in dichloromethane (2 mL) was added 2,3-dihydroxypropanal (25.3 mg, 0.281 mmol) and MP-cyanoborohydride (224 mg, 0.563 mmol) and the mixture was stirred at room temperature for 2 days. The solid was filtered and rinsed with 10 mL 50% methanol/dichloromethane. The filtrate was concentrated and purified by reverse-phase HPLC (Phenomenex Luna C8 AXIA column, 100 Å), eluting with a gradient of 10-95% acetonitrile/0.1% trifluoroacetic acid in water with 10 mM ammonium acetate to afford the title compound. $^1$H NMR (400 MHz, dimethylsulfoxide-d$_6$) δ 1.65-1.79 (m, 2 H) 1.91-1.98 (m, 2 H) 2.12-2.25 (m, 2 H) 2.29-2.43 (m, 2 H) 2.65-2.76 (m, 1 H) 2.95-3.05 (m, 2 H) 3.33-3.46 (m, 2 H) 3.60-3.71 (m, 1 H) 5.67 (s, 2 H) 6.11 (s, 1 H) 7.09 (d, J=4.88 Hz, 1 H) 7.57 (dd, J=8.54, 1.53 Hz, 1 H) 7.61-7.68 (m, 1 H) 7.75-7.86 (m, 2 H) 8.15 (d, J=4.88 Hz, 1 H) 8.42 (s, 1 H) 8.46-8.51 (m, 2 H) 11.29 (s, 1 H). MS (ESI) m/e 501 (M+H)$^+$.

Example 18

5-fluoro-6-[2-(piperidin-4-yl)-1H-pyrrolo[2,3-b]pyridin-4-yl]-1-(tetrahydro-2H-pyran-4-ylmethyl)-1H-benzimidazole Example 18A 6-bromo-5-fluoro-1-((tetrahydro-2H-pyran-4-yl)methyl)-1H-benzo[d]imidazole The title compound was prepared as described in Examples 5A-C using 1-bromo-2,5-difluoro-4-nitrobenzene in place of 4-bromo-2-fluoro-1-nitrobenzene. MS (ESI) m/z 313.1 (M+H)$^+$.

Example 18B 5-fluoro-6-[2-(piperidin-4-yl)-1H-pyrrolo[2,3-b]pyridin-4-yl]-1-(tetrahydro-2H-pyran-4-ylmethyl)-1H-benzimidazole The title compound was prepared as described in Example 5D using the product of Example 18A in place of Example 5C. The mixture was filtered through diatomaceous earth with ethyl acetate, concentrated and purified by reverse-phase HPLC (Phenomenex Luna C8 AXIA column, 100 Å), eluting with a gradient of 10-95% acetonitrile/0.1% trifluoroacetic acid in water to afford the title compound as the bis-trifluoroacetate salt. $^1$H NMR (400 MHz, dimethylsulfoxide-d$_6$) δ 1.25-1.50 (m, 4 H) 1.80-1.94 (m, 2 H) 2.09-2.20 (m, 1 H) 2.25 (dd, J=13.73, 2.44 Hz, 2 H) 2.98-3.16 (m, 3 H) 3.21-3.31 (m, 2 H) 3.36 (d, J=12.82 Hz, 2 H) 3.78-3.88 (m, 2 H) 4.24 (d, J=7.02 Hz, 2 H) 6.13 (d, J=1.53 Hz, 1 H) 7.15 (dd, J=5.04, 1.37 Hz, 1 H) 7.63 (d, J=10.68 Hz, 1 H) 7.88 (d, J=6.41 Hz, 1 H) 8.26 (d, J=4.88 Hz, 1 H) 8.33 (s, 1 H) 8.50 (s, 1 H) 8.63 (s, 1 H) 11.58 (s, 1 H). MS (ESI) m/e 434 (M+H)$^+$.

Example 19

3-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)propane-1,2-diol The title compound was prepared as described in Example 17 using Example 18 in place of Example 12D. $^1$H NMR (400 MHz, dimethylsulfoxide-d$_6$) δ 1.22-1.51 (m, 4 H) 1.64-1.78 (m, 2 H) 1.92-2.03 (m, 2 H) 2.06-2.24 (m, 3 H) 2.26-2.43 (m, 2 H) 2.66-2.79 (m, 1 H) 2.88-3.03 (m 2 H) 3.20-3.30 (m, 2 H) 3.32-3.43 (m, 2 H) 3.58-3.67 (m, 1 H) 3.76-3.87 (m, 2 H) 4.19 (d, J=7.32 Hz, 2 H) 6.08 (d, J=1.22 Hz, 1 H) 7.09 (dd, J=4.88, 1.53 Hz, 1 H) 7.55 (d, J=10.99 Hz, 1 H) 7.78 (d, J=6.41 Hz, 1 H) 8.18 (d, J=5.19 Hz, 1 H) 8.25 (s, 1 H) 11.32 (s, 1 H). MS (ESI) m/e 508 (M+H)$^+$.

Example 20

4-{4-[5-fluoro-1-(tetrahydro-2H-pyran-4-ylmethyl)-1H-benzimidazol-6-yl]-1H-pyrrolo[2,3-b]pyridin-2-yl}-N-methylpiperidine-1-carboxamide The title compound was prepared as described in Example 16 using Example 18 in place of Example 12D. $^1$H NMR (400

MHz, dimethylsulfoxide-d$_6$) δ 1.23-1.38 (m, 2 H) 1.39-1.49 (m, 2 H) 1.52-1.64 (m, 2 H) 1.93-2.02 (m, 2 H) 2.06-2.20 (m, 1 H) 2.59 (s, 3 H) 2.74-2.85 (m, 2 H) 2.87-2.94 (m, 1 H) 3.17-3.33 (m, 2 H) 3.79-3.88 (m, 2 H) 3.94-4.05 (m, 2 H) 4.19 (d, J=7.02 Hz, 2 H) 6.08 (s, 2 H) 7.09 (dd, J=4.88, 1.53 Hz, 1 H) 7.55 (d, J=10.99 Hz, 1 H) 7.78 (d, J=6.71 Hz, 1 H) 8.19 (d, J=4.88 Hz, 1 H) 8.26 (s, 1 H) 11.35 (s, 1 H). MS (ESI) m/e 491 (M+H)$^+$.

Example 21

1-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)-2-hydroxyethanone To a solution of Example 18 (100 mg, 0.231 mmol) in N,N-dimethylformamide (1 mL) was added 70% 2-hydroxyacetic acid in water (37.6 mg, 0.346 mmol), N$^1$-((ethylimino)methylene)-N$^3$,N$^3$-dimethylpropane-1,3-diamine hydrochloride (66.3 mg, 0.346 mmol), 1H-benzo[d][1,2,3]triazol-1-ol hydrate (53.0 mg, 0.346 mmol) and triethylamine (0.193 mL, 1.384 mmol) and the mixture was stirred at room temperature for 24 hours. The mixture was concentrated and the residue purified by reverse-phase HPLC (Phenomenex Luna C8 AXIA column, 100 Å), eluting with a gradient of 10-95% acetonitrile/0.1% trifluoroacetic acid in water with 10 mM ammonium acetate to afford the title compound. $^1$H NMR (400 MHz, dimethylsulfoxide-d$_6$) δ 1.25-1.38 (m, 2 H) 1.41-1.50 (m, 2 H) 1.57-1.72 (m, 2 H) 1.99-2.19 (m, 3 H) 2.98-3.12 (m, 3 H) 3.20-3.31 (m, 2 H) 3.77-3.87 (m, 2 H) 4.06-4.17 (m, 4 H) 4.19 (d, J=7.02 Hz, 2 H) 6.10 (s, 1 H) 7.10 (dd, J=4.88, 1.53 Hz, 1 H) 7.55 (d, J=10.99 Hz, 1 H) 7.78 (d, J=6.71 Hz, 1 H) 8.20 (d, J=4.88 Hz, 1 H) 8.25 (s, 1 H) 11.37 (s, 1 H). MS (ESI) m/e 492 (M+H)$^+$.

Example 22

1-benzyl-6-[6-(1,2,3,6-tetrahydropyridin-4-yl)-7H-pyrrolo[2,3-d]pyrimidin-4-yl]-1H-indole-3-carbonitrile

Example 22A tert-butyl 4-(4-chloro-7-(phenylsulfonyl)-7H-pyrrolo[2,3-d]pyrimidin-6-yl)-5,6-dihydropyridine-1(2H)-carboxylate A mixture of cesium carbonate (7.45 g, 22.88 mmol), 1,1'-bis(diphenylphosphino)ferrocene-palladium(II)dichloride dichloromethane complex (0.778 g, 0.95 mmol), tert-butyl 4-(4,4,5,5-tetramethyl-1,3,2-dioxaborolan-2-yl)-5,6-dihydropyridine-1(2H)-carboxylate (3.98 g, 12.87 mmol), and 4-chloro-6-iodo-7-(phenylsulfonyl)-7H-pyrrolo[2,3-d]pyrimidine (5 g, 9.53 mmol) in tetrahydrofuran (50 mL) and water (8.33 mL) was heated at 65° C. for 16 hours, diluted with ethyl acetate and washed with water and brine. The organic layer was dried over sodium sulfate, filtered, and concentrated. The residue was purified by flash chromatography on silica (IntelliFlash Varian 971-FP), eluting with a gradient of 5-80% ethyl acetate in heptanes to provide the title compound. ESI MS: 497.1 (M+Na)$^+$.

Example 22B benzyl-6-bromo-1H-indole-3-carbonitrile

A solution of 6-bromo-1H-indole-3-carbonitrile (400 mg, 1.81 mmol), 2-(tributylphosphoranylidene)acetonitrile (655 mg, 2.71 mmol) and benzyl alcohol (282 μL, 2.71 mmol) in toluene (5 mL) was heated at 75° C. overnight and concentrated. The residue was purified by flash chromatography on silica (IntelliFlash Varian 971-FP), eluting with 30% heptanes in ethyl acetate to provide the title compound. LCMS: 312.4 (M+H)$^+$.

Example 22C tert-butyl 4-(4-(1-benzyl-3-cyano-1H-indol-6-yl)-7-(phenylsulfonyl)-7H-pyrrolo[2,3-d]pyrimidin-6-yl)-5,6-dihydropyridine-1(2H)-carboxylate A mixture of Example 22B (350 mg, 1.12 mmol), 4,4,4',4',5,5,5',5'-octamethyl-2,2'-bi(1,3,2-dioxaborolane) (314 mg, 1.24 mmol) and potassium acetate (331 mg, 3.37 mmol) in dioxane (2.5 mL) was flushed with nitrogen and 1,1'-bis(diphenylphosphino)ferrocene-palladium(II)dichloride dichloromethane complex (55.1 mg, 0.07 mmol) was added. The mixture was stirred at 100° C. overnight and cooled. To this mixture was added Example 22A (504 mg, 1.06 mmol), 1M sodium carbonate (3.18 mL, 3.18 mmol), 2 mL dioxane and 1,1'-bis(diphenylphosphino)ferrocene-palladium(II) dichloride dichloromethane complex (87 mg, 0.106 mmol). The mixture was stirred at 100° C. overnight, filtered, concentrated and purified by flash chromatography on silica (IntelliFlash Varian 971-FP), eluting with a gradient of 25-80% ethyl acetate in heptanes to provide the title compound. LCMS: 671.3 (M+H)$^+$.

Example 22D tert-butyl 4-(4-(1-benzyl-3-cyano-1H-indol-6-yl)-7H-pyrrolo[2,3-d]pyrimidin-6-yl)-5,6-dihydropyridine-1(2H)-carboxylate To a solution of Example 22C (500 mg, 0.75 mmol) in tetrahydrofuran (5 mL) and methanol (3 mL) was added 1M sodium hydroxide (2.24 mL, 2.24 mmol) and the mixture was stirred at 50° C. overnight. The mixture was diluted with water, extracted with dichloromethane, dried over sodium sulfate, filtered, and concentrated to provide the title compound. LCMS: 531.2 (M+H)$^+$.

Example 22E 1-benzyl-6-[6-(1,2,3,6-tetrahydropyridin-4-yl)-7H-pyrrolo[2,3-d]pyrimidin-4-yl]-1H-indole-3-carbonitrile To a solution of Example 22D (350 mg, 0.66 mmol) in dichloromethane (5 mL) was added trifluoroacetic acid (1.5 mL) and the mixture was stirred for 30 minutes and concentrated. The residue was purified by reverse phase chromatography (IntelliFlash Varian 971-FP, Grace Reveleris C18 column), eluting with a gradient of 10-70% acetonitrile/0.1% trifluoroacetic acid in water to provide the title compound as the trifluoroacetate salt. $^1$H NMR (400 MHz, dimethylsulfoxide-d$_6$) δ 2.73 (s, 2 H) 3.42 (d, 2 H) 3.89 (s, 2 H) 5.71 (s, 2 H) 6.58 (s, 1 H) 6.78 (d, 1 H) 7.26-7.33 (m, 3 H) 7.34-7.40 (m, 2

H) 7.87 (d, 1 H) 8.11 (dd, 1 H) 8.30 (s, 1 H) 8.66 (s, 1 H) 8.85 (s, 1 H) 9.04 (s, 2 H) 12.63 (s, 1 H). LCMS: 431.1 (M+H)$^+$.

Example 23

5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole The title compound was prepared as described in Example 4 using Example 18 in place of Example 2D. Purification by reverse-phase HPLC (Phenomenex Luna C8 AXIA column, 100 Å), eluting with a gradient of 10-95% acetonitrile/0.1% trifluoroacetic acid in water afforded the title compound as the trifluoroacetate salt. $^1$H NMR (400 MHz, dimethylsulfoxide-d$_6$) δ 1.25-1.40 (m, 2 H) 1.42-1.52 (m, 2 H) 1.68-1.84 (m, 2 H) 2.03-2.22 (m, 3 H) 2.86 (s, 3 H) 2.87-2.96 (m, 3 H) 3.20-3.33 (m, 2 H) 3.61-3.72 (m, 2 H) 3.77-3.88 (m, 2 H) 4.26 (d, J=7.32 Hz, 2 H) 6.14 (s, 1 H) 7.14 (dd, J=5.19, 1.53 Hz, 1 H) 7.64 (d, J=10.68 Hz, 1 H) 7.91 (d, J=6.10 Hz, 1 H) 8.24 (d, J=4.88 Hz, 1 H) 8.57 (s, 1 H) 11.54 (s, 1 H). MS (ESI) m/e 512 (M+H)$^+$.

Example 24

4-{4-[1-(3-fluorobenzyl)-1H-benzimidazol-6-yl]-1H-pyrrolo[2,3-b]pyridin-2-yl}-N-methyl-3,6-dihydropyridine-1(2H)-carboxamide To a suspension of Example 14E (65.0 mg, 0.131 mmol) and N-succinimidyl-N-methylcarbamate (33.8 mg, 0.196 mmol) in N,N-dimethylformamide (2.5 mL) was added triethylamine (0.110 mL, 0.786 mmol). The reaction was stirred for 16 hours. The reaction mixture was treated with brine and aqueous NaHCO$_3$ and extracted with ethyl acetate (twice). The combined organic layers were dried over Na$_2$SO$_4$, filtered, concentrated, and purified by HPLC (see protocols in Example 15) to give the title compound as a trifluoroacetic acid salt. $^1$H NMR (500 MHz, methanol-d$_4$) δ ppm 2.47-2.56 (m, 2H), 2.77 (s, 3H), 3.67 (t, J=5.6 Hz, 2H), 4.11-4.16 (m, 2H), 5.82 (s, 2H), 6.46-6.52 (m, 1H), 6.53 (s, 1H), 7.14-7.28 (m, 3H), 7.41-7.50 (m, 2H), 7.99 (dd, J=8.5, 1.5 Hz, 1H), 8.05 (d, J=8.5 Hz, 1H), 8.10 (d, J=1.4 Hz, 1H), 8.31 (d, J=5.7 Hz, 1H), 9.34 (s, 1H). MS (ESI$^+$) m/z 481 (M+H)$^+$.

Example 25

3-[4-{4-[1-(3-fluorobenzyl)-1H-benzimidazol-6-yl]-1H-pyrrolo[2,3-b]pyridin-2-yl}-3,6-dihydropyridin-1(2H)-yl]propane-1,2-diol To a mixture of Example 14E (70.0 mg, 0.141 mmol), triethylamine (0.043 mL, 0.310 mmol), and acetic acid (0.040 mL, 0.705 mmol) in dichloromethane (1.5 mL) and methanol (1.5 mL) was added 2,3-dihydroxypropanal (25.4 mg, 0.282 mmol) and MP-CNBH$_3$ (Biotage 2.48 mmol/mg, 227 mg, 0.564 mmol). The reaction was heated at 40° C. for 4 hours. The solid material was filtered and rinsed with dichloromethane/methanol. The filtrate was concentrated and purified by HPLC (see protocols in Example 15) to give the title compound as a trifluoroacetic acid salt. $^1$H NMR (400 MHz, methanol-d$_4$) δ ppm 2.88-2.96 (m, 2H), 3.33-3.45 (m, 2H), 3.56-3.66 (m, 2H), 3.76-4.32 (m, 4H), 5.84 (s, 2H), 6.47-6.52 (m, 1H), 6.69 (s, 1H), 7.17 (td, J=8.5, 2.6 Hz, 1H), 7.21-7.28 (m, 2H), 7.40-7.51 (m, 2H), 7.99-8.09 (m, 2H), 8.12 (s, 1H), 8.37 (d, J=5.5 Hz, 1H), 9.40 (s, 1H). MS (ESI$^+$) m/z 498 (M+H)$^+$.

Example 26

N-(4-{[4-{4-[1-(3-fluorobenzyl)-1H-benzimidazol-6-yl]-1H-pyrrolo[2,3-b]pyridin-2-yl}-3,6-dihydropyridin-1(2H)-yl]methyl}phenyl)acetamide To a mixture of Example 14E (70.0 mg, 0.141 mmol), triethylamine (0.043 mL, 0.310 mmol), and acetic acid (0.040 mL, 0.705 mmol) in dichloromethane (1.5 mL) and methanol (1.5 mL) was added N-(4-formylphenyl)acetamide (46.0 mg, 0.282 mmol) and MP-CNBH$_3$ (Biotage 2.48 mmol/mg, 227 mg, 0.564 mmol). The reaction mixture was heated at 40° C. for 4 hours. The solid material was filtered and rinsed with dichloromethane/methanol. The filtrate was concentrated and purified by HPLC (see protocols in Example 15) to give the title compound as a trifluoroacetic acid salt. $^1$H NMR (400 MHz, methanol-d$_4$) δ ppm 2.15 (s, 3H), 2.90 (dt, J=7.2, 3.7 Hz, 2H), 3.40-3.96 (m, 2H), 3.96-4.02 (m, 2H), 4.45 (s, 2H), 5.82 (s, 2H), 6.46 (bs, 1H), 6.68 (s, 1H), 7.09-7.18 (m, 1H), 7.20-7.27 (m, 2H), 7.37-7.47 (m, 2H), 7.51-7.53 (m, 2H), 7.69-7.75 (m, 2H), 7.98-8.05 (m, 2H), 8.10 (s, 1H), 8.36 (d, J=5.5 Hz, 1H), 9.36 (s, 1H). MS (ESI$^+$) m/z 571 (M+H)$^+$.

Example 27

5-chloro-6-[2-(piperidin-4-yl)-1H-pyrrolo[2,3-b]pyridin-4-yl]-1-(tetrahydro-2H-pyran-4-ylmethyl)-1H-benzimidazole The title compound was prepared as described in Example 5 substituting 1-bromo-2-chloro-5-fluoro-4-nitrobenzene for 4-bromo-2-fluoro-1-nitrobenzene. The reaction mixture was concentrated and the residue was purified by reverse-phase HPLC performed on a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-d$_6$) δ ppm 1.18-1.65 (m, 7 H) 1.91-2.01 (m, 2 H) 2.02-2.16 (m, 1 H) 2.59-3.09 (m, 7 H) 3.76-3.87 (m, 2 H) 4.17 (d, J=7.02 Hz, 2 H) 5.89 (s, 1 H) 7.02 (d, J=5.19 Hz, 1 H) 7.73 (s, 1 H) 7.85 (s, 1 H) 8.18 (d, J=4.88 Hz, 1 H) 8.27 (s, 1 H) 11.32 (s, 1 H). MS (ESI) m/e 450 (M+H)$^+$.

Example 28

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine-3-carbonitrile Example 28A 6-bromo-1-((tetrahydro-2H-pyran-4-yl)methyl)-1H-pyrrolo[3,2-b]pyridine-3-carbonitrile To mixture of 6-bromo-1H-pyrrolo[3,2-b]pyridine-3-carbonitrile (500 mg, 2.252 mmol) in N,N-dimethylformamide (4.5 mL) was added sodium hydride (60% dispersion in mineral oil) (59.4 mg, 2.477 mmol) followed by 4-(bromomethyl)tetrahydro-2H-pyran (444 mg, 2.477 mmol). The mixture was heated at 100° C. for 2 hours. The reaction was diluted with 50 mL of ethyl acetate and the organic mixture was washed with a solution of aqueous sodium bicarbonate (1×50 mL), water (1×50 mL), and brine (1×30 mL), dried over magnesium sulfate, filtered, concentrated, and purified by silica gel flash chromatography (Isco®, Redi-Sep® column) eluting with a gradient of 30-100% ethyl acetate/hexane to afford the title compound.

Example 28B tert-butyl 4-(4-(3-cyano-1-((tetrahydro-2H-pyran-4-yl)methyl)-1H-pyrrolo[3,2-b]pyridin-6-yl)-1H-pyrrolo[2,3-b]pyridin-2-yl)piperidine-1-carboxylate An oven-dried flask was charged with tris(dibenzylideneacetone)dipalladium(0) (0.057 g, 0.062 mmol), 2-(dicyclohexylphosphino)-2',4',6'-triisopropylbiphenyl (0.118 g, 0.247 mmol), bis(pinacolato)diboron (0.314 g, 1.236 mmol), potassium acetate (0.243 g, 2.471 mmol) and Example 1F (0.415 g, 1.236 mmol) then purged with argon. Dioxane (4.94 mL) was added and the reaction mixture was stirred at 110° C. for three hours. Example 28A (0.356 g, 1.112 mmol) in 2.0 mL dioxane was added followed by 5 M aqueous potassium phosphate (1.2 mL, 6.18 mmol) and the mixture was heated at 110° C. for 3 hours. The reaction mixture was filtered through diatomaceous earth and rinsed with 20 mL of ethyl acetate. The filtrate was concentrated then purified via silica gel flash chromatography (Isco®, Redi-Sep® column) eluting with a gradient of 50-100% ethyl acetate/hexane then 10% of a 2:1 methanol:water mixture in ethyl acetate to give the title compound.

Example 28C

6-{2-(piperidin-4-yl)-1H-pyrrolo[2,3-b]pyridin-4-yl}-1-(tetrahydro-2H-pyran-4-ylmethyl)-1H-pyrrolo[3,2-b]pyridine-3-carbonitrile Example 28B (200 mg, 0.37 mmol) was dissolved in 4 mL 1:1 trifluoroacetic acid:dichloromethane and the mixture was stirred for 30 minutes at ambient temperature. The reaction was concentrated then purified by reverse-phase HPLC (Phenomenex Luna C8(2) 100 Å AXIA column) using a gradient of 10-95% acetonitrile/0.1% trifluoroacetic acid in water to afford the title compound as a bis trifluoroacetic acid salt. $^1$H NMR (400 MHz, DMSO-$d_6$) δ ppm 1.27-1.47 (m, 4H), 1.77-1.95 (m, 2H), 2.06-2.22 (m, 1H), 2.24-2.36 (m, 2H), 3.00-3.19 (m, 3H), 3.19-3.29 (m, 2H), 3.34-3.49 (m, 2H), 3.77-3.92 (m, 2H), 4.31 (d, J=7.2 Hz, 2H), 6.37-6.52 (m, 1H), 7.34 (d, J=5.0 Hz, 1H), 8.32 (d, J=5.0 Hz, 1H), 8.36-8.52 (m, 1H), 8.58 (d, J=1.8 Hz, 1H), 8.66 (s, 1H), 8.69-8.79 (m, 1H), 8.92 (d, J=1.8 Hz, 1H), 11.97 (s, 1H). MS (ESI$^+$) m/z 441.3 (M+H)$^+$.

Example 29

1-(3-fluorobenzyl)-6-[2-(piperidin-4-yl)-1H-pyrrolo[2,3-b]pyridin-4-yl]-1H-pyrrolo[3,2-b]pyridine

Example 29A 6-bromo-1-(3-fluorobenzyl)-1H-pyrrolo[3,2-b]pyridine

A mixture of 6-bromo-1H-pyrrolo[3,2-b]pyridine (400 mg, 2.030 mmol) and sodium hydride (60% in mineral oil) (89 mg, 2.233 mmol) in 4 mL N,N-dimethylformamide was stirred at ambient temperature for 10 minutes and 1-(bromomethyl)-3-fluorobenzene (384 mg, 2.030 mmol) was added. The mixture was heated at 100° C. for 3 hours. The mixture was cooled to ambient temperature, diluted with 100 mL of ethyl acetate and washed successively with water and brine, dried over MgSO$_4$, filtered, and concentrated. The residue was purified by flash chromatography on Analogix IntelliFlash$^{280}$ eluting with 10 to 70% ethyl acetate/hexanes to give the title compound.

Example 29B 1-(3-fluorobenzyl)-6-[2-(piperidin-4-yl)-1H-pyrrolo[2,3-b]pyridin-4-yl]-1H-pyrrolo[3,2-b]pyridine The title compound was prepared as described in Example 1H substituting Example 29A for Example 1G. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (400 MHz, DMSO-$d_6$) δ ppm 1.77-1.97 (m, 2H) 2.20-2.29 (m, 2H) 3.00-3.20 (m, 3H) 3.32-3.46 (m, 2H) 5.62 (s, 2H) 6.26 (s, 1H) 6.79 (d, J=3.36 Hz, 1H) 7.03-7.15 (m, 3H) 7.23 (d, J=4.88 Hz, 1H) 7.32-7.46 (m, 1H) 8.01 (d, J=3.36 Hz, 1H) 8.26 (d, J=5.19 Hz, 1H) 8.39 (s, 1H) 8.64 (s, 1H) 8.80 (d, J=1.83 Hz, 1H) 11.62 (s, 1H). MS (ESI) m/e 426 (M+H)$^+$.

Example 30

6-{2-(piperidin-4-yl)-1H-pyrrolo[2,3-b]pyridin-4-yl}-1-(tetrahydro-2H-pyran-4-ylmethyl)-1H-pyrrolo[3,2-b]pyridine

Example 30A 6-bromo-1-((tetrahydro-2H-pyran-4-yl)methyl)-1H-pyrrolo[3,2-b]pyridine The title compound was prepared as described in Example 29A substituting 4-(bromomethyl)tetrahydro-2H-pyran for 1-(bromomethyl)-3-fluorobenzene.

Example 30B

6-{2-(piperidin-4-yl)-1H-pyrrolo[2,3-b]pyridin-4-yl}-1-(tetrahydro-2H-pyran-4-ylmethyl)-1H-pyrrolo[3,2-b]pyridine The title compound was prepared as described in Example 1H substituting Example 30A for Example 1G. The reaction mixture was concentrated and the residue was purified by reverse-phase HPLC performed on a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-$d_6$) δ ppm 1.25-1.71 (m, 6H) 1.93-2.19 (m, 3H) 2.59-3.32 (m, 7H) 3.77-3.89 (m, 2H) 4.18 (d, J=7.02 Hz, 2H) 6.33 (s, 1H) 6.62 (d, J=2.44 Hz, 1H) 7.20 (d, J=4.88 Hz, 1H) 7.68 (d, J=3.36 Hz, 1H) 8.16-8.22 (m, 2H) 8.70 (d, J=1.83 Hz, 1H) 11.35 (s, 1H). MS (ESI) m/e 416 (M+H)$^+$.

Example 31

1-benzyl-6-{6-[1-(2,3-dihydroxypropyl)-1,2,3,6-tetrahydropyridin-4-yl]-7H-pyrrolo[2,3-d]pyrimidin-4-yl}-1H-indole-3-carbonitrile To a solution of Example 22E (150 mg, 0.35 mmol) in dichloromethane (3 mL) and methanol (0.5 mL) was added triethylamine (0.15 mL, 1.04 mmol), 2,3-dihydroxypropanal (157 mg, 1.74 mmol), acetic acid (0.1 mL, 1.74 mmol) and MP-CNBH₃ (Biotage, 2.49 mmol/g) (560 mg, 1.39 mmol). The mixture was stirred for 16 hours and filtered. The filtrate was concentrated and the residue was purified by reverse phase chromatography using an IntelliFlash Varian 971-FP system (column: Grace Reveleris C18, 120 g), eluted with 10%-70% acetonitrile in 0.1% TFA water solution to provide the title compound. $^1$H NMR (500 MHz, DMSO-d$_6$) δ ppm 2.74-2.99 (m, 2 H) 3.11-3.25 (m, 1 H) 3.29-3.43 (m, 3 H) 3.46-3.51 (m, 1 H) 3.72-3.85 (m, 1 H) 3.93-4.08 (m, 2 H) 4.09-4.24 (m, 1 H) 5.71 (s, 2 H) 6.55 (s, 1 H) 6.78 (s, 1 H) 7.31 (t, 3 H) 7.37 (t, 2 H) 7.87 (d, 1 H) 8.09-8.15 (m, 1 H) 8.31 (s, 1 H) 8.66 (s, 1 H) 8.85 (s, 1 H) 9.85 (s, 1 H) 12.62 (s, 1 H). LCMS: 505 (M+H)$^+$.

Example 32

1-[2-(3-fluorophenyl)ethyl]-6-{2-(piperidin-4-yl)-1H-pyrrolo[2,3-b]pyridin-4-yl}-1H-benzotriazole Example 32A 5-bromo-N-(3-fluorophenethyl)-2-nitroaniline A mixture of 4-bromo-2-fluoronitrobenzene (500 mg, 2.27 mmol), 2-(3-fluorophenyl)ethylamine (411 mg, 2.95 mmol), and potassium carbonate (1.0 g, 7.24 mmol) in 7 mL N,N-dimethylformamide was heated at 80° C. for 1 hour. The mixture was diluted with ethyl acetate, rinsed with brine (three times), dried over magnesium sulfate, filtered, and concentrated to give the title compound.

Example 32B 5-bromo-N1-(3-fluorophenethyl)benzene-1,2-diamine

To Example 32A (730 mg, 2.15 mmol) in 10 mL methanol was added hydrazine monohydrate (0.25 mL, 5.15 mmol) and approximately 50 mg Raney nickel. The mixture was heated at 55° C. for 2 hours, filtered through diatomaceous earth, and concentrated to yield the title compound.

Example 32C 6-bromo-1-(3-fluorophenethyl)-1H-benzo[d][1,2,3]triazole

To Example 32B (300 mg, 0.97 mmol) in 3 mL glacial acetic acid was added 6M aqueous sodium nitrite (0.5 mL, 3 mmol). The reaction was stirred at room temperature for 30 minutes, was diluted with water, and extracted into ethyl acetate (three times). The combined extracts were rinsed with water and brine, dried over magnesium sulfate, filtered, and concentrated to give the title compound.

Example 32D

1-[2-(3-fluorophenyl)ethyl]-6-{2-(piperidin-4-yl)-1H-pyrrolo[2,3-b]pyridin-4-yl}-1H-benzotriazole Example 1F (89 mg, 0.26 mmol), 4,4,4',4',5,5,5',5'-octamethyl-2,2'-bi(1,3,2-dioxaborolane) (68 mg, 0.27 mmol), tris(dibenzylideneaceton)dipalladium (0) (13 mg, 0.014 mmol) potassium acetate (52 mg, 0.53 mmol) and 2-(dicyclohexylphosphino)-2',4',6'-trispropylbiphenyl (26 mg, 0.06 mmol) were dissolved in 3 mL dioxane, flushed with N₂ and heated at 110° C. for 3 hours. After cooling to room temperature, Example 32C (85 mg, 0.26 mmol) and a potassium phosphate solution (5M, 0.3 mL) were added. The reaction was heated for 3 hours at 110° C., cooled to room temperature and concentrated. Purification by reverse phase-HPLC (Sunfire 5 μM, 50×250 mm) eluting with 5-50% acetonitrile in water (containing 0.1% trifluoroacetic acid) provided the title compound as the trifluoroacetic acid salt. $^1$HNMR (500 MHz, DMSO-d$_6$) δ 1.86 (m, 2H), 2.26 (m, 2H), 3.10 (m, 3H), 3.33 (t, 2H), 3.39 (br d, 2H), 5.08 (t, 2H), 6.40 (s, 1H), 6.99 (m, 2H), 7.10 (d, 1H), 7.25 (m, 2H), 7.75 (d, 1H), 8.12 (s, 1H), 8.16 (d, 1H), 8.29 (d, 1H), 8.40 (m, 1H), 8.72 (m, 1H), 11.93 (br s, 1H). MS (ESI) m/e 441.2 (M+H)$^+$.

Example 33

6-[3-chloro-2-(piperidin-4-yl)-1H-pyrrolo[2,3-b]pyridin-4-yl]-1-[2-(3-fluorophenyl)ethyl]-1H-benzotriazole Example 32 (147 mg; 0.26 mmol) was dissolved in 5 mL methanol and 2M HCl in ether was added until the solution turned cloudy. After stirring for 15 minutes, the mixture was concentrated and purified by reverse phase-HPLC (Sunfire 5 μM, 50×250 mm) eluting with 5-50% acetonitrile in water (containing 0.1% trifluoroacetic acid) to provide the title compound as the trifluoroacetic acid salt. $^1$H NMR (500 MHz, DMSO-d$_6$) δ 1.97 (m, 2H), 2.09 (m, 2H), 3.09 (br q, 2H), 3.31 (m, 2H), 3.41 (br d, 3H), 5.03 (t, 2H), 6.98 (m, 2H), 7.08 (m, 2H), 7.25 (q, 1H), 7.50 (d, 1H), 7.98 (s, 1H), 8.07 (d, 1H), 8.34 (d, 1H), 8.42 (m, 1H), 8.78 (m, 1H), 12.35 (br s, 1H). MS (ESI) m/e 475.1 (M+H)$^+$.

Example 34

1-(3-fluorobenzyl)-6-{2-[1-(methylsulfonyl)piperidin-4-yl]-1H-pyrrolo[2,3-b]pyridin-4-yl}-1H-pyrrolo[3,2-b]pyridine To Example 29B (77 mg, 0.118 mmol) in 1 mL N,N-dimethylformamide were added methanesulfonyl chloride (0.016 mL, 0.212 mmol) and triethylamine (0.098 mL, 0.705 mmol). The mixture was stirred at room temperature for 1 hour. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (400 MHz, DMSO-d$_6$) δ ppm 1.70-2.14 (m, 4 H) 2.88 (s, 3 H) 2.88-2.97 (m, 3 H) 3.66-3.77 (m, 2 H) 5.64 (s, 2 H) 6.20 (s, 1 H) 6.81 (d, J=3.05 Hz, 1 H) 7.05-7.15 (m, 3 H) 7.23 (d, J=4.88 Hz, 1 H) 7.32-7.44 (m, 1 H) 8.06 (d, J=3.36 Hz, 1 H) 8.24 (d, J=4.88 Hz, 1 H) 8.44 (s, 1 H) 8.81 (d, J=1.83 Hz, 1 H) 11.58 (s, 1 H). MS (ESI) m/e 504 (M+H)$^+$.

Example 35

1'-(3-fluorobenzyl)-2-(piperidin-4-yl)-1H,1'H-4,6'-bipyrrolo[2,3-b]pyridine-3'-carbonitrile Example 35A 6-bromo-1-(3-fluorobenzyl)-1H-pyrrolo[2,3-b]pyridine-3-carbonitrile The title compound was prepared as described in Example 28A using 6-bromo-1H-pyrrolo[2,3-b]pyridine-3-carbonitrile in place of 6-bromo-1H-pyrrolo[3,2-b]pyridine-3-carbonitrile and using 1-(bromomethyl)-3-fluorobenzene in place of 4-(bromomethyl)tetrahydro-2H-pyran.

Example 35B tert-butyl 4-(3'-cyano-1'-(3-fluorobenzyl)-1H,1'H-4, 6'-bipyrrolo[2,3-b]pyridin-2-yl)piperidine-1-carboxylate The title compound was prepared as described in Example 28B using Example 35A in place of Example 28A.

Example 35C

1'-(3-fluorobenzyl)-2-(piperidin-4-yl)-1H,1'H-4,6'-bipyrrolo[2,3-b]pyridine-3'-carbonitrile Example 35B (150 mg, 0.272 mmol) in 1 mL of dichloromethane and 1 mL of methanol was cooled to 0° C. and 5 mL of 2 M hydrochloric acid in ether was added. The cooling bath was removed and the reaction was stirred at ambient temperature for 2 hours. The reaction mixture was concentrated to obtain the title compound as the bis hydrochloric acid salt. $^1$H NMR (400 MHz, DMSO-$d_6$) δ ppm 1.79-2.00 (m, 2H), 2.12-2.29 (m, 2H), 2.91-3.24 (m, 3H), 3.29-3.45 (m, 2H), 5.74 (s, 2H), 6.91 (d, J=1.9 Hz, 1H), 7.06-7.26 (m, 3H), 7.35-7.49 (m, 1H), 7.87 (d, J=5.6 Hz, 1H), 8.17 (d, J=8.4 Hz, 1H), 8.34-8.50 (m, 2H), 8.85 (s, 1H), 9.01-9.24 (m, 1H), 9.24-9.44 (m, 1H), 12.64 (s, 1H). MS (ESI$^+$) m/z 451.4 (M+H)$^+$.

Example 36

1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole

Example 36A 4-bromo-1-tosyl-1H-pyrrolo[2,3-b]pyridine

To a suspension of 4-bromo-1H-pyrrolo[2,3-b]pyridine (15 g, 76 mmol) and p-toluenesulfonyl chloride (21.77 g, 114 mmol) in toluene (200 mL) was added a solution of tetrabutylammonium hydrogen sulfate (2.58 g, 7.61 mmol) in water (10 mL) and the mixture was cooled to 0° C. A solution of sodium hydroxide (9.13 g, 228 mmol) in water (30 mL) was added and the mixture was stirred at room temperature for 16 hours. The mixture was diluted with ethyl acetate and the solution was washed with saturated sodium chloride solution. The organic layer was dried over sodium sulfate, filtered and concentrated to give the title compound.

Example 36B 4-bromo-2-iodo-1-tosyl-1H-pyrrolo[2,3-b]pyridine

To a solution of Example 36A (25 g, 71.2 mmol) in tetrahydrofuran (600 mL) at −78° C. was added slowly 2M lithium diisopropylamide in heptane/tetrahydrofuran/ethyl benzene (39.1 mL, 78 mmol) and the mixture was stirred at −78° C. for 1 hour. A solution of iodine (19.87 g, 78 mmol) in tetrahydrofuran (100 mL) was added slowly and the reaction was allowed to warm gradually to room temperature. The reaction mixture was stirred at room temperature for 3 hours. Saturated aqueous sodium thiosulfate and water were added and the mixture was extracted with ethyl acetate. The combined organics were dried over sodium sulfate, filtered, and concentrated to give the title compound.

Example 36C tert-butyl 4-(4-bromo-1-tosyl-1H-pyrrolo[2,3-b]pyridin-2-yl)-5,6-dihydropyridine-1(2H)-carboxylate To as solution of Example 36B (20 g, 41.9 mmol), tert-butyl 4-(4,4,5,5-tetramethyl-1,3,2-dioxaborolan-2-yl)-5,6-dihydropyridine-1(2H)-carboxylate (16.85 g, 54.5 mmol), and tetrakis(triphenylphosphine)palladium (4.84 g, 4.19 mmol) in N,N-dimethylformamide (500 mL) was added a solution of sodium bicarbonate (7.04 g, 84 mmol) in water (40 mL) and the mixture was stirred at 80° C. for 12 hours. Saturated aqueous sodium thiosulfate and water were added and the mixture was extracted with ethyl acetate. The combined organics were dried over sodium sulfate, filtered, and concentrated to give the title compound.

Example 36D tert-butyl 4-(4-(4,4,5,5-tetramethyl-1,3,2-dioxaborolan-2-yl)-1-tosyl-1H-pyrrolo[2,3-b]pyridin-2-yl)-5,6-dihydropyridine-1(2H)-carboxylate A mixture of potassium acetate (5.53 g, 56.3 mmol), 1,1'-bis(diphenylphosphino)ferrocene-palladium(II)dichloride dichloromethane complex (0.920 g, 1.127 mmol), bis(pinacolato)diboron (11.92 g, 47.0 mmol), and Example 36C (10 g, 18.78 mmol) in 1,2-dimethoxyethane (200 mL) was stirred at 80° C. for 6 hours. The reaction mixture was diluted with water and extracted with ethyl acetate (3×200 mL). The combined organic layers were washed with water and brine, dried over $Na_2SO_4$, filtered, concentrated, and recrystallized from ethyl acetate/petroleum ether (1:4) to give the title compound.

Example 36E tert-butyl 4-(4-(1-((tetrahydro-2H-pyran-4-yl)methyl)-1H-benzo[d][1,2,3]triazol-6-yl)-1-tosyl-1H-pyrrolo[2,3-b]pyridin-2-yl)-5,6-dihydropyridine-1(2H)-carboxylate A mixture of Example 36D (0.800 g, 1.380 mmol), 6-bromo-1-((tetrahydro-2H-pyran-4-yl)methyl)-1H-benzo[d][1,2,3]triazole (0.450 g, 1.519 mmol), $PdCl_2$(dppf)-$CH_2Cl_2$ adduct (0.045 g, 0.055 mmol), and aqueous sodium bicarbonate (6 mL, 1.380 mmol) in N,N-dimethylformamide (20 mL) was degassed and the mixture was heated at 80° C. for 2.5 hours. The reaction mixture was diluted with ethyl acetate and washed with aqueous $NaHCO_3$/brine and water, dried over $MgSO_4$, filtered, and purified on a 40 g column using the ISCO Companion flash system eluting with heptanes/ethyl acetate (4:6 to 3:7) to give the title compound.

Example 36F tert-butyl 4-(4-(1-((tetrahydro-2H-pyran-4-yl)methyl)-1H-benzo[d][1,2,3]triazol-6-yl)-1H-pyrrolo[2,3-b]pyridin-2-yl)-5,6-dihydropyridine-1(2H)-carboxylate A mixture of Example 36E (0.530 g, 0.792 mmol) and 5M aqueous sodium hydroxide (0.555 mL, 2.77 mmol) in dioxane (8 mL) was heated at 90° C. for 8 hours. The solvent was evaporated and the residue was treated with ethyl acetate and washed with aqueous NaHCO$_3$. The organic layer was dried over MgSO$_4$, filtered and concentrated until most of solvent was evaporated. The resulting precipitate was filtered, washed with ethyl acetate/ether, and vacuum oven-dried to give the title compound. The filtrate was concentrated and purified on a 4 g column using the ISCO Companion flash system eluting with ethyl acetate to give additional title compound.

Example 36G 1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole A solution of Example 36F (0.315 g, 0.612 mmol) in dichloromethane (8 mL) was treated with trifluoroacetic acid (0.472 mL, 6.12 mmol). The mixture was stirred for 16 hours at room temperature then heated at 40° C. for 4 hours. The reaction was concentrated and the residue was dissolved in 2 mL of methanol and treated slowly with 1.5 mL of 2M HCl in ether. The suspension was stirred for 15 minutes then diluted with ether. The solids were filtered, washed with ether, and vacuum oven dried to give the title compound as the hydrochloride salt. $^1$H NMR (400 MHz, methanol-d$_4$) δ ppm 1.41-1.60 (m, 4H), 2.33-2.50 (m, 1H), 2.80-2.95 (m, 2H), 3.40 (dd, J=11.4, 3.0 Hz, 1H), 3.51 (t, J=6.1 Hz, 2H), 3.87-4.01 (m, 4H), 4.74 (d, J=7.1 Hz, 2H), 6.55 (dt, J=3.5, 2.0 Hz, 1H), 6.91 (s, 1H), 7.53 (d, J=5.6 Hz, 1H), 7.88 (dd, J=8.7, 1.5 Hz, 1H), 8.11-8.28 (m, 2H), 8.40 (d, J=5.6 Hz, 1H). MS (ESI$^+$) m/z 415.2 (M+H)$^+$.

Example 37

1-[(5-fluoropyridin-3-yl)methyl]-6-[2-(piperidin-4-yl)-1H-pyrrolo[2,3-b]pyridin-4-yl]-1H-pyrrolo[3,2-b]pyridine Example 37A 6-bromo-1-((5-fluoropyridin-3-yl)methyl)-1H-pyrrolo[3,2-b]pyridine The title compound was prepared as described in Example 29A substituting 3-(chloromethyl)-5-fluoropyridine for 1-(bromomethyl)-3-fluorobenzene.

Example 37B

1-[(5-fluoropyridin-3-yl)methyl]-6-[2-(piperidin-4-yl)-1H-pyrrolo[2,3-b]pyridin-4-yl]-1H-pyrrolo[3,2-b]pyridine The title compound was prepared as described in Example 1H substituting Example 37A for Example 1G. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the tris-trifluoroacetate salt. $^1$H NMR (400 MHz, DMSO-d$_6$) δ ppm 1.80-1.95 (m, 2 H) 2.26 (d, J=11.90 Hz, 2 H) 3.01-3.18 (m, 3 H) 3.34-3.43 (m, 2 H) 5.66 (s, 2 H) 6.26 (s, 1 H) 6.76 (d, J=3.05 Hz, 1 H) 7.22 (d, J=4.88 Hz, 1 H) 7.55-7.61 (m, 1 H) 7.98 (d, J=3.05 Hz, 1 H) 8.25 (d, J=4.88 Hz, 1 H) 8.36 (s, 1 H) 8.45 (s, 1 H) 8.48 (d, J=2.75 Hz, 1 H) 8.61 (s, 1 H) 8.74-8.81 (m, 1 H) 11.58 (s, 1 H). MS (ESI) m/e 427 (M+H)$^+$.

Example 38

2-hydroxy-1-[4-{4-[1-(tetrahydro-2H-pyran-4-ylmethyl)-1H-benzotriazol-6-yl}-1H-pyrrolo[2,3-b]pyridin-2-yl]-3,6-dihydropyridin-1(2H)-yl]ethanone A mixture of Example 36G (75.0 mg, 0.154 mmol), (benzotriazol-1-yloxy)tripyrrolidinophosphonium hexafluorophosphate (PyBOP) (96 mg, 0.185 mmol), triethylamine (86 μL, 0.615 mmol), and 2-hydroxyacetic acid (70% in water) (11.23 μL, 0.185 mmol) was stirred for 16 hours at room temperature. The reaction mixture was treated with brine and aqueous NaHCO$_3$ and extracted with ethyl acetate (twice). The combined organic layers were dried over MgSO$_4$, filtered, concentrated, and purified by HPLC (see protocols in Example 15) to give the title compound as a trifluoroacetic acid salt. $^1$H NMR (400 MHz, methanol-d$_4$) δ ppm 1.42-1.60 (m, 4H), 2.31-2.47 (m, 1H), 2.61-2.75 (m, 2H), 3.40 (dd, J=11.5, 2.9 Hz, 2H), 3.67 (t, J=5.7 Hz, 1H), 3.80-3.99 (m, 3H), 4.21 (d, J=3.7 Hz, 1H), 4.24-4.35 (m, 3H), 4.74 (d, J=7.1 Hz, 2H), 6.48-6.58 (m, 1H), 6.86 (d, J=8.6 Hz, 1H), 7.51-7.57 (m, 1H), 7.88 (dd, J=8.6, 1.4 Hz, 1H), 8.20 (d, J=8.6 Hz, 1H), 8.22-8.26 (m, 1H), 8.36 (d, J=5.6 Hz, 1H). MS (ESI$^+$) m/z 473.2 (M+H)$^+$.

Example 39

6-{2-[1-(methylsulfonyl)-1,2,3,6-tetrahydropyridin-4-yl]-1H-pyrrolo[2,3-b]pyridin-4-yl}-1-(tetrahydro-2H-pyran-4-ylmethyl)-1H-benzotriazole To a solution of Example 36G (75.0 mg, 0.154 mmol) in N,N-dimethylformamide (2 mL) was added methanesulfonyl chloride (0.024 mL, 0.308 mmol) and triethylamine (0.129 mL, 0.923 mmol). The reaction was stirred at room temperature for 3 hours. The reaction mixture was treated with water. The resulting solids were filtered, washed with water, and purified by HPLC (see protocols in Example 15) to give the title compound as a trifluoroacetic acid salt. $^1$H NMR (400 MHz, methanol-d$_4$) δ ppm 1.42-1.60 (m, 4H), 2.31-2.47 (m, 1H), 2.72-2.80 (m, 2H), 2.92 (s, 3H), 3.40 (dd, J=11.4, 2.9 Hz, 2H), 3.54 (t, J=5.7 Hz, 2H), 3.90-3.98 (m, 2H), 4.03-4.08 (m, 2H), 4.75 (d, J=7.1 Hz, 2H), 6.54-6.60 (m, 1H), 6.89 (s, 1H), 7.58 (d, J=5.8 Hz, 1H), 7.89 (dd, J=8.6, 1.4 Hz, 1H), 8.21 (d, J=8.6 Hz, 1H), 8.26 (s, 1H), 8.37 (d, J=5.7 Hz, 1H). MS (ESI$^+$) m/z 493.1 (M+H)$^+$.

Example 40

1-(3-fluorobenzyl)-6-[2-(1,2,3,6-tetrahydropyridin-4-yl)-1H-pyrrolo[2,3-b]pyridin-4-yl]-1H-pyrrolo[3,2-b]pyridine The title compound was prepared as described in Example 14D-14E substituting Example 29A for Example 2C. The reaction mixture was concentrated, triturated with diethyl ether and dried to afford the title compound as the bis-trifluoroacetate salt. $^1$H NMR (400 MHz, DMSO-d$_6$) δ ppm 2.67-2.74 (m, 2 H) 3.37 (t, J=6.10 Hz, 2 H) 3.85 (m, 2 H) 5.61 (s, 2 H) 6.45-6.52 (m, 1 H) 6.57 (s, 1 H) 6.76 (d, J=3.36 Hz, 1 H) 7.04-7.13 (m, 3 H) 7.24 (d, J=4.88 Hz, 1 H) 7.34-7.41 (m, 1 H) 7.97 (d, J=3.05 Hz, 1 H) 8.28-8.35 (m, 2 H) 8.80 (d, J=1.83 Hz, 1 H) 8.86-8.90 (m, 1 H) 11.85 (s, 1 H). MS (ESI) m/e 424 (M+H)$^+$.

Example 41 methyl 5-fluoro-1-(3-fluorobenzyl)-6-[2-(piperidin-4-yl)-1H-pyrrolo[2,3-b]pyridin-4-yl]-1H-indole-3-carboximidate

Example 41A 6-bromo-5-fluoro-1-(3-fluorobenzyl)-1H-indole-3-carbonitrile

The title compound was prepared as described in Example 28A using 6-bromo-5-fluoro-1H-indole-3-carbonitrile in place of 6-bromo-1H-pyrrolo[3,2-b]pyridine-3-carbonitrile and using 1-(bromomethyl)-3-fluorobenzene in place of 4-(bromomethyl)tetrahydro-2H-pyran.

Example 41B tert-butyl 4-(4-(3-cyano-5-fluoro-1-(3-fluorobenzyl)-1H-indol-6-yl)-1H-pyrrolo[2,3-b]pyridin-2-yl)piperidine-1-carboxylate The title compound was prepared as described in Example 28B using Example 41A in place of Example 28A.

Example 41C methyl 5-fluoro-1-(3-fluorobenzyl)-6-[2-(piperidin-4-yl)-1H-pyrrolo[2,3-b]pyridin-4-yl]-1H-indole-3-carboximidate Example 41B (120 mg, 0.211 mmol) in 1 mL of dichloromethane and 1 mL of methanol was cooled to 0° C. and 5 mL of 2 M hydrochloric acid in ether was added. The cooling bath was removed and the reaction was stirred at ambient temperature for 2 hours. The reaction mixture was concentrated and the residue was purified by reverse-phase HPLC (Phenomenex Luna C8(2) 100 Å AXIA column) using a gradient of 10-95% acetonitrile/0.1% trifluoroacetic acid in water to afford the title compound as a bis trifluoroacetic acid salt. $^1$H NMR (400 MHz, Methanol-$d_4$) δ ppm 1.87-2.02 (m, 2H), 2.26-2.37 (m, 2H), 3.10-3.27 (m, 3H), 3.48-3.61 (m, 2H), 4.42 (s, 3H), 5.66 (s, 2H), 6.21 (s, 1H), 7.04-7.14 (m, 3H), 7.37-7.44 (m, 2H), 7.85 (d, J=5.8 Hz, 1H), 7.95 (d, J=11.0 Hz, 1H), 8.29-8.36 (m, 1H), 8.68 (s, 1H). MS (ESI$^+$) m/z 500.4 (M+H)$^+$.

Example 42

5-fluoro-1-(3-fluorobenzyl)-6-[2-(piperidin-4-yl)-1H-pyrrolo[2,3-b]pyridin-4-yl]-1H-indole-3-carbonitrile Example 41B (120 mg, 0.211 mMol) in 1 mL of dichloromethane and 1 mL of methanol was cooled to 0° C. and 5 mL of 2 M hydrochloric acid in ether was added. The cooling bath was removed and the reaction was stirred at ambient temperature for 2 hours. The reaction mixture was concentrated and the residue was purified by reverse-phase HPLC (Phenomenex Luna C8(2) 100 Å AXIA column) using a gradient of 10-95% acetonitrile/0.1% trifluoroacetic acid in water to afford the title compound as a bis trifluoroacetic acid salt. $^1$H NMR (400 MHz, Methanol-$d_4$) δ ppm 1.84-2.01 (m, 2H), 2.25-2.36 (m, 2H), 3.14-3.28 (m, 3H), 3.48-3.60 (m, 2H), 5.59 (s, 2H), 6.23 (d, J=1.8 Hz, 1H), 6.96-7.14 (m, 3H), 7.30-7.48 (m, 2H), 7.64 (d, J=10.2 Hz, 1H), 7.76 (d, J=5.8 Hz, 1H), 8.26-8.40 (m, 2H). MS (ESI$^+$) m/z 468.4 (M+H)$^+$.

Example 43

1'-(3-fluorobenzyl)-2-(piperidin-4-yl)-1H,1'H-4,6'-bipyrrolo[2,3-b]pyridine

Example 43A 6-bromo-1-(3-fluorobenzyl)-1H-pyrrolo[2,3-b]pyridine

The title compound was prepared as described in Example 29A substituting 6-bromo-1H-pyrrolo[2,3-b]pyridine for 6-bromo-1H-pyrrolo[3,2-b]pyridine.

Example 43B

1'-(3-fluorobenzyl)-2-(piperidin-4-yl)-1H,1'H-4,6'-bipyrrolo[2,3-b]pyridine

The title compound was prepared as described in Example 1H substituting Example 43A for Example 1G. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (400 MHz, DMSO-$d_6$) δ ppm 1.74-1.99 (m, 2 H) 2.15-2.28 (m, 2 H) 2.99-3.19 (m, 3 H) 3.32-3.45 (m, 2 H) 5.62 (s, 2 H) 6.61 (d, J=3.36 Hz, 1 H) 6.83 (s, 1 H) 6.98-7.14 (m, 3 H) 7.31-7.40 (m, 1 H) 7.60 (d, J=5.19 Hz, 1 H) 7.68 (d, J=3.66 Hz, 1 H) 7.81 (d, J=8.24 Hz, 1 H) 8.13 (d, J=8.24 Hz, 1 H) 8.25 (d, J=5.19 Hz, 1 H) 8.69 (s, 1 H) 11.54 (s, 1 H). MS (ESI) m/e 426 (M+H)$^+$.

Example 44

2-(piperidin-4-yl)-1'-(tetrahydro-2H-pyran-4-ylmethyl)-1H,1'H-4,6'-bipyrrolo[2,3-b]pyridine

Example 44A 6-bromo-1-((tetrahydro-2H-pyran-4-yl)methyl)-1H-pyrrolo[2,3-b]pyridine The title compound was prepared as described in Example 43A substituting 4-(bromomethyl)tetrahydro-2H-pyran for 1-(bromomethyl)-3-fluorobenzene.

Example 44B 2-(piperidin-4-yl)-1'-(tetrahydro-2H-pyran-4-ylmethyl)-1H,1'H-4,6'-bipyrrolo[2,3-b]pyridine The title compound was prepared as described in Example 1H substituting Example 44A for Example 1G. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (400 MHz, DMSO-$d_6$) δ ppm 1.28-2.39 (m, 9 H) 3.03-3.45 (m, 7 H) 3.80-3.89 (m, 2 H) 4.30 (d, J=7.32 Hz, 2 H) 6.54 (d, J=3.36 Hz, 1 H) 7.00 (s, 1 H) 7.52-7.66 (m, 2 H) 7.79 (d, J=7.93 Hz, 1 H) 8.09 (d, J=7.93 Hz, 1 H) 8.26 (d, J=5.19 Hz, 1 H) 8.67 (s, 1 H) 11.56 (s, 1 H). MS (ESI) m/e 416 (M+H)+.

Example 45

4-{4-[1-(3-fluorobenzyl)-1H-pyrrolo[3,2-b]pyridin-6-yl]-1H-pyrrolo[2,3-b]pyridin-2-yl}-N-methylpiperidine-1-carboxamide To Example 29B (30 mg, 0.047 mmol) in 0.6 mL N,N-dimethylformamide were added triethylamine (0.033 mL, 0.235 mmol) and isocyanatomethane (4.02 mg, 0.071 mmol). The mixture was stirred at room temperature for 1 hour and concentrated. The residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the trifluoroacetate salt. $^1$H NMR (400 MHz, DMSO-$d_6$) δ ppm 1.51-1.66 (m, 2 H) 1.89-1.99 (m, 2H) 2.62 (s, 3 H) 2.71-2.98 (m, 3 H) 3.99-4.10 (m, 2 H) 5.67 (s, 2 H) 6.17 (s, 1 H) 6.85 (d, J=2.44 Hz, 1 H) 7.05-7.17 (m, 3 H) 7.25 (d, J=5.19 Hz, 1 H) 7.33-7.44 (m, 1 H) 8.14 (d, J=3.05 Hz, 1 H) 8.24 (d, J=4.88 Hz, 1 H) 8.56 (s, 1 H) 8.85 (d, J=1.53 Hz, 1 H) 11.59 (s, 1 H). MS (ESI) m/e 483 (M+H)+.

Example 46

6-{2-[1-(methylsulfonyl)piperidin-4-yl]-1H-pyrrolo[2,3-b]pyridin-4-yl}-1-(tetrahydro-2H-pyran-4-ylmethyl)-1H-pyrrolo[3,2-b]pyridine To Example 30B (35 mg, 0.084 mmol) in 1 mL N,N-dimethylformamide were added methanesulfonyl chloride (0.012 mL, 0.152 mmol) and triethylamine (0.070 mL, 0.505 mmol). The mixture was stirred at room temperature for 2 hours. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the trifluoroacetate salt. $^1$H NMR (400 MHz, DMSO-$d_6$) δ ppm 1.29-1.49 (m, 4 H) 1.74-1.89 (m, 2 H) 2.08-2.22 (m, 3 H) 2.87 (s, 3 H) 2.88-3.00 (m, 3 H) 3.20-3.32 (m, 2 H) 3.63-3.88 (m, 4 H) 4.29 (d, J=7.02 Hz, 2 H) 6.43 (s, 1 H) 6.75 (d, J=3.97 Hz, 1 H) 7.29 (d, J=4.88 Hz, 1 H) 7.94 (d, J=3.36 Hz, 1 H) 8.27 (d, J=5.19 Hz, 1 H) 8.58 (s, 1 H) 8.82 (d, J=1.83 Hz, 1 H) 11.59 (s, 1 H). MS (ESI) m/e 494 (M+H)+.

Example 47

4-(4-{1-[(5-fluoropyridin-3-yl)methyl]-1H-pyrrolo[3,2-b]pyridin-6-yl}-1H-pyrrolo[2,3-b]pyridin-2-yl)-N-methylpiperidine-1-carboxamide The title compound was prepared as the bis-trifluoroacetate salt as described in Example 45 substituting Example 37B for Example 29B. $^1$H NMR (400 MHz, DMSO-$d_6$) δ ppm 1.53-1.68 (m, 2H) 1.90-2.01 (m, 2 H) 2.61 (s, 3 H) 2.76-3.00 (m, 3 H) 3.98-4.10 (m, 2 H) 5.74 (s, 2 H) 6.22 (s, 1 H) 6.86 (d, J=3.36 Hz, 1 H) 7.27 (d, J=4.88 Hz, 1 H) 7.57-7.67 (m, 1 H) 8.17 (d, J=3.36 Hz, 1 H) 8.25 (d, J=4.88 Hz, 1 H) 8.40-8.54 (m, 2 H) 8.65 (s, 1 H) 8.86 (d, J=1.83 Hz, 1 H) 11.60 (s, 1 H). MS (ESI) m/e 484 (M+H)+.

Example 48

1-[(5-fluoropyridin-3-yl)methyl]-6-{2-[1-(methylsulfonyl)piperidin-4-yl]-1H-pyrrolo[2,3-b]pyridin-4-yl}-1H-pyrrolo[3,2-b]pyridine The title compound was prepared as the bis-trifluoroacetate salt as described in Example 46 substituting Example 37B for Example 30B. $^1$H NMR (400 MHz, DMSO-$d_6$) δ ppm 1.72-1.86 (m, 2H) 2.07-2.17 (m, 2 H) 2.88 (s, 3 H) 2.89-2.95 (m, 3 H) 3.64-3.77 (m, 2 H) 5.73 (s, 2 H) 6.27 (s, 1 H) 6.85 (d, J=3.36 Hz, 1 H) 7.27 (d, J=4.88 Hz, 1 H) 7.57-7.66 (m, 1 H) 8.15 (d, J=3.36 Hz, 1 H) 8.26 (d, J=4.88 Hz, 1 H) 8.43-8.51 (m, 2 H) 8.62 (s, 1 H) 8.85 (d, J=1.53 Hz, 1 H) 11.63 (s, 1 H). MS (ESI) m/e 505 (M+H)+.

Example 49

1'-[(5-fluoropyridin-3-yl)methyl]-2-(piperidin-4-yl)-1H,1'H-4,6'-bipyrrolo[2,3-b]pyridine Example 49A 6-bromo-1-((5-fluoropyridin-3-yl)methyl)-1H-pyrrolo[2,3-b]pyridine The title compound was prepared as described in Example 43A substituting 3-(chloromethyl)-5-fluoropyridine for 1-(bromomethyl)-3-fluorobenzene.

Example 49B

1'-[(5-fluoropyridin-3-yl)methyl]-2-(piperidin-4-yl)-1H,1'H-4,6'-bipyrrolo[2,3-b]pyridine The title compound was prepared as described in Example 1H substituting Example 49A for Example 1G. The reaction mixture was concentrated and the residue was purified by reverse-phase HPLC performed on a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (400 MHz, DMSO-$d_6$) δ ppm 1.79-1.94 (m, 2 H) 2.20-2.30 (m, 2 H) 2.99-3.23 (m, 3 H) 3.32-3.45 (m, 2 H) 5.68 (s, 2 H) 6.62 (d, J=3.36 Hz, 1 H) 6.80 (s, 1 H) 7.50-7.59 (m, 1 H) 7.61 (d, J=5.19 Hz, 1 H) 7.75 (d, J=3.66 Hz, 1 H) 7.82 (d, J=8.24 Hz, 1 H) 8.14 (d, J=8.24 Hz, 1 H) 8.26 (d, J=5.19 Hz, 1 H) 8.40-8.52 (m, 2 H) 8.61 (s, 1 H) 11.57 (s, 1 H). MS (ESI) m/e 427 (M+H)+.

Example 50

1-[(5-fluoropyridin-3-yl)methyl]-6-[2-(1,2,3,6-tetrahydropyridin-4-yl)-1H-pyrrolo[2,3-b]pyridin-4-yl]-1H-pyrrolo[3,2-b]pyridine The title compound was prepared as described in Example 14D-14E substituting Example 37A for Example 2C. The reaction mixture was concentrated, triturated with diethyl ether and dried to afford the title compound as the bis-trifluoroacetate salt. $^1$H NMR (400 MHz, DMSO-$d_6$) δ ppm 2.70-2.77 (m, 2 H) 3.38 (t, J=6.10 Hz, 2 H) 3.82-3.86 (m, 2 H) 5.68 (s, 2 H) 6.45-6.54 (m, 1 H) 6.59 (s, 1 H) 6.78 (d, J=3.36 Hz, 1 H) 7.25 (d, J=5.19 Hz, 1 H) 7.54-7.65 (m, 1 H) 8.01 (d, J=3.05 Hz, 1 H) 8.31 (d, J=4.88 Hz, 1 H) 8.37-8.49 (m, 3 H) 8.80 (d, J=1.83 Hz, 1 H) 8.86-8.97 (m, 1 H) 11.86 (s, 1 H). MS (ESI) m/e 425 (M+H)+.

Example 51

1'-[(5-fluoropyridin-3-yl)methyl]-2-(1,2,3,6-tetrahydropyridin-4-yl)-1H,1'H-4,6'-bipyrrolo[2,3-b]pyridine The title compound was prepared as described in Example 14D-14E substituting Example 49A for Example 2C. The reaction mixture was concentrated, triturated with diethyl ether and dried to afford the title compound as the bis-trifluoroacetate salt. $^1$H NMR (400 MHz, DMSO-$d_6$) δ ppm 2.62-2.77 (m, 2 H) 3.36 (t, J=6.10 Hz, 2 H) 3.79-3.90 (m, 2 H) 5.70 (s, 2 H) 6.49 (s, 1 H) 6.63 (d, J=3.36 Hz, 1 H) 7.12 (s, 1 H) 7.51-7.57 (m, 1 H) 7.60 (d, J=5.19 Hz, 1 H) 7.75 (d, J=3.66 Hz, 1 H) 7.84 (d, J=8.24 Hz, 1 H) 8.15 (d, J=8.24 Hz, 1 H) 8.31 (d, J=4.88 Hz, 1 H) 8.39-8.53 (m, 2 H) 8.91 (s, br, 2 H) 11.77 (s, 1 H). MS (ESI) m/e 425 (M+H)$^+$.

Example 52

4-{1'-[(5-fluoropyridin-3-yl)methyl]-1H,1'H-4,6'-bipyrrolo[2,3-b]pyridin-2-yl}-N-methylpiperidine-1-carboxamide The title compound was prepared as the bis-trifluoroacetate salt as described in Example 45 substituting Example 49B for Example 29B. $^1$H NMR (400 MHz, DMSO-$d_6$) δ ppm 1.50-1.67 (m, 2 H) 1.89-2.02 (m, 2 H) 2.61 (s, 3 H) 2.75-3.03 (m, 3 H) 3.98-4.08 (m, 2 H) 5.67 (s, 2 H) 6.62 (d, J=3.66 Hz, 1 H) 6.76 (s, 1 H) 7.50-7.63 (m, 2 H) 7.74 (d, J=3.36 Hz, 1 H) 7.82 (d, J=7.93 Hz, 1 H) 8.14 (d, J=8.24 Hz, 1 H) 8.23 (d, J=5.19 Hz, 1 H) 8.38-8.49 (m, 2 H) 11.51 (s, 1 H). MS (ESI) m/e 484 (M+H)$^+$.

Example 53

1'-[(5-fluoropyridin-3-yl)methyl]-2-[1-(methylsulfonyl)piperidin-4-yl]-1H,1'H-4,6'-bipyrrolo[2,3-b]pyridine The title compound was prepared as the bis-trifluoroacetate salt as described in Example 46 substituting Example 49B for Example 30B. $^1$H NMR (400 MHz, DMSO-$d_6$) δ ppm 1.66-1.87 (m, 2 H) 2.01-2.20 (m, 2 H) 2.85-2.98 (m, 3 H) 2.87 (s, 3 H) 3.66-3.76 (m, 2 H) 5.68 (s, 2 H) 6.62 (d, J=3.36 Hz, 1 H) 6.80 (s, 1 H) 7.52-7.63 (m, 2 H) 7.74 (d, J=3.66 Hz, 1 H) 7.83 (d, J=8.24 Hz, 1 H) 8.14 (d, J=8.24 Hz, 1 H) 8.24 (d, J=5.19 Hz, 1 H) 8.39-8.52 (m, 2 H) 11.52 (s, 1 H). MS (ESI) m/e 505 (M+H)$^+$.

Example 54

4-{1'-[(5-fluoropyridin-3-yl)methyl]-1H,1'H-4,6'-bipyrrolo[2,3-b]pyridin-2-yl}-N-methyl-3,6-dihydropyridine-1(2H)-carboxamide The title compound was prepared as the bis-trifluoroacetate salt as described in Example 45 substituting Example 51 for Example 29B. $^1$H NMR (400 MHz, DMSO-$d_6$) δ ppm 2.39-2.46 (m, 2 H) 2.63 (s, 3 H) 3.53 (t, J=5.80 Hz, 2 H) 3.99-4.07 (m, 2 H) 5.69 (s, 2 H) 6.46-6.53 (m, 1 H) 6.63 (d, J=3.66 Hz, 1 H) 7.05 (s, 1 H) 7.51-7.63 (m, 2 H) 7.74 (d, J=3.66 Hz, 1 H) 7.85 (d, J=8.24 Hz, 1 H) 8.15 (d, J=8.24 Hz, 1 H) 8.27 (d, J=5.19 Hz, 1 H) 8.41-8.47 (m, 2 H) 11.66 (s, 1 H). MS (ESI) m/e 482 (M+H)$^+$.

Example 55

1'-[(5-fluoropyridin-3-yl)methyl]-2-[1-(methylsulfonyl)-1,2,3,6-tetrahydropyridin-4-yl]-1H,1'H-4,6'-bipyrrolo[2,3-b]pyridine The title compound was prepared as the bis-trifluoroacetate salt as described in Example 46 substituting Example 51 for Example 30B. $^1$H NMR (400 MHz, DMSO-$d_6$) δ ppm 2.53-2.62 (m, 2 H) 2.92 (s, 3 H) 3.43 (t, J=5.80 Hz, 2 H) 3.91-3.97 (m, 2 H) 5.69 (s, 2 H) 6.44-6.57 (m, 1 H) 6.63 (d, J=3.36 Hz, 1 H) 7.07 (s, 1 H) 7.50-7.63 (m, 2 H) 7.74 (d, J=3.36 Hz, 1 H) 7.85 (d, J=8.24 Hz, 1 H) 8.14 (d, J=8.24 Hz, 1 H) 8.28 (d, J=5.19 Hz, 1 H) 8.38-8.49 (m, 2 H) 11.67 (s, 1 H). MS (ESI) m/e 503 (M+H)$^+$.

Example 56

1'-[(5-fluoropyridin-3-yl)methyl]-2-(1,2,5,6-tetrahydropyridin-3-yl)-1H,1'H-4,6'-bipyrrolo[2,3-b]pyridine

Example 56A tert-butyl 3-(4-chloro-1-tosyl-1H-pyrrolo[2,3-b]pyridin-2-yl)-5,6-dihydropyridine-1(2H)-carboxylate The title compound was prepared as described in Example 14A substituting tert-butyl 3-(4,4,5,5-tetramethyl-1,3,2-dioxaborolan-2-yl)-5,6-dihydropyridine-1(2H)-carboxylate for tert-butyl 4-(4,4,5,5-tetramethyl-1,3,2-dioxaborolan-2-yl)-5,6-dihydropyridine-1(2H)-carboxylate.

Example 56B tert-butyl 3-(1'-((5-fluoropyridin-3-yl)methyl)-1-tosyl-1H,1'H-[4,6'-bipyrrolo[2,3-b]pyridin]-2-yl)-5,6-dihydropyridine-1(2H)-carboxylate A pressure vial was charged with Example 56A (200 mg, 0.410 mmol), Pd$_2$(dba)$_3$ (18.76 mg, 0.020 mmol), dicyclohexyl(2',4',6'-triisopropyl-[1,1'-biphenyl]-2-yl)phosphine (39.1 mg, 0.082 mmol), 4,4,4',4',5,5,5',5'-octamethyl-2,2'-bi(1,3,2-dioxaborolane) (104 mg, 0.410 mmol) and potassium acetate (80 mg, 0.820 mmol). The flask was capped, evacuated and backfilled with nitrogen. Dioxane (5 mL) was added and the reaction was stirred at 105° C. for 2 hours. Example 49A (125 mg, 0.410 mmol) was added followed by aqueous K$_3$PO$_4$ solution (5 M, 0.410 mL, 2.049 mmol) and the mixture was heated at 105 C for 2.5 hours. The reaction mixture was filtered through diatomaceous earth, concentrated and purified by flash chromatography on Analogix IntelliFlash$^{280}$ eluting with 2 to 15% methanol/dichloromethane to give the title compound.

Example 56C

1'-[(5-fluoropyridin-3-yl)methyl]-2-(1,2,5,6-tetrahydropyridin-3-yl)-1H,1'H-4,6'-bipyrrolo[2,3-b]pyridine To a solution of Example 56B (470 mg, ~0.55 mmol) in 5 mL tetrahydrofuran and 3.5 mL methanol was added aqueous sodium hydroxide (1 M, 2.08 mL, 2.08 mmol). The reaction mixture was stirred at room temperature for 16 hours and concentrated. To the residue was added 2 mL dichloromethane and 1 mL trifluoroacetic acid. The mixture was stirred at room temperature for 40 minutes. The reaction was concentrated then purified by reverse-phase HPLC performed on a Phenomenex Luna C8 AXIA column (30×75 mm, 100 Å) using a gradient of 10% to 95% acetonitrile:10 mM ammonium acetate in water to afford the title compound. $^1$H NMR (400 MHz, DMSO-$d_6$) δ ppm 2.24-2.36 (m, 2 H) 2.97 (t, J=5.65 Hz, 2 H) 3.66-3.71 (m, 2 H) 5.70 (s, 2 H) 6.60-6.69 (m, 2 H) 7.03 (s, 1 H) 7.54-7.69 (m, 2 H) 7.83 (d, J=3.36 Hz, 1 H) 7.88 (d, J=8.24 Hz, 1 H) 8.17 (d, J=8.24 Hz, 1 H) 8.28 (d, J=5.19 Hz, 1 H) 8.41-8.56 (m, 2 H) 11.86 (s, 1 H). MS (ESI) m/e 425 (M+H)$^+$.

BIOLOGICAL EXAMPLES

CDK9 Enzyme Protocol

CDK9 enzyme activities were measured using LANCE ULight TR-FRET kinase assay reagents (PerkinElmer, Waltham, Mass.). Compounds were directly added in 100% DMSO to white low volume assay plates (Perkin Elmer Proxiplate 6008289) using a Labcyte Echo acoustic dispenser. Assay reagents in serine/threonine kinase assay buffer containing 20 mM HEPES, 10 mM $MgCl_2$, 100 mM $Na_3VO_4$, and 0.0075% Triton X-100. were added for final reaction mixture concentrations of 1000 μM ATP, 100 nM U-light MBP peptide (Perkin Elmer TRF0109M) and reaction initiated with 4 nM CDK9/Cyclin T1 (Carna Biosciences 04-110). The kinase reaction was carried out for 30 minutes before addition of stopping buffer to a final of 20 mM EDTA and 0.5 nM of LANCE Ultra Europium anti-phospho-MBP antibody (PerkinElmer TRF0201M) in LANCE detection buffer (PerkinElmer CR97-100). The reaction was equilibrated for 1 hour and the signal read in the Perkin Elmer Envision in TR-FRET mode (excitation at 320 nm and emission at 615/665 nm).

Cell Viability Protocol

Cell viability assays were performed using A431 or H929 cells. A431 cells were seeded in 96-well plates at 10,000 cells/well, and after overnight incubation, treated with compounds at 2-times the final concentration to result in a dose response of 3-fold dilutions from 10 μM to 0.0005 μM (50 μL/well, 0.1% final DMSO concentration). H929 cells were seeded in 96-well plates at 10,000 cells/well and treated immediately with compounds as described above. After 24 hours at 37° C., cell viability was measured using Cell Titer-Glo reagent (Promega) with a luminescence reader. Alternately, cell viability assays were performed in 384-well format. A431 cells were seeded in 384-well plates at 2500 cells/well and, after overnight incubation, treated with compounds in a dose response of 3-fold dilutions from 10 μM to 0.0005 μM (25 mL/well, 0.1% final DMSO concentration). For the H929 viability assay, 25 mL/well of the compounds was dispensed into 384-well plates in a dose response as described above and cells were immediately seeded in 384-well plates at 2500 cells/well. After 24 hours at 3TC, cell viability was measured using Cell TiterGlo reagent (Promega) with a luminescence reader. The results are reported in Table 1.

TABLE 1

| EXAMPLE | CDK9 $IC_{50}$ (μM) | A431 viability $EC_{50}$ (μM) | H929 viability $EC_{50}$ (μM) |
|---|---|---|---|
| 1 | 0.064 | 0.55 | 0.49 |
| 2 | 0.009 | 0.012 | 0.044 |
| 3 | 0.024 | 0.024 | 0.079 |
| 4 | 0.024 | 0.009 | 0.015 |
| 5 | 0.04 | ND | 0.18 |
| 6 | 0.038 | ND | 0.13 |
| 7 | 0.069 | ND | 0.5 |
| 8 | 0.018 | 0.052 | 0.072 |
| 9 | 0.05 | 0.11 | 0.1 |
| 10 | 0.018 | 0.071 | 0.0523 |
| 11 | 0.11 | ND | 0.178 |
| 12 | 0.03 | 0.13 | 0.075 |
| 13 | 0.026 | 0.583 | 0.029 |
| 14 | 0.014 | 0.004 | 0.007 |
| 15 | 0.043 | 0.006 | 0.007 |
| 16 | 0.094 | ND | 0.18 |
| 17 | 0.066 | ND | 0.12 |
| 18 | 0.12 | ND | 0.858 |
| 19 | 0.097 | ND | 1.11 |
| 20 | 0.16 | ND | 1.97 |
| 21 | 0.1 | ND | 1.85 |
| 22 | 0.016 | ND | 0.1 |
| 23 | 0.055 | ND | 0.55 |
| 24 | 0.035 | 0.013 | 0.027 |
| 25 | 0.019 | 0.043 | 0.049 |
| 26 | 0.043 | 0.006 | 0.026 |
| 27 | 0.053 | ND | 7.0 |
| 28 | 0.18 | ND | >10 |
| 29 | 0.028 | 0.033 | 0.087 |
| 30 | 0.085 | ND | 6.3 |
| 31 | 0.030 | ND | ND |
| 32 | 0.051 | ND | 0.89 |
| 33 | 0.018 | ND | 1.1 |
| 34 | 0.017 | ND | 0.13 |
| 35 | 0.013 | ND | 0.2 |
| 36 | 0.059 | ND | 0.45 |
| 37 | 0.026 | ND | 0.17 |
| 38 | 0.062 | ND | 0.44 |
| 39 | 0.074 | ND | 0.20 |
| 40 | 0.017 | ND | 0.053 |
| 41 | 0.091 | ND | 0.59 |
| 42 | 0.055 | ND | 0.21 |
| 43 | 0.026 | ND | 0.15 |
| 44 | 0.044 | ND | 1.1 |
| 45 | 0.03 | ND | 0.12 |
| 46 | 0.14 | ND | 1.8 |
| 47 | 0.023 | ND | 0.6 |
| 48 | 0.035 | ND | 0.54 |
| 49 | 0.024 | ND | 0.25 |
| 50 | 0.017 | ND | 0.12 |
| 51 | 0.014 | 0.011 | 0.090 |
| 52 | 0.011 | ND | 1.1 |
| 53 | 0.008 | ND | 1.4 |
| 54 | 0.027 | ND | 0.21 |
| 55 | 0.065 | ND | 0.37 |
| 56 | 0.029 | ND | 0.25 |

ND = not determined

Xenograft Tumor Growth Inhibition Assay

The effect of Examples 1, 4, and 5 to inhibit the growth of H929 xenograft tumors implanted in mice was evaluated. NCI-H929 cells obtained from culture were suspended in cell culture medium (MEM, no calcium, no glutamine, Life Technologies Corporation) and diluted 1:1 with a solution of Matrigel™ (BD Biosciences, Franklin Lakes, N.J.). Tumor cells 5 million per site were inoculated subcutaneously into the right hind flank of female nude or SCID-beige mice (Charles River Labs).

Randomization into treatment and vehicle control groups (9-10/group) occurred when the mean tumor volume reached approximately 200 $mm^3$ Compounds were formulated in 2% DMSO, 5% Tween80, 20% PEG400, 73% HPMC. Administration of compound or vehicle was initiated on the day following randomization and continued for the indicated time. Tumors were measured twice a week throughout the treatment period using a pair of calipers and tumor volumes were calculated according to the formula V=L×$W^2$/2 (V: volume, $mm^3$; L: length, mm. W: width, m). Tumor growth inhibition was calculated based on the mean tumor volume measured at the end of the treatment period according to the formula % TGI=100−mean tumor volume of treatment group/mean tumor volume of control group×100. Results are given in Table 2.

TABLE 2

H929 human multiple myeloma cancer xenograft model.

| Example | Dose mg/kg | route, regimen | % TGI[a] | % TGD[b] | % removed from study[c] |
|---|---|---|---|---|---|
| 1 | 3.75 | IP, TW[d] × 3 | 64** | 55 | 0 |
| 1 | 7.50 | IP, TW × 3 | 66*** | 66*** | 11 |
| 4 | 3.75 | IP, TW × 3 | 25 | 5 | 0 |
| 4 | 7.50 | IP, TW × 3 | 62** | 42*** | 11 |
| 5 | 7.50 | IP, TW × 3 | 39 | 20 | 22 |
| 5 | 15 | IP, TW × 3 | 58** | 31** | 11 |

[a]The p values (as indicated by asterisks) are derived from Student's T test comparison of treatment group vs. control group:
*p < 0.05,
**p < 0.01,
***p < 0.001.
[b]Tumor growth delay, % TGD = (T − C)/C × 100, where T = median time to reach 500 mm³ of treatment group and C = median time to endpoint of control group. The p values (as indicated by asterisks) derived from Kaplan Meier log-rank comparison of treatment group vs. treatment control group based on an endpoint of 1000 mm³.
*p < 0.05,
**p < 0.01,
***p < 0.001.
[c]Percentage of treatment group that were removed from study due to morbidity or weight loss in excess of 20%.
[d]Twice a week, 3 and 4 days apart.

It is understood that the examples and embodiments described herein are for illustrative purposes only and that various modifications or changes in light thereof will be suggested to persons skilled in the art and are to be included within the spirit and purview of the appended claims. All publications, patents, and patent applications cited herein are hereby incorporated by reference in their entirety for all purposes.

What is claimed is:
1. A compound having Formula (Ia), or a pharmaceutically acceptable salt thereof,

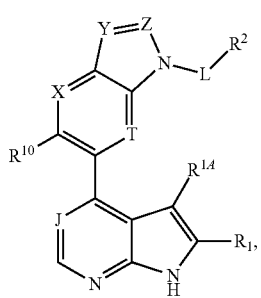

(Ia)

wherein
the bond between Y and Z is a single or a double bond;
wherein if the bond is a double bond then Y is N or $CR^3$, and Z is N or CH; wherein if the bond is a single bond, then Y is $CH_2$ and Z is $CH_2$;
J, X, and T are each independently N or $CR^3$;
$R^3$ is selected from the group consisting of: H, $C_1$-$C_6$ alkyl, halo, CN, and $C(N)OR^{3A}$;
$R^{3A}$ is $C_1$-$C_5$ alkyl;
L is absent or is a $C_1$-$C_5$ alkylene;
$R^{1A}$ is H, $C_1$-$C_6$ alkyl, CN, or halo;
$R^2$ is H, phenyl, a 4 to 7 membered heterocycloalkyl, or a five to six membered heteroaryl;
each of which may substituted with one to three substituents selected from the group consisting of:
$OR^{11}$, $SR^{12}$, $S(O)R^{13}$, $SO_2R^{13}$, $C(O)R^{14}$, $CO(O)R^{14}$, $OC(O)R^{14}$, $NH_2$, $NHR^{15}$, $NR^{16}R^{17}$, $NHC(O)R^{14}$, $NR^{16}C(O)R^{14}$, $NHS(O)_2R^{13}$, $NR^{15}S(O)_2R^{13}$, $NHC(O)OR^{14}$, $NR^{15}C(O)OR^{14}$, $NHC(O)NH_2$, $NHC(O)NHR^{15}$, $NHC(O)NR^{16}R^{17}$, $NR^{15}C(O)NHR^{16}$, $NR^{15}C(O)NR^{16}R^{17}$, $C(O)NH_2$, $C(O)NHR^{15}$, $C(O)NR^{16}R^{17}$, $C(O)NR^{15}SO_2R^{13}$, $SO_2NH_2$, $SO_2NHR^{15}$, $SO_2NR^{16}R^{17}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^2$ aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one, two, or three substituents independently selected from the group consisting of: $OR^{18}$, $SR^{19}$, $S(O)R^{20}$, $SO_2R^{20}$, $C(O)R^{21}$, $CO(O)R^{22}$, $OC(O)R^{21}$, $NH_2$, $NHR^{23}$, $NR^{24}R^{25}$, $NHC(O)R^{21}$, $NR^{23}C(O)R^{21}$, $NHS(O)_2R^{20}$, $NR^{23}S(O)_2R^{20}$, $NHC(O)OR^{22}$, $NHC(O)NH_2$, $NHC(O)NHR^{23}$, $NHC(O)NR^{24}R^{25}$, $NR^{23}C(O)NHR^{23}$, $NR^{25}C(O)NR^{24}R^{25}$, $C(O)NH_2$, $C(O)NHR^{23}$, $C(O)NR^{24}R^{25}$, $C(O)NR^{23}SO_2R^{20}$, $SO_2NH_2$, $SO_2NHR^{23}SO_2NR^{24}R^{25}$, OH, CN, and halo;
$R^1$ is a cycloalkyl, cycloalkenyl, a heterocycloalkyl, or heterocycloalkenyl, each of which may be substituted with one to three substituents selected from the group consisting of:
$OR^{26}$, $SR^{27}$, $S(O)R^{28}$, $SO_2R^{28}$, $C(O)R^{29}$, $CO(O)R^{30}$, $OC(O)R^{29}$, $NH_2$, $NHR^{31}$, $NR^{32}R^{33}$, $NHC(O)R^{29}$, $NR^{31}C(O)R^{29}$, $NHS(O)_2R^{28}$, $NR^{31}S(O)_2R^{28}$, $NHC(O)OR^{30}$, $NR^{31}C(O)OR^{30}$, $NHC(O)NH_2$, $NHC(O)NHR^{31}$, $NHC(O)NR^{32}R^{33}$, $NR^{31}C(O)NHR^{32}$, $NR^{31}C(O)NR^{32}R^{33}$, $C(O)NH_2$, $C(O)NHR^{31}$, $C(O)NR^{32}R^{33}$, $C(O)NR^{31}SO_2R^{28}$, $SO_2NH_2$, $SO_2NHR^{31}$, $SO_2NR^{32}R^{33}$, OH, CN, halo, $C_1$-$C_8$ alkyl, $C_2$-$C_6$ alkenyl, $C_2$-$C_6$ alkynyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl; wherein each $R^1$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $R^{34}$, $OR^{34}$, $SR^{35}$, $S(O)R^{36}$, $SO_2R^{36}C(O)R^{37}$, $CO(O)R^{38}$, $OC(O)R^{37}$, $NH_2$, $NHR^{39}$, $NR^{40}R^{41}$, $NHC(O)R^{37}$, $NR^{39}C(O)R^{37}$, $NHS(O)_2R^{36}$, $NR^{39}S(O)_2R^{36}$, $NHC(O)OR^{38}$, $NHC(O)NH_2$, $NHC(O)NHR^{39}$, $NHC(O)NR^{40}R^{41}$, $NR^{39}C(O)NHR^{40}$, $NR^{39}C(O)NR^{40}R^{41}$, $C(O)NH_2$, $C(O)NHR^{39}$, $C(O)NR^{40}R^{41}$, $C(O)NR^{39}SO_2R^{36}$, $SO_2NH_2$, $SO_2NHR^{39}$, $SO_2NR^{40}R^{41}$, OH, CN, and halo;
$R^{10}$ is H or halo;
each of $R^{11}$ to $R^{41}$, are independently selected from the group consisting of: $C_1$-$C_8$ alkyl, aryl, heteroaryl, 5 to 7 membered heterocycloalkyl, 5 to 7 membered heterocycloalkenyl, $C_3$-$C_{10}$ cycloalkyl, and $C_5$-$C_{10}$ cycloalkenyl wherein each $R^{11}$ to $R^{41}$ $C_1$-$C_8$ alkyl, aryl, $C_3$-$C_{10}$ cycloalkyl, $C_5$-$C_{10}$ cycloalkenyl, heteroaryl, 5 to 7 membered heterocycloalkyl, and 5 to 7 membered heterocycloalkenyl may be substituted with one to three substituents independently selected from the group consisting of $OR^{42}$, $SR^{43}$, $S(O)R^{44}$, $SO_2R^{44}$, $C(O)R^{45}$, $CO(O)R^{46}$, OC(O)R⁴⁵, NH₂, NHR⁴⁷, NR⁴⁸R⁴⁹, NHC(O)R⁴⁵, NR⁴⁷C(O)R⁴⁵, NHS(O)₂R⁴⁴, NR⁴⁷S(O)₂R⁴⁴, C(O) NH₂, C(O)NHR⁴⁷, C(O)NR⁴⁰R⁴¹, C(O)NR⁴⁷SO₂R⁴⁴, SO₂NH₂, SO₂NHR⁴⁷, SO₂NR⁴⁸R⁴⁹, OH, CN, and halo; and each of R⁴² to R⁴⁹, are independently selected from the group consisting of: C₁-C₅ alkyl, aryl, heteroaryl, 5 to 7 membered heterocycloalkyl, 5 to 7 membered heterocycloalkenyl, C₃-C₁₀ cycloalkyl, and C₅-C₁₀ cycloalkenyl.

2. The compound of claim 1, or a pharmaceutically acceptable salt thereof, wherein R¹⁴ is H or halo.

3. The compound of claim 1, or a pharmaceutically acceptable salt thereof, wherein R¹⁰ is H.

4. The compound of claim 2, or a pharmaceutically acceptable salt thereof, wherein R¹ is a heterocycloalkyl, or heterocycloalkenyl, each of which may be substituted with one to three substituents selected from the group consisting of: SO₂R²⁸, C(O)R²⁹, C(O)NHR³¹, and C₁-C₈ alkyl; wherein each R¹ C₁-C₈ alkyl may be substituted with one to three substituents independently selected from the group consisting of R³⁴ and OH.

5. The compound of claim 2, or a pharmaceutically acceptable salt thereof, wherein R¹ is a heterocycloalkyl, which may be substituted with one to three substituents selected from the group consisting of: SO₂R²⁸, C(O)R²⁹, C(O)NHR³¹, and C₁-C₈ alkyl; wherein each R¹ C₁-C₈ alkyl may be substituted with one to three substituents independently selected from the group consisting of R³⁴ and OH.

6. The compound of claim 2, or a pharmaceutically acceptable salt thereof, wherein R¹ is a heterocycloalkenyl, which may be substituted with one to three substituents selected from the group consisting of: SO₂R²⁸, C(O)R²⁹, C(O)NHR³¹, and C₁-C₈ alkyl; wherein each R¹ C₁-C₈ alkyl may be substituted with one to three substituents independently selected from the group consisting of R³⁴ and OH.

7. The compound of claim 4, or a pharmaceutically acceptable salt thereof, wherein the bond between Y and Z is a single bond; Y is CH₂ and Z is CH₂; and J, X, and T are each independently CR³.

8. The compound of claim 4, or a pharmaceutically acceptable salt thereof, wherein the bond between Y and Z is a double bond; Y is N; Z is CH; and J, X, and T are each independently CR³.

9. The compound of claim 4, or a pharmaceutically acceptable salt thereof, wherein the bond between Y and Z is a double bond; Y is CR³; Z is CH; and J, X, and T are each independently CR³.

10. The compound of claim 4, or a pharmaceutically acceptable salt thereof, wherein the bond between Y and Z is a double bond; Y is N; Z is CH; and T is N; and J and X are each independently CR³.

11. The compound of claim 4, or a pharmaceutically acceptable salt thereof, wherein the bond between Y and Z is a double bond; Y is CR³; Z is CH; X is N; and J and T are each independently CR³.

12. The compound of claim 4, or a pharmaceutically acceptable salt thereof, wherein the bond between Y and Z is a double bond; Y is N; Z is N; and J, X, and T are each independently CR³.

13. The compound of claim 4, or a pharmaceutically acceptable salt thereof, wherein the bond between Y and Z is a double bond; Y is CR³; Z is CH; T is N; and J and X are each independently CR³.

14. The compound of claim 4, or a pharmaceutically acceptable salt thereof, wherein the bond between Y and Z is a double bond; Y is CR³; Z is CH; J is N; and X and T are each independently CR³.

15. The compound of claim 4, or a pharmaceutically acceptable salt thereof, wherein L is a C₁ alkylene; and R² is phenyl, a 4 to 7 membered heterocycloalkyl, or a five to six membered heteroaryl; each of which may substituted with one to three halo.

16. The compound of claim 1, wherein said compound is selected from the group consisting of:

4-[1-(3-fluorobenzyl)-2,3-dihydro-1H-indol-6-yl]-2-(piperidin-4-yl)-1H-pyrrolo[2,3-b]pyridine;

1-(3-fluorobenzyl)-6-[2-(piperidin-4-yl)-1H-pyrrolo[2,3-b]pyridin-4-yl]-1H-benzimidazole;

1-benzyl-6-[2-(piperidin-4-yl)-1H-pyrrolo[2,3-b]pyridin-4-yl]-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-benzimidazole;

6-[2-(piperidin-4-yl)-1H-pyrrolo[2,3-b]pyridin-4-yl]-1-(tetrahydro-2H-pyran-4-ylmethyl)-1H-benzimidazole;

6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

5-[2-(piperidin-4-yl)-1H-pyrrolo[2,3-b]pyridin-4-yl]-3-(tetrahydro-2H-pyran-4-ylmethyl)-3H-imidazo[4,5-b]pyridine;

1-(3-fluorobenzyl)-6-[2-(piperidin-4-yl)-1H-pyrrolo[2,3-b]pyridin-4-yl]-1H-indole-3-carbonitrile;

4-[5-fluoro-1-(3-fluorobenzyl)-1H-indol-6-yl]-2-(piperidin-4-yl)-1H-pyrrolo[2,3-b]pyridine;

6-{2-[1-(2,3-dihydroxypropyl)piperidin-4-yl]-1H-pyrrolo[2,3-b]pyridin-4-yl}-1-(3-fluorobenzyl)-1H-indole-3-carbonitrile;

1-(3-fluorobenzyl)-6-{2-[1-(methylsulfonyl)piperidin-4-yl]-1H-pyrrolo[2,3-b]pyridin-4-yl}-1H-indole-3-carbonitrile;

1-[(5-fluoropyridin-3-yl)methyl]-6-[2-(piperidin-4-yl)-1H-pyrrolo[2,3-b]pyridin-4-yl]-1H-benzimidazole;

1-[(5-fluoropyridin-3-yl)methyl]-6-{2-[1-(methylsulfonyl)piperidin-4-yl]-1H-pyrrolo[2,3-b]pyridin-4-yl}-1H-benzimidazole;

1-(3-fluorobenzyl)-6-[2-(1,2,3,6-tetrahydropyridin-4-yl)-1H-pyrrolo[2,3-b]pyridin-4-yl]-1H-benzimidazole;

1-(3-fluorobenzyl)-6-{2-[1-(methylsulfonyl)-1,2,3,6-tetrahydropyridin-4-yl]-1H-pyrrolo[2,3-b]pyridin-4-yl}-1H-benzimidazole;

4-(4-{1-[(5-fluoropyridin-3-yl)methyl]-1H-benzimidazol-6-yl}-1H-pyrrolo[2,3-b]pyridin-2-yl)-N-methylpiperidine-1-carboxamide;

3-[4-(4-{1-[(5-fluoropyridin-3-yl)methyl]-1H-benzimidazol-6-yl}-1H-pyrrolo[2,3-b]pyridin-2-yl)piperidin-1-yl]propane-1,2-diol;

5-fluoro-6-[2-(piperidin-4-yl)-1H-pyrrolo[2,3-b]pyridin-4-yl]-1-(tetrahydro-2H-pyran-4-ylmethyl)-1H-benzimidazole;

3-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)propane-1,2-diol;

4-{4-[5-fluoro-1-(tetrahydro-2H-pyran-4-ylmethyl)-1H-benzimidazol-6-yl}-1H-pyrrolo[2,3-b]pyridin-2-yl]-N-methylpiperidine-1-carboxamide;

1-(4-{4-[5-fluoro-1-(tetrahydro-2H-pyran-4-ylmethyl)-1H-benzimidazol-6-yl}-1H-pyrrolo[2,3-b]pyridin-2-yl]piperidin-1-yl)-2-hydroxyethanone;

1-benzyl-6-[6-(1,2,3,6-tetrahydropyridin-4-yl)-7H-pyrrolo[2,3-d]pyrimidin-4-yl]-1H-indole-3-carbonitrile;

5-fluoro-6-{2-[1-(methylsulfonyl)piperidin-4-yl]-1H-pyrrolo[2,3-b]pyridin-4-yl}-1-(tetrahydro-2H-pyran-4-ylmethyl)-1H-benzimidazole;

4-{4-[1-(3-fluorobenzyl)-1H-benzimidazol-6-yl}-1H-pyrrolo[2,3-b]pyridin-2-yl]-N-methyl-3,6-dihydropyridine-1(2H)-carboxamide;

3-[4-{4-[1-(3-fluorobenzyl)-1H-benzimidazol-6-yl]-1H-pyrrolo[2,3-b]pyridin-2-yl]-3,6-dihydropyridin-1(2H)-yl]propane-1,2-diol;

N-(4-{[4-{4-[1-(3-fluorobenzyl)-1H-benzimidazol-6-yl}-1H-pyrrolo[2,3-b]pyridin-2-yl]-3,6-dihydropyridin-1(2H)-yl]methyl}phenyl)acetamide;

5-chloro-6-[2-(piperidin-4-yl)-1H-pyrrolo[2,3-b]pyridin-4-yl]-1-(tetrahydro-2H-pyran-4-ylmethyl)-1H-benzimidazole;

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine-3-carbonitrile;

1-(3-fluorobenzyl)-6-[2-(piperidin-4-yl)-1H-pyrrolo[2,3-b]pyridin-4-yl]-1H-pyrrolo[3,2-b]pyridine;

6-[2-(piperidin-4-yl)-1H-pyrrolo[2,3-b]pyridin-4-yl]-1-(tetrahydro-2H-pyran-4-ylmethyl)-1H-pyrrolo[3,2-b]pyridine;

1-benzyl-6-{6-[1-(2,3-dihydroxypropyl)-1,2,3,6-tetrahydropyridin-4-yl]-7H-pyrrolo[2,3-d]pyrimidin-4-yl}-1H-indole-3-carbonitrile;

1-[2-(3-fluorophenyl)ethyl]-6-{2-(piperidin-4-yl)-1H-pyrrolo[2,3-b]pyridin-4-yl}-1H-benzotriazole;

6-[3-chloro-2-(piperidin-4-yl)-1H-pyrrolo[2,3-b]pyridin-4-yl]-1-[2-(3-fluorophenyl)ethyl]-1H-benzotriazole;

1-(3-fluorobenzyl)-6-{2-[1-(methylsulfonyl)piperidin-4-yl]-1H-pyrrolo[2,3-b]pyridin-4-yl}-1H-pyrrolo[3,2-b]pyridine;

1'-(3-fluorobenzyl)-2-(piperidin-4-yl)-1H,1'H-4,6'-bipyrrolo[2,3-b]pyridine-3'-carbonitrile;

1-(tetrahydro-2H-pyran-4-ylmethyl)-6-[2-(1,2,3,6-tetrahydropyridin-4-yl)-1H-pyrrolo[2,3-b]pyridin-4-yl]-1H-benzotriazole;

1[(5-fluoropyridin-3-yl)methyl]-6-[2-(piperidin-4-yl)-1H-pyrrolo[2,3-b]pyridin-4-yl]-1H-pyrrolo[3,2-b]pyridine;

2-hydroxy-1-[4-{4-[1-(tetrahydro-2H-pyran-4-ylmethyl)-1H-benzotriazol-6-yl]-1H-pyrrolo[2,3-b]pyridin-2-yl}-3,6-dihydropyridin-1(2H)-yl]ethanone;

6-{2-[1-(methylsulfonyl)-1,2,3,6-tetrahydropyridin-4-yl]-1H-pyrrolo[2,3-b]pyridin-4-yl}-1-(tetrahydro-2H-pyran-4-ylmethyl)-1H-benzotriazole;

1-(3-fluorobenzyl)-6-[2-(1,2,3,6-tetrahydropyridin-4-yl)-1H-pyrrolo[2,3-b]pyridin-4-yl]-1H-pyrrolo[3,2-b]pyridine;

methyl 5-fluoro-1-(3-fluorobenzyl)-6-[2-(piperidin-4-yl)-1H-pyrrolo[2,3-b]pyridin-4-yl]-1H-indole-3-carboximidate;

5-fluoro-1-(3-fluorobenzyl)-6-[2-(piperidin-4-yl)-1H-pyrrolo[2,3-b]pyridin-4-yl]-1H-indole-3-carbonitrile;

1'-(3-fluorobenzyl)-2-(piperidin-4-yl)-1H,1'H-4,6'-bipyrrolo[2,3-b]pyridine;

2-(piperidin-4-yl)-1'-(tetrahydro-2H-pyran-4-ylmethyl)-1H,1'H-4,6'-bipyrrolo[2,3-b]pyridine;

4-{4-[1-(3-fluorobenzyl)-1H-pyrrolo[3,2-b]pyridin-6-yl]-1H-pyrrolo[2,3-b]pyridin-2-yl}-N-methylpiperidine-1-carboxamide;

6-{2-[1-(methylsulfonyl)piperidin-4-yl]-1H-pyrrolo[2,3-b]pyridin-4-yl}-1-(tetrahydro-2H-pyran-4-ylmethyl)-1H-pyrrolo[3,2-b]pyridine;

4-(4-{1-[(5-fluoropyridin-3-yl)methyl]-1H-pyrrolo[3,2-b]pyridin-6-yl}-1H-pyrrolo[2,3-b]pyridin-2-yl)-N-methylpiperidine-1-carboxamide;

1-[(5-fluoropyridin-3-yl)methyl]-6-{2-[1-(methylsulfonyl)piperidin-4-yl]-1H-pyrrolo[2,3-b]pyridin-4-yl}-1H-pyrrolo[3,2-b]pyridine;

1'-[(5-fluoropyridin-3-yl)methyl]-2-(piperidin-4-yl)-1H,1'H-4,6'-bipyrrolo[2,3-b]pyridine;

1-[(5-fluoropyridin-3-yl)methyl]-6-[2-(1,2,3,6-tetrahydropyridin-4-yl)-1H-pyrrolo[2,3-b]pyridin-4-yl]-1H-pyrrolo[3,2-b]pyridine;

1'-[(5-fluoropyridin-3-yl)methyl]-2-(1,2,3,6-tetrahydropyridin-4-yl)-1H,1'H-4,6'-bipyrrolo[2,3-b]pyridine;

4-{1'-[(5-fluoropyridin-3-yl)methyl]-1H,1'H-4,6'-bipyrrolo[2,3-b]pyridin-2-yl}-N-methylpiperidine-1-carboxamide;

1'-[(5-fluoropyridin-3-yl)methyl]-2-[1-(methylsulfonyl)piperidin-4-yl]-1H,1'H-4,6'-bipyrrolo[2,3-b]pyridine;

4-{1'-[(5-fluoropyridin-3-yl)methyl]-1H,1'H-4,6'-bipyrrolo[2,3-b]pyridin-2-yl}-N-methyl-3,6-dihydropyridine-1(2H)-carboxamide;

1'-[(5-fluoropyridin-3-yl)methyl]-2-[1-(methylsulfonyl)-1,2,3,6-tetrahydropyridin-4-yl]-1H,1'H-4,6'-bipyrrolo[2,3-b]pyridine;

1'-[(5-fluoropyridin-3-yl)methyl]-2-(1,2,5,6-tetrahydropyridin-3-yl)-1H,1'H-4,6'-bipyrrolo[2,3-b]pyridine;

and pharmaceutically acceptable salts thereof.

17. A pharmaceutical composition comprising an excipient and a therapeutically effective amount of a compound of claim 1 or a pharmaceutically acceptable salt thereof.

* * * * *

UNITED STATES PATENT AND TRADEMARK OFFICE
CERTIFICATE OF CORRECTION

PATENT NO.       : 8,969,375 B2                                Page 1 of 1
APPLICATION NO.  : 14/207841
DATED            : March 3, 2015
INVENTOR(S)      : Lai et al.

It is certified that error appears in the above-identified patent and that said Letters Patent is hereby corrected as shown below:

Claims

Column 88, line 27, claim 1: "$SO_2NHR^{23}SO_2NR^{24}R^{25}$," to read as --$SO_2NHR^{23}$, $SO_2NR^{24}R^{25}$,--

Column 88, line 49, claim 1: "$SO_2R^{36}C(O)R^{37}$," to read as --$SO_2R^{36}$, $C(O)R^{37}$,--

Signed and Sealed this
Tenth Day of November, 2015

Michelle K. Lee
*Director of the United States Patent and Trademark Office*